United States Patent
Carson et al.

(10) Patent No.: US 6,548,499 B1
(45) Date of Patent: Apr. 15, 2003

(54) SUBSTITUTED QUINOXALINE DERIVATIVES AS INTERLEUKIN-8 RECEPTOR ANTAGONISTS

(75) Inventors: Kenneth G. Carson, Needham, MA (US); David Thomas Connor, Ann Arbor, MI (US); Jie Jack Li, Ann Arbor, MI (US); Joseph Edwin Low, Brighton, MI (US); Jay R. Luly, Wellesley, MA (US); Steven Robert Miller, Ann Arbor, MI (US); Bruce David Roth, Plymouth, MI (US); Bharat Kalidas Trivedi, Farmington Hills, MI (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/622,423

(22) PCT Filed: Feb. 5, 1999

(86) PCT No.: PCT/US99/02581

§ 371 (c)(1), (2), (4) Date: Oct. 20, 2000

(87) PCT Pub. No.: WO99/42463

PCT Pub. Date: Aug. 26, 1999

Related U.S. Application Data

(60) Provisional application No. 60/075,551, filed on Feb. 23, 1998.

(51) Int. Cl.[7] .................... A61K 31/495; C07D 401/04; C07D 403/04; C07D 405/04; C07D 409/04
(52) U.S. Cl. ................ 514/249; 544/353; 544/356
(58) Field of Search .................. 544/353, 356; 514/249

(56) References Cited

FOREIGN PATENT DOCUMENTS

EP 288898 * 11/1988
GB 1574429 * 9/1980

OTHER PUBLICATIONS

Monge et al *Chemical Abstracts*, vol. 123, No. 55808, 1995.*
Oppenheim J.J. et al., "Properties of the novel proinflammatory supergene "intercrine" cytokine family." *Annu. Rev. Immunol.*, 1991;9:617–648.
Baggiolini et al., *FEBS Lett.*, 1992; 307:97.
Miller et al., *Crit. Rev. Immunol.*, 1992;12:17.
Seitz et al., *J. Clin Invest.*, 1991;87:643.
Miller et al., *Am. Rev. Respir. Dis.*, 1992;146:427.
Donnely et al., *Lancet*, 1993;341:643.
Sekido N., Mukaida N. et al., "Prevention of lung reperfusion injury in rabbits by a monoclonal antibody against interleukin–8." *Nature*, 1993;365(6447);654–7 Issn: 0028–0836.
Broaddus V.C., Boylan A.M. et al., "Neutralization of IL–8 inhibits neutrophil influx in a rabbit model of endotoxin–induced pleurisy," *J. Immunol.*, 1994;152(6):2960–2967.
Cacalano G., Lee J. et al., "Neutrophil and b cell expansion in mice that lack the murine IL–8 receptor homolog,"*Science*, 1994:265(5172):682–4 Issn: 0036–8075.
Herbert et al., *Cancer Invest.*, 1993;11:743.
Richards et al., *American Journal of Surgery*, 1997;174:507.
Berge S.M. et al., "Pharmaceutical Salts," *J. of Pharma Sci.*, 1977;66:1.
Carr M.W., Roth S.J., Luther E., Rose S.S., and Springer T.A., "Monocyte chemoattractant protein 1 acts as a T–lymohocyte chemoattractant," *Proc. Natl. Acad. Sci USA*, 1994;91:3652.
Qin S., Larosa G., Campbell J.J. et al., "Expression of MCP–1 and IL–8 receptors on subset on T–cells, and correlation with transendothelial chemotactic potential," *Eur. J. Immu.*, 1996;26:640.
Neote K., DiGregorio D., Mak J.Y., Horuk R., and Schall T.J., "Molecular cloning, functional expression, and signaling characteristics of a C–C chemokine receptor," *Cell*, 1993;72:415.
E. Elslager, C. Hess, and L. Werbel,*J. Med. Chem.*, 1968;11:630.
D. Moderhack, et al., *Chemische Berichte*, 1994:1633.
Loriga M. et al., *Farmaco*, 1995;50(5):289.
Blagbroug I.S., Moya E., Walford S.P.,*Tetrahedron. Letters*, 1996;37:551.

* cited by examiner

Primary Examiner—Richard L. Raymond
(74) Attorney, Agent, or Firm—Lahive & Cockfield, LLP; Guilio A. DeConti, Jr.; Elizabeth A. Hanley

(57) ABSTRACT

Quinoxaline compounds are described as well as methods for the preparation and pharmaceutical compositions of same, which are useful as interleukin-8 (IL-8) receptor antagonists and can be used in the treatment of a chemokine-mediated disease wherein the chemokine binds to an IL-8a (CXCR1) or b (CXCR2) receptor such as a chemokine-mediated disease selected from psoriasis, or atopic distress syndrome, arthritis, inflammatory bowel disease, Crohn's disease, ulcerative colitis, gastric ulcer, septic shock, endotoxic shock, gram-negative sepsis, toxic shock syndrome, stroke, cardiac and renal reperfusion injury, glomerulonephritis, or thrombosis, Alzheimer's disease, graft versus host reaction, allograft rejections, or allergic diseases.

20 Claims, No Drawings

SUBSTITUTED QUINOXALINE DERIVATIVES AS INTERLEUKIN-8 RECEPTOR ANTAGONISTS

This application is a 371 of PCT/US99/02881, filed Feb. 5, 1999 and claims benefit of U.S. Provisional Application No. 60/075,551, filed Feb. 23, 1998.

BACKGROUND OF THE INVENTION

The present invention relates to novel quinoxaline compounds useful as pharmaceutical agents, to methods for their production, to pharmaceutical compositions which include these compounds and a pharmaceutical carrier, and to pharmaceutical methods of treatment. The compounds of the present invention are Interleukin-8 (IL-8) receptor antagonists. More particularly, the compounds of the present invention are useful in the treatment of a chemokine-mediated disease wherein the chemokine binds to an IL-8a (CXCR1) or b (CXCR2) receptor such as, for example, a chemokine-mediated disease selected from psoriasis, or atopic dermatitis, tumor growth and angiogenesis, asthma, chronic obstructive pulmonary disease, adult respiratory distress syndrome, arthritis, inflammatory bowel disease, Crohn's disease, ulcerative colitis, gastric ulcer, septic shock, endotoxic shock, gram-negative sepsis, toxic shock syndrome, stroke, cardiac and renal reperfusion injury, glomerulo-nephritis, or thrombosis, Alzheimer's disease, graft versus host reaction, allograft rejections, or allergic diseases.

IL-8 is a 72 amino acid protein which is a member of the superfamily of leukocyte chemoattractant proteins which have been referred to as intercrines, C-X-C or C-C cytokines or, more recently as chemokines (Oppenheim J. J. et al., "Properties of the novel proinflammatory supergene "intercrine" cytokine family." *Annu. Rev. Immunol.*, 1991;9:617–648). Many members of the chemokine family appear to be involved in the inflammatory process and in the trafficking of leukocytes. The chemokine superfamily is composed of two branches: the α- and the β-chemokines. The α-chemokine branch includes IL-8, neutrophil activating peptide-2 (NAP-2), melanoma growth stimulatory activity (MGSA/gro or GROα), and ENA-78, all of which have attracting and activating effects predominantly on neutrophils. This branch also includes PF4, β-thromboglobulin, and CTAPIII, which do not affect neutrophils.

IL-8 was originally identified by its ability to both attract and activate polymorphonuclear leukocytes (neutrophils) and has now been shown to be rapidly induced in a wide variety of cell and tissue types in response to pro-inflammatory cytokines such as IL-1b or TNFα. Additionally, there is data demonstrating high systemic levels of IL-8 in certain neutrophil-mediated inflammatory diseases, suggesting the IL-8 and closely related factors may be the principal endogenous mediators of neutrophil activation. Many reports have been published regarding disorders in which high levels of IL-8 have been measured, and include rheumatoid arthritis, septic shock, asthma, cystic fibrosis, myocardial infarction, and psoriasis (Baggiolini et al., *FEBS Lett*, 1992;307:97; Miller et al., *Crit. Rev. Immunol.*, 1992;12:17. Oppenhein et al., *Annu. Rev. Immunol*, 1991;9:617; Seitz et al., *J. Clin. Invest.*, 1991;87:463; Miller et al., *Am. Rev. Respir. Dis.*, 1992;146:427; Donnely et al., *Lancet*, 1993;341:643). Strong in vivo evidence indicating a central role of IL-8 in the pathology related to lung ischemia/reperfusion has recently been published (Sekido N., Mukaida N. et al., "Prevention of lung reperfusion injury in rabbits by a monoclonal antibody against interleukin-8." *Nature*, 1993;365(6447):654–7 Issn: 0028-0836). A monoclonal antibody to rabbit IL-8, capable of blocking the in vitro neutrophil chemotactic activity of IL-8, prevented tissue damage in the rabbit lung normally resulting from lung ischemia/reperfusion. More recently, another study has shown beneficial effects of an IL-8 neutralizing antibody in an endotoxin-induced pleurisy model in rabbit (Broaddus V. C., Boylan A. M. et al., "Neutralization of IL-8 inhibits neutrophil influx in a rabbit model of endotoxin-induced pleurisy," *J. Immunol.*, 1994;152(6):2960–2967). There were also reports indicating similar beneficial effects with IL-8 neutralizing antibodies in animal models of dermatitis, joint arthritis, and glomerulonephritis. Additionally, knockout mice have been generated in which the apparent mouse homologue of the IL-8R (closer to IL-8RB) was deleted by homologous recombination (Cacalano G., Lee J. et al., "Neutrophil and b cell expansion in mice that lack the murine IL-8 receptor homolog," *Science*, 1994;265(5172):682–4 Issn: 0036-8075). Although these mice appear healthy, their neutrophils are greatly impaired, as compared to wild-type mice, in their ability to migrate to the peritoneum in response to intraperitoneal thioglycollate injection. All of these results suggest that IL-8 is an important mediator of neutrophil migration and activity in some inflammatory settings, and that a small molecule antagonist to the receptors for IL-8 should prove to be an effective treatment for some inflammatory pathologies and has the potential to be a broadly useful anti-inflammatory agent. Also, there have been reports that IL-8 is an important cytokine involved in tumor growth and angiogenesis in a variety of malignancies (Hebert et al., *Cancer Invest.*, 1993;11:743 and Richards et al., *American Journal of Surgery*, 1997;174:507).

We have identified a series of quinoxalines that are IL-8 receptor antagonists and which can additionally be used in psoriasis, or atopic dermatitis, disease associated with pathological angiogenesis (i.e. cancer), asthma, chronic obstructive pulmonary disease, adult respiratory distress syndrome, arthritis, inflammatory bowel disease, Crohn's disease, ulcerative colitis, gastric ulcer, septic shock, endotoxic shock, gram-negative sepsis, toxic shock syndrome, stroke, cardiac and renal reperfusion injury, glomerulo-nephritis, or thrombosis, Alzheimer's disease, graft versus host reaction, allograft rejections, or allergic diseases.

SUMMARY OF THE INVENTION

Accordingly, a first aspect of the present invention is a compound of Formula I

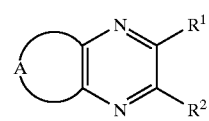

I wherein A is selected from the group consisting of:

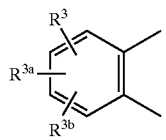

wherein $R^3$, $R^{3a}$, and $R^{3b}$ are each independently the same or different and are hydrogen,
alkyl,
aryl-$SO_2$—,
aryl,
heteroaryl,
—$OR^4$ wherein $R^4$ is hydrogen,
  alkyl,
  aryl,
  aralkyl,
  acetyl, or

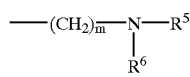

wherein
$R^5$ and $R^6$ are each the same or different and are hydrogen, alkyl, cycloalkyl, acetyl, —$(CH_2)_m$—OH, or
$R^5$ and $R^6$ are taken together to form a 5- to 7-membered ring optionally containing an oxygen atom or N—$R^4$ wherein $R^4$ is as defined above and m is an integer of 2 to 5,

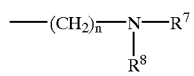

wherein n is zero or an integer of 1 and $R^7$ and $R^8$ are each independently the same or different and are
hydrogen,
alkyl,
aryl,
aralkyl,
acetyl, or

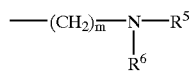

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

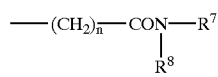

wherein $R^7$, $R^8$, and n are as defined above,

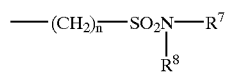

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$,

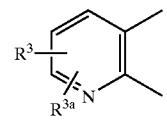

wherein $R^3$ and $R^{3a}$ are as defined above,

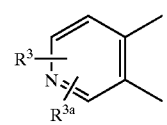

wherein $R^3$ and $R^{3a}$ are as defined above,

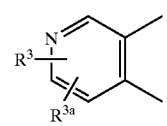

wherein $R^3$ and $R^{3a}$ are as defined above,

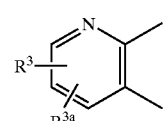

wherein $R^3$ and $R^{3a}$ are as defined above,

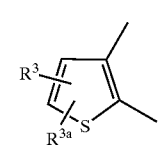

wherein $R^3$ and $R^{3a}$ are as defined above,

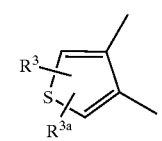

wherein $R^3$ and $R^{3a}$ are as defined above,

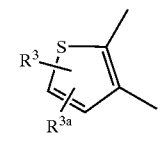

wherein R³ and R³ᵃ are as defined above, and

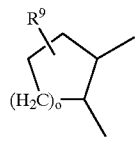

wherein o is an integer of 1 or 2, and R⁹ is hydrogen or alkyl;

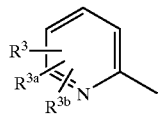

wherein R³, R³ᵃ, and R³ᵇ are as defined above,

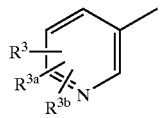

wherein R³, R³ᵃ, and R³ᵇ are as defined above,

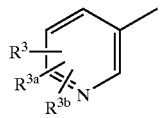

wherein R³, R³ᵃ, and R³ᵇ are as defined above,

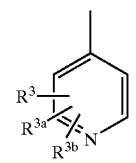

wherein R³, R³ᵃ, and R³ᵇ are as defined above,

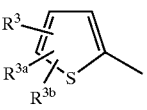

wherein R³, R³ᵃ, and R³ᵇ are as defined above,

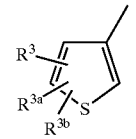

wherein R³, R³ᵃ, and R³ᵇ are as defined above,

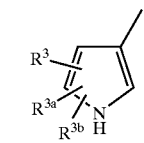

wherein R³, R³ᵃ, and R³ᵇ are as defined above,

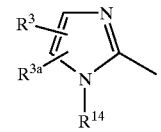

wherein R¹⁴ is hydrogen, alkyl, aryl, or aralkyl, and R³ and R³ᵃ are as defined above,

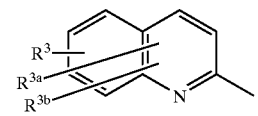

wherein R³, R³ᵃ, and R³ᵇ are as defined above,

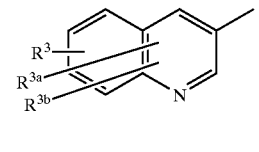

wherein R³, R³ᵃ, and R³ᵇ are as defined above,

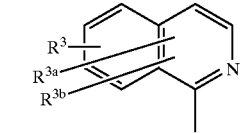

wherein R³, R³ᵃ, and R³ᵇ are as defined above,

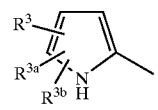

wherein R³, R³ᵃ, and R³ᵇ are as defined above,

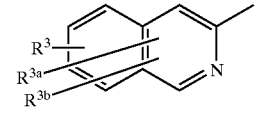

wherein R³, R³ᵃ, and R³ᵇ are as defined above,

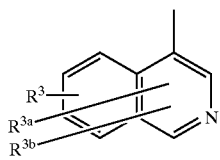

wherein R³, R³ᵃ, and R³ᵇ are as defined above,

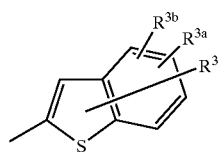

wherein R³, R³ᵃ, and R³ᵇ are as defined above,

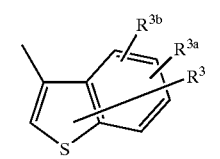

wherein R³, R³ᵃ, and R³ᵇ are as defined above,

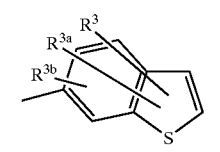

wherein R³, R³ᵃ, and R³ᵇ are as defined above,

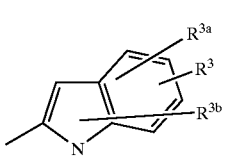

wherein R³, R³ᵃ, and R³ᵇ are as defined above,

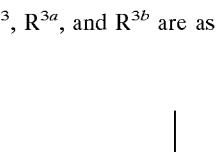

wherein R³, R³ᵃ, and R³ᵇ are as defined above,

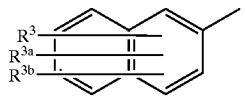

wherein R³, R³ᵃ, and R³ᵇ are as defined above,

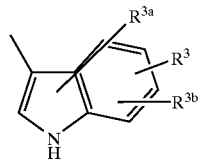

wherein R³, R³ᵃ, and R³ᵇ are as defined above,

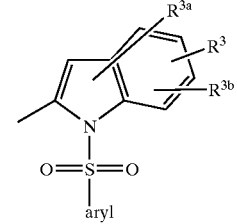

wherein R³, R³ᵃ, and R³ᵇ are as defined above,

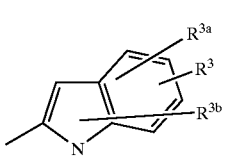

wherein R³, R³ᵃ, and R³ᵇ are as defined above,

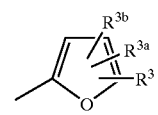

wherein R³, R³ᵃ, and R³ᵇ are as defined above,

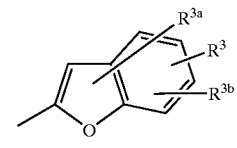

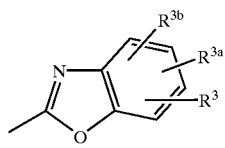

wherein R³, R³ᵃ, and R³ᵇ are as defined above,

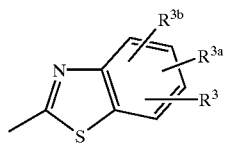

wherein R³, R³ᵃ, and R³ᵇ are as defined above,

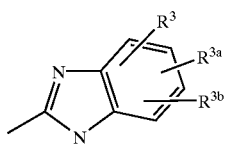

wherein R³, R³ᵃ, and R³ᵇ are as defined above,

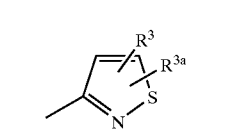

wherein R³ and R³ᵃ are as defined above,

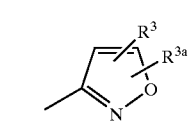

wherein R³ and R³ᵃ are as defined above,

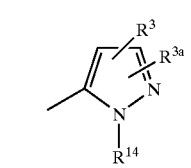

wherein R³, R³ᵃ, and R¹⁴ are as defined above,

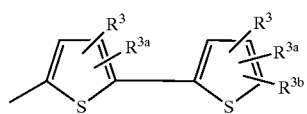

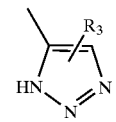

wherein R³ is as defined above,

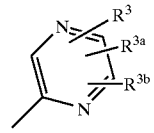

wherein R³, R³ᵃ, and R³ᵇ are as defined above,

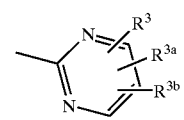

wherein R³, R³ᵃ, and R³ᵇ are as defined above,

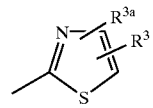

wherein R³ and R³ᵃ are as defined above,

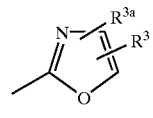

wherein R³ and R³ᵃ are as defined above,

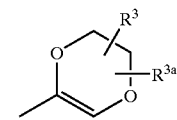

wherein R³ and R³ᵃ are as defined above,

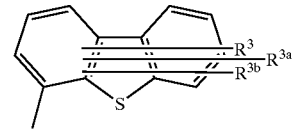

wherein R³, R³ᵃ, and R³ᵇ are as defined above,

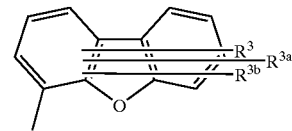

wherein $R^3$, $R^{3a}$, and $R^{3b}$ are as defined above,

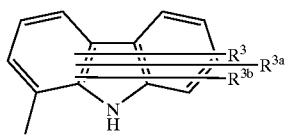

wherein $R^3$, $R^{3a}$, and $R^{3b}$ are as defined above,

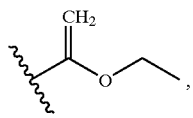

halogen, or
alkoxy, with the proviso
  that when A is

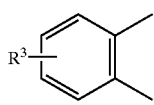

wherein $R^3$ is hydrogen, methyl, or
chloro, $R^1$ is not

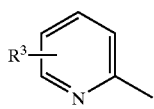

wherein $R^3$ is hydrogen; and
$R^2$ is $CF_3$,
  $CCl_3$,
  $CBr_3$, or

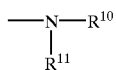

wherein $R^{10}$ is hydrogen,
  alkyl, or
  aralkyl,

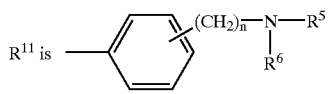

wherein n, $R^5$, and $R^6$ are as defined above,

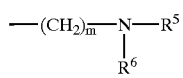

wherein $R^5$, $R^6$, and m are as defined above,

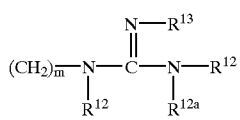

wherein $R^{12}$ and $R^{12a}$ are each independently the same or different and are hydrogen, alkyl, or aryl, or taken together can form a 5- to 7-membered ring, and
$R^{13}$ is hydrogen or alkyl, and
m is as defined above,

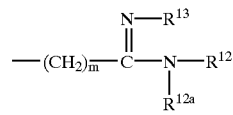

wherein m, $R^{12}$, $R^{12a}$, and $R^{13}$ are as defined above,

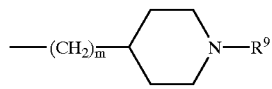

wherein $R^9$ and m are as defined above,

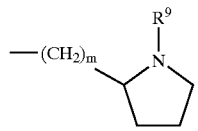

wherein $R^9$ and m are as defined above,

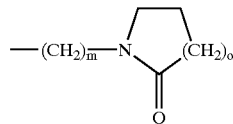

wherein m and o are as defined above,

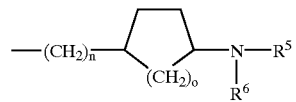

wherein n, o, $R^5$, and $R^6$ are as defined above,

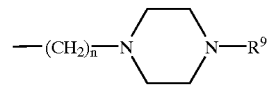

wherein n and $R^9$ are as defined above,

wherein n is as defined above,

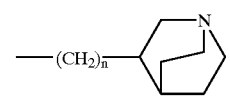

wherein n is as defined above,

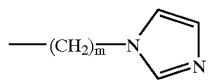

wherein m is as defined above, or
$R^{10}$ and $R^{11}$ when taken together can form a 5- to 7-membered ring optionally containing an oxygen atom or N—$R^4$ wherein $R^4$ is as defined above;
or a pharmaceutically acceptable salt thereof.

A second aspect of the present invention is a method of treating a chemokine-mediated disease state, wherein the chemokine binds to an IL-8a (CXCR1) or b (CXCR2) receptor in a mammal, which comprises administering to said mammal an effective amount of compound of Formula II

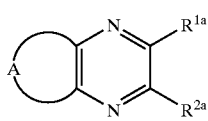

wherein A is selected from the group consisting of:

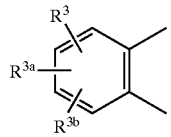

wherein $R^3$, $R^{3a}$, and $R^{3b}$ are each independently the same or different and are hydrogen,
  alkyl,
  aryl-$SO_2$—,
  aryl,
  heteroaryl,
  —$OR^4$ wherein $R^4$ is hydrogen,
    alkyl,
    aryl,
    aralkyl,
    acetyl, or

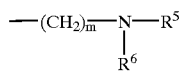

wherein $R^5$ and $R^6$ are each the same or different and are hydrogen,
  alkyl, cycloalkyl, acetyl, —$(CH_2)_m$—OH, or
  $R^5$ and $R^6$ are taken together to form a 5- to 7-membered ring optionally containing an oxygen atom or N—$R^4$ wherein $R^4$ is as defined above and m is an integer of 2 to 5,

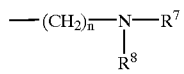

wherein n is zero or an integer of 1 and $R^7$ and $R^8$ are each independently the same or different and are hydrogen,
  alkyl,
  aryl,
  aralkyl,
  acetyl, or

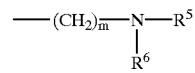

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

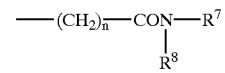

wherein $R^7$, $R^8$, and n are as defined above,

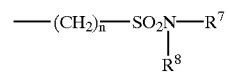

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$,

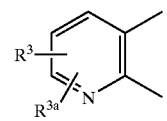

wherein $R^3$ and $R^{3a}$ are as defined above,

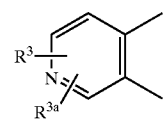

wherein $R^3$ and $R^{3a}$ are as defined above,

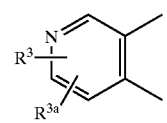

wherein $R^3$ and $R^{3a}$ are as defined above,

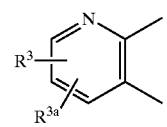

wherein R³ and R³ᵃ are as defined above,

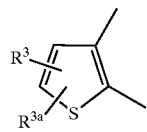

wherein R³ and R³ᵃ are as defined above,

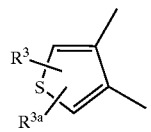

wherein R³ and R³ᵃ are as defined above,

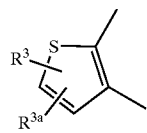

wherein R³ and R³ᵃ are as defined above,

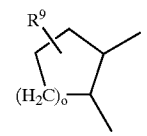

wherein o is an integer of 1 or 2, and R⁹ is hydrogen or alkyl;

R¹ᵃ is 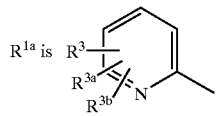

wherein R³, R³ᵃ, and R³ᵇ are as defined above,

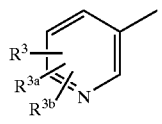

wherein R³, R³ᵃ, and R³ᵇ are as defined above,

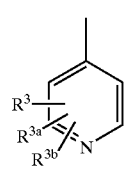

wherein R³, R³ᵃ, and R³ᵇ are as defined above,

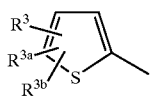

wherein R³, R³ᵃ, and R³ᵇ are as defined above,

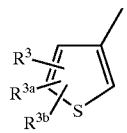

wherein R³, R³ᵃ, and R³ᵇ are as defined above,

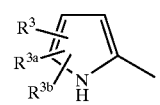

wherein R³, R³ᵃ, and R³ᵇ are as defined above,

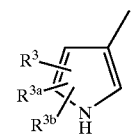

wherein R¹⁴ is hydrogen, alkyl, aryl, or aralkyl, and R³ and R³ᵃ are as defined above,

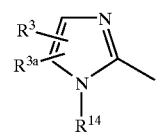

wherein R³, R³ᵃ, and R³ᵇ are as defined above,

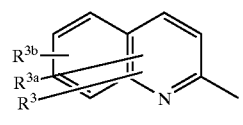

wherein R³, R³ᵃ, and R³ᵇ are as defined above,

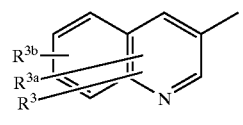

wherein R³, R³ᵃ, and R³ᵇ are as defined above,

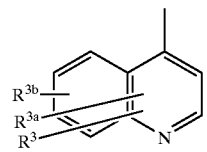

wherein R³, R³ᵃ, and R³ᵇ are as defined above,

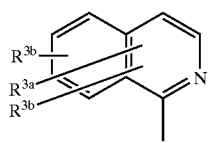

wherein R³, R³ᵃ, and R³ᵇ are as defined above,

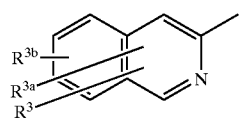

wherein R³, R³ᵃ, and R³ᵇ are as defined above,

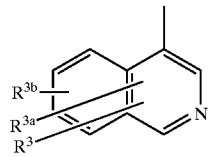

wherein R³, R³ᵃ, and R³ᵇ are as defined above,

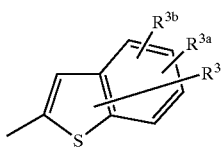

wherein R³, R³ᵃ, and R³ᵇ are as defined above,

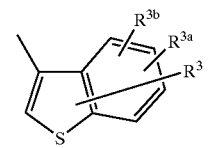

wherein R³, R³ᵃ, and R³ᵇ are as defined above,

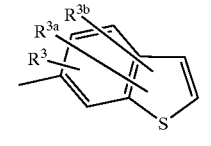

wherein R³, R³ᵃ, and R³ᵇ are as defined above,

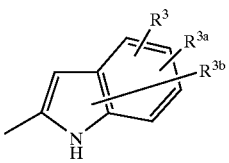

wherein R³, R³ᵃ, and R³ᵇ are as defined above,

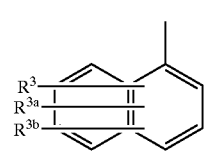

wherein R³, R³ᵃ, and R³ᵇ are as defined above,

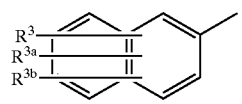

wherein R³, R³ᵃ, and R³ᵇ are as defined above,

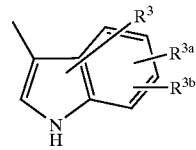

wherein R³, R³ᵃ, and R³ᵇ are as defined above,

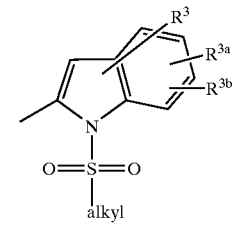

wherein R³, R³ᵃ, and R³ᵇ are as defined above,

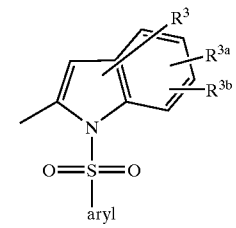

wherein R³, R³ᵃ, and R³ᵇ are as defined above,

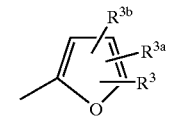

wherein R³, R³ᵃ, and R³ᵇ are as defined above,

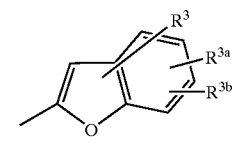

wherein R³, R³ᵃ, and R³ᵇ are as defined above,

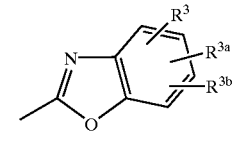

wherein $R^3$, $R^{3a}$, and $R^{3b}$ are as defined above,

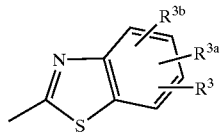

wherein $R^3$, $R^{3a}$, and $R^{3b}$ are as defined above,

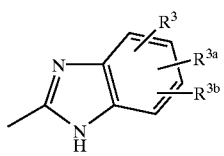

wherein $R^3$, $R^{3a}$, and $R^{3b}$ are as defined above,

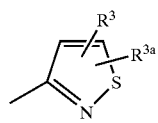

wherein $R^3$ and $R^{3a}$ are as defined above,

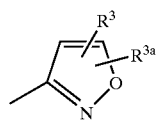

wherein $R^3$ and $R^{3a}$ are as defined above,

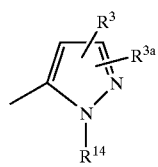

wherein $R^3$, $R^{3a}$, and $R^{14}$ are as defined above,

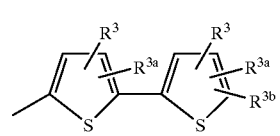

wherein $R^3$, $R^{3a}$, and $R^{3b}$ are as defined above,

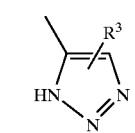

wherein $R^3$ is as defined above,

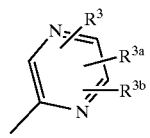

wherein $R^3$, $R^{3a}$, and $R^{3b}$ are as defined above,

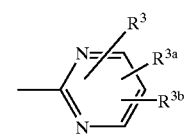

wherein $R^3$, $R^{3a}$, and $R^{3b}$ are as defined above,

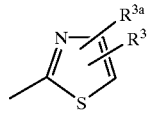

wherein $R^3$ and $R^{3a}$ are as defined above,

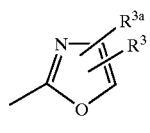

wherein $R^3$ and $R^{3a}$ are as defined above,

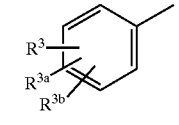

wherein $R^3$, $R^{3a}$, and $R^{3b}$ are as defined above,

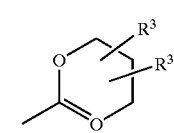

wherein $R^3$ and $R^{3a}$ are as defined above,

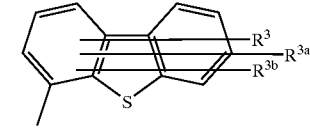

wherein $R^3$, $R^{3a}$, and $R^{3b}$ are as defined above,

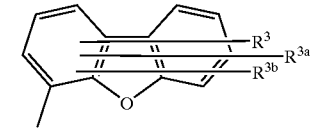

wherein $R^3$, $R^{3a}$, and $R^{3b}$ are as defined above,

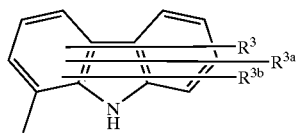

wherein $R^3$, $R^{3a}$, and $R^{3b}$ are as defined above,

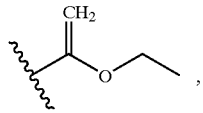

alkyl,
halogen,
alkoxy,
—$OR^4$ wherein $R^4$ is as defined above, or

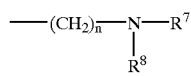

wherein $R^7$, $R^8$, and n are as defined above; and
$R^{2a}$ is $CF_3$,
$CCl_3$,
$CBr_3$, or

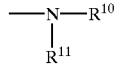

wherein $R^{10}$ is hydrogen,
alkyl, or
aralkyl, and

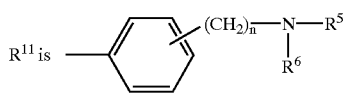

wherein n, $R^5$, and $R^6$ are as defined above,

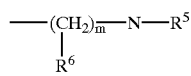

wherein $R^5$, $R^6$, and m are as defined above,

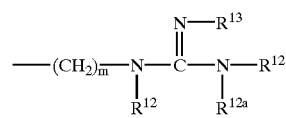

wherein $R^{12}$ and $R^{12a}$ are each independently the same or different and are
hydrogen,
alkyl, or
aryl, or taken together can form a 5- to 7-membered ring, and
$R^{13}$ is hydrogen or alkyl, and m is as defined above,

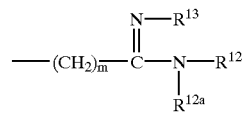

wherein m, $R^{12}$, $R^{12a}$, and $R^{13}$ are as defined above,

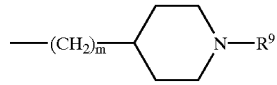

wherein $R^9$ and m are as defined above,

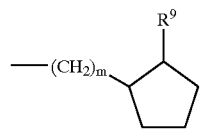

wherein $R^9$ and m are as defined above,

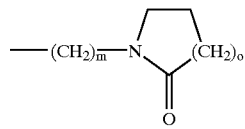

wherein m and o are as defined above,

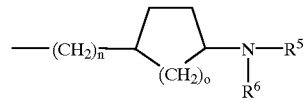

wherein n, o, $R^5$, and $R^6$ are as defined above,

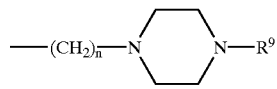

wherein n and $R^9$ are as defined above,

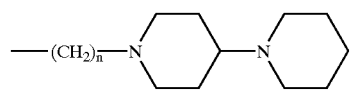

wherein n is as defined above,

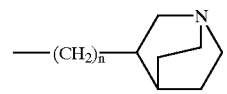

wherein n is as defined above,

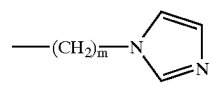

wherein m is as defined above, or

R$^{10}$ and R$^{11}$ when taken together can form a 5- to 7-membered ring optionally containing an oxygen atom or N—R$^4$ wherein R$^4$ is as defined above;

or a pharmaceutically acceptable salt thereof.

As inhibitors of chemokine-mediated diseases, the compounds of Formula I and II can be used as agent for treating psoriasis, or atopic dermatitis, disease associated with pathological angiogenesis (i.e. cancer), asthma, chronic obstructive pulmonary disease, adult respiratory distress syndrome, arthritis, inflammatory bowel disease, Crohn's disease, ulcerative colitis, gastric ulcer, septic shock, endotoxic shock, gram-negative sepsis, toxic shock syndrome, stroke, cardiac and renal reperfusion injury, glomerulo-nephritis, or thrombosis, Alzheimer's disease, graft versus host reaction, allograft rejections, or allergic diseases.

A still further embodiment of the present invention is a pharmaceutical composition for administering an effective amount of a compound of Formula I or Formula II in unit dosage form in the treatment methods mentioned above. Finally, the present invention is directed to methods for production of compounds of Formula I or Formula II.

DETAILED DESCRIPTION OF THE INVENTION

In the compounds of Formula I or II, the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

The term "cycloalkyl" means a saturated hydrocarbon ring which contains from 3 to 8 carbon atoms, for example, cyclopropyl, cyclobutyl, cyclopentyl, cyclohexyl, cycloheptyl, and the like.

"Alkoxy" and "thioalkoxy" are O-alkyl or S-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, nitro, cyano, carboxy, SO$_3$H, CHO,

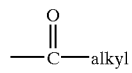

as defined above for alkyl,

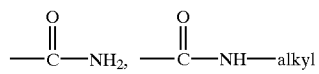

as defined above for alkyl,

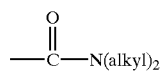

as defined above for alkyl, —(CH$_2$)$_n$—NH$_2$ wherein n is an integer of 1 to 5, —(CH$_2$)$_n$—NH-alkyl as defined above for alkyl and n, —(CH$_2$)$_n$—N(alkyl)$_2$ as defined above for alkyl and n.

The term "heteroaryl" means a heteroaromatic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, N-formyl-2-, 3-, 4-, 5-, 6-, or 7-indolyl, 2-, 3-, 4-, 5-, 6-, or 7-benzo[b]thienyl, 2-, 3-, 4-, 5-, 6-, or 7-benzo[b]furanyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by one to three substituents selected from alkyl as defined above, alkoxy as defined above, thioalkoxy as defined above, hydroxy, halogen, trifluoromethyl, amino, alkylamino as defined above for alkyl, dialkylamino as defined for alkyl, nitro, cyano, carboxy, SO$_3$H, CHO,

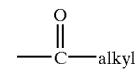

as defined above for alkyl,

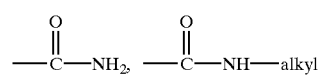

as defined above for alkyl,

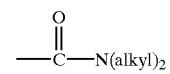

as defined above for alkyl, —(CH$_2$)$_n$—NH$_2$ wherein n is an integer of 1 to 5, —(CH$_2$)$_n$—NH-alkyl as defined above for alkyl and n, —(CH$_2$)$_n$—N(alkyl)$_2$ as defined above for alkyl and n.

The term "aralkyl" or "arylalkyl" means an aromatic radical attached to an alkyl radical wherein "aryl" and "alkyl" are as defined above, for example, benzyl, fluorenylmethyl, and the like.

The term "5- to 7-membered ring optionally containing an oxygen atom or N—R$^4$" includes, for example, pyrrolidine, pyrrazolidine, imidazolidine, oxazolidine, piperidine, piperazine, morpholine, homopiperidine, and the like. The carbon atoms of the above 5- to 7-membered ring may be substituted independently by alkyl, amino, aminoalkyl, monoalkylaminoalkyl, dialkylaminoalkyl, carboxy, carboxyalkyl, alkylcarboxyalkyl, thio, thioalkyl, alkylthioalkyl, hydroxy, hydroxyalkyl, alkoxy, or alkoxyalkyl.

In the compounds of Formula I or II, any unsubstituted carbon atoms of a bicyclic or tricyclic heteroaromatic moiety at R$^1$ or R$^{1a}$ may be substituted by R$^3$, R$^{3a}$, or R$^{3b}$.

"Halogen" is fluorine, chlorine, bromine, or iodine.

Some of the compounds of Formula I or II are capable of further forming both pharmaceutically acceptable acid addition and/or base salts. All of these forms are within the scope of the present invention.

Pharmaceutically acceptable acid addition salts of the compounds of Formula I or II include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al, "Pharmaceutical Salts," *J. of Pharma Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M. et al., "Pharmaceutical Salts," *J. of Pharma Sci.*, 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

A preferred compound of Formula I in the first aspect of the present invention is one wherein A is selected from the group consisting of:

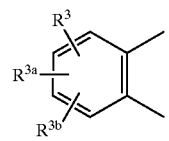

wherein $R^3$, $R^{3a}$, and $R^{3b}$ are each independently the same or different and are hydrogen,
  alkyl,
  aryl,
  heteroaryl,
  —$OR^4$ wherein $R^4$ is hydrogen,
    alkyl,
    aryl,
    aralkyl,
    acetyl, or

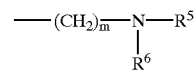

wherein $R^5$ and $R^6$ are each the same or different and are hydrogen,
    alkyl, cycloalkyl, acetyl, or
    $R^5$ and $R^6$ are taken together to form a 5- to 7-membered ring optionally containing an oxygen atom or N—$R^4$ wherein $R^4$ is as defined above and m is an integer of 2 to 5,

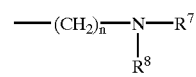

wherein n is zero or an integer of 1 and $R^7$ and $R^8$ are each independently the same or different and are hydrogen,
  alkyl,
  aryl,
  aralkyl,
  acetyl, or

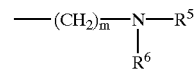

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

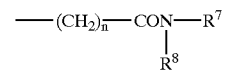

wherein $R^7$, $R^8$, and n are as defined above,

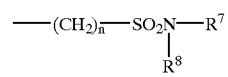

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above, —CH$_2$OR$^4$ wherein R$^4$ is as defined above,
halogen,
CF$_3$,
CBr$_3$,
CCl$_3$, or
NO$_2$,

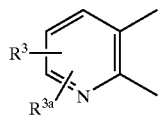

wherein R$^3$ and R$^{3a}$ are as defined above,

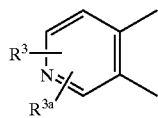

wherein R$^3$ and R$^{3a}$ are as defined above,

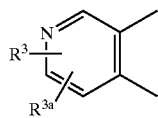

wherein R$^3$ and R$^{3a}$ are as defined above, or

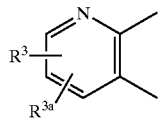

wherein R$^3$ and R$^{3a}$ are as defined above;

R$^1$ is 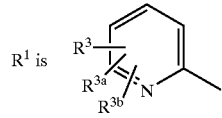

wherein R$^3$, R$^{3a}$ and R$^{3b}$ are as defined above,

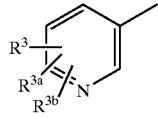

wherein R$^3$, R$^{3a}$ and R$^{3b}$ are as defined above,

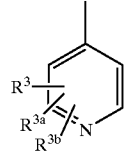

wherein R$^3$, R$^{3a}$, and R$^{3b}$ are as defined above,

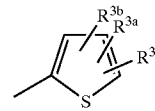

wherein R$^3$, R$^{3a}$, and R$^{3b}$ are as defined above,

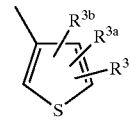

wherein R$^3$, R$^{3a}$, and R$^{3b}$ are as defined above,

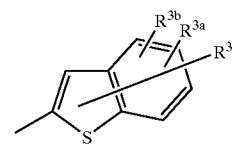

wherein R$^3$, R$^{3a}$, and R$^{3b}$ are as defined above,

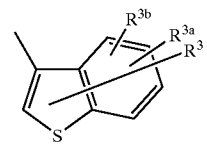

wherein R$^3$, R$^{3a}$, and R$^{3b}$ are as defined above,

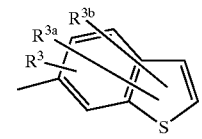

wherein R$^3$, R$^{3a}$, and R$^{3b}$ are as defined above,

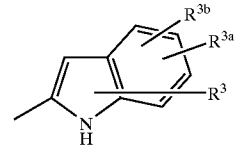

wherein R$^3$, R$^{3a}$, and R$^{3b}$ are as defined above,

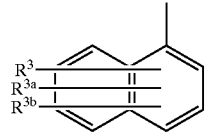

wherein $R^3$, $R^{3a}$, and $R^{3b}$ are as defined above,

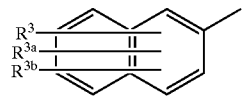

wherein $R^3$, $R^{3a}$, and $R^{3b}$ are as defined above,

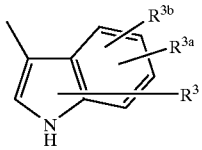

wherein $R^3$, $R^{3a}$, and $R^{3b}$ are as defined above,

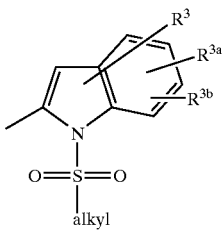

wherein $R^3$, $R^{3a}$, and $R^{3b}$ are as defined above,

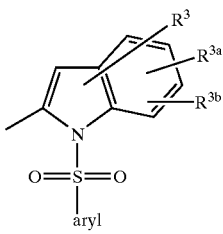

wherein $R^3$, $R^{3a}$, and $R^{3b}$ are as defined above,

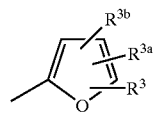

wherein $R^3$, $R^{3a}$, and $R^{3b}$ are as defined above,

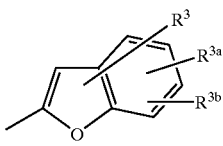

wherein $R^3$, $R^{3a}$, and $R^{3b}$ are as defined above,

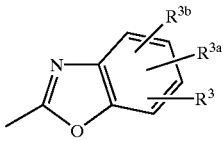

wherein $R^3$, $R^{3a}$, and $R^{3b}$ are as defined above,

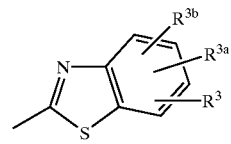

wherein $R^3$, $R^{3a}$, and $R^{3b}$ are as defined above,

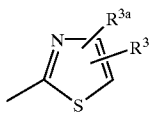

wherein $R^3$ and $R^{3a}$ are as defined above,

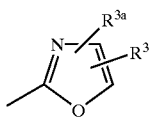

wherein $R^3$ and $R^{3a}$ are as defined above, halogen, or alkoxy; and $R^2$ is $CF_3$,
$CCl_3$,
$CBr_3$, or

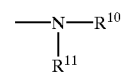

wherein $R^{10}$ is hydrogen and $R^{11}$ is 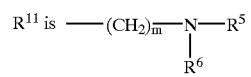

wherein m, $R^5$, and $R^6$ are as defined above, or

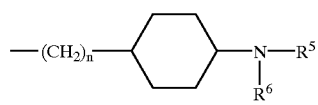

wherein n, $R^5$, and $R^6$ are as defined above.

A more preferred compound of Formula I in the first aspect of the present invention is one wherein A is

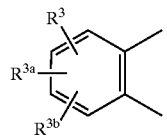

wherein $R^3$, $R^{3a}$, and $R^{3b}$ are each independently the same or different and are hydrogen,
  alkyl,
  aryl,
  heteroaryl,
  —$OR^4$ wherein $R^4$ is hydrogen,
    alkyl,
    aryl, aralkyl,
acetyl, or

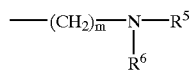

wherein $R^5$ and $R^6$ are each the same or different and are hydrogen, alkyl, cycloalkyl, acetyl, or
$R^5$ and $R^6$ are taken together to form a 5- to 7-membered ring optionally containing an oxygen atom or N—$R^4$ wherein $R^4$ is as defined above and m is an integer of 2 to 5,

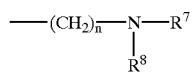

wherein n is zero or an integer of 1 and $R^7$ and $R^8$ are each independently the same or different and are
hydrogen,
alkyl,
aryl,
aralkyl,
acetyl, or

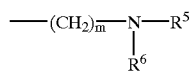

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

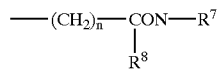

wherein $R^7$, $R^8$, and n are as defined above,

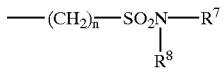

wherein $R^7$, $R^8$, and n are as defined above,
—(CH$_2$)$_n$—SO$_2$OR$^4$ wherein $R^4$ and n are as defined above,
—(CH$_2$)$_n$—CO$_2$R$^4$ wherein $R^4$ and n are as defined above,
—CH$_2$OR$^4$ wherein $R^4$ is as defined above,
halogen,
CF$_3$,
CBr$_3$,
CCl$_3$, or
NO$_2$;

$R^1$ is 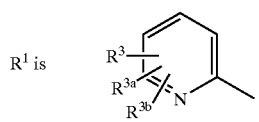

wherein $R^3$, $R^{3a}$, and $R^{3b}$ are as defined above,

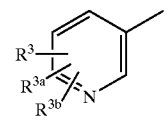

wherein $R^3$, $R^{3a}$, and $R^{3b}$ are as defined above,

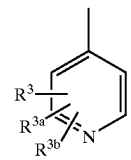

wherein $R^3$, $R^{3a}$, and $R^{3b}$ are as defined above,

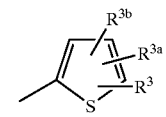

wherein $R^3$, $R^{3a}$, and $R^{3b}$ are as defined above,

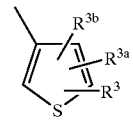

wherein $R^3$, $R^{3a}$, and $R^{3b}$ are as defined above,

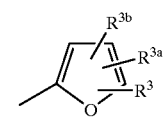

wherein $R^3$, $R^{3a}$, and $R^{3b}$ are as defined above,

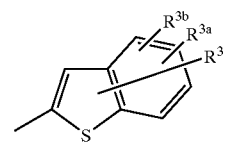

wherein $R^3$, $R^{3a}$, and $R^{3b}$ are as defined above,

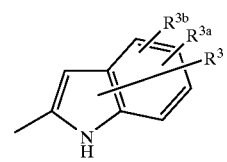

wherein $R^3$, $R^{3a}$, and $R^{3b}$ are as defined above,

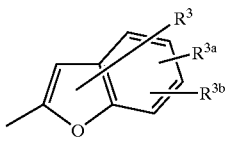

wherein $R^3$, $R^{3a}$, and $R^{3b}$ are as defined above, or

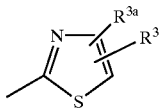

wherein $R^3$ and $R^{3a}$ are as defined above; and
$R^2$ is $CF_3$,
$CCl_3$,
$CBr_3$, or

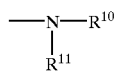

wherein $R^{10}$ is hydrogen and $R^{11}$ is 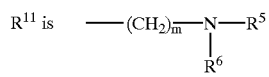

wherein m, $R^5$, and $R^6$ are as defined above, or

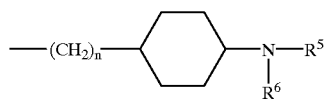

wherein n, $R^5$, and $R^6$ are as defined above.

Another more preferred compound of Formula I in the first aspect of the present invention is one wherein A is

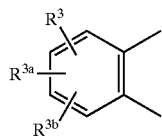

wherein $R^3$, $R^{3a}$, and $R^{3b}$ are each independently the same or different and are hydrogen,
alkyl,
aryl,
heteroaryl,
—$OR^4$ wherein $R^4$ is hydrogen,
  alkyl,
  aryl,
  heteroaryl,
  aralkyl,
  acetyl, or

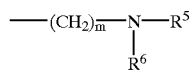

wherein $R^5$ and $R^6$ are each the same or different and are hydrogen, alkyl, cycloalkyl, acetyl, or $R^5$ and $R^6$ are taken together to form a 5- to 7-membered ring optionally containing an oxygen atom or N—$R^4$ wherein $R^4$ is as defined above and m is an integer of 2 to 5,

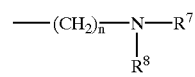

wherein n is zero or an integer of 1 and $R^7$ and $R^8$ are each independently the same or different and are hydrogen,
alkyl,
aryl,
aralkyl,
acetyl, or

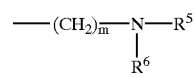

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

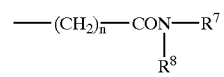

wherein $R^7$, $R^8$, and n are as defined above,

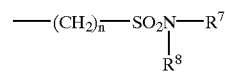

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$;

$R^1$ is 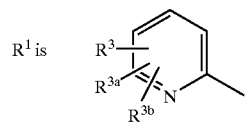

wherein $R^3$, $R^{3a}$, and $R^{3b}$ are as defined above,

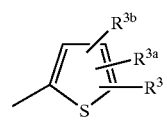

wherein $R^3$, $R^{3a}$, and $R^{3b}$ are as defined above,

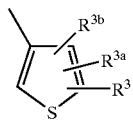

wherein $R^3$, $R^{3a}$, and $R^{3b}$ are as defined above,

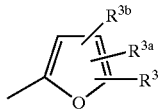

wherein $R^3$, $R^{3a}$, and $R^{3b}$ are as defined above,

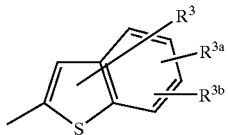

wherein $R^3$, $R^{3a}$, and $R^{3b}$ are as defined above,

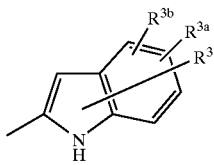

wherein $R^3$, $R^{3a}$, and $R^{3b}$ are as defined above,

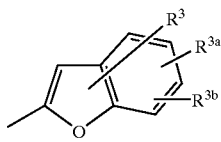

wherein $R^3$, $R^{3a}$, and $R^{3b}$ are as defined above, or

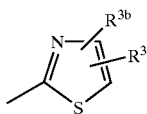

wherein $R^3$ and $R^{3a}$ are as defined above; and
$R^2$ is $CF_3$,
  $CCl_3$,
  $CBr_3$, or

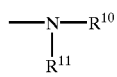

wherein $R^{10}$ is hydrogen and $R^{11}$ is 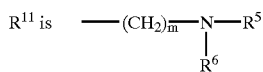

wherein m, $R^5$, and $R^6$ are as defined above, or

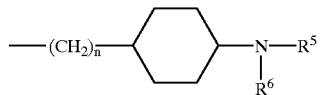

wherein n, $R^5$, and $R^6$ are as defined above.

A most preferred compound of Formula I in the first aspect of the present invention is one wherein A is

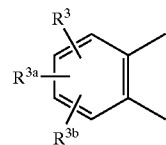

wherein $R^3$, $R^{3a}$, and $R^{3b}$ are each independently the same or different and are hydrogen, alkyl,
aryl,
heteroaryl,
—$OR^4$ wherein $R^4$ is hydrogen,
  alkyl,
  aryl,
  aralkyl,
  acetyl, or

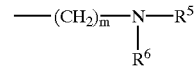

wherein
$R^5$ and $R^6$ are each the same or different and are hydrogen, alkyl, cycloalkyl, acetyl, or $R^5$ and $R^6$ are taken together to form a 5- to 7-membered ring optionally containing an oxygen atom or N—$R^4$ wherein $R^4$ is as defined above and m is an integer of 2 to 5,

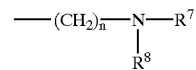

wherein n is zero or an integer of 1 and $R^7$ and $R^8$ are each independently the same or different and are hydrogen,
alkyl,
aryl,
aralkyl,
acetyl, or

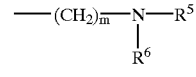

wherein $R^5$ and $R^6$ are as defined above or $R^7$ and $R^8$ taken together to form a 5- to 7-membered ring optionally containing an oxygen atom or N—$R^4$ wherein $R^4$ an m are as defined above,

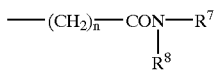

wherein $R^7$, $R^8$, and n are as defined above,

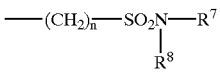

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$;

$R^1$ is 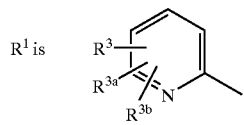

wherein $R^3$, $R^{3a}$, and $R^{3b}$ are as defined above,

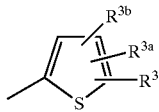

wherein $R^3$, $R^{3a}$, and $R^{3b}$ are as defined above,

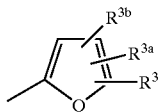

wherein $R^3$, $R^{3a}$, and $R^{3b}$ are as defined above,

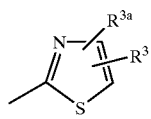

wherein $R^3$, and $R^{3a}$ are as defined above,

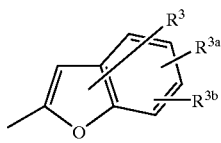

wherein $R^3$, $R^{3a}$, and $R^{3b}$ are as defined above, or

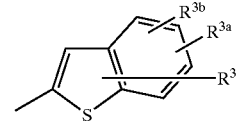

wherein $R^3$, $R^{3a}$, and $R^{3b}$ are as defined above; and $R^2$ is 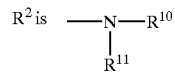

wherein $R^{10}$ is hydrogen and $R^{11}$ is 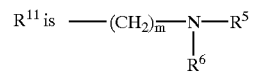

wherein m, $R^5$, and $R^6$ are as defined above, or

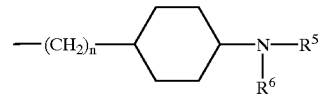

wherein n, $R^5$, $R^6$ are as defined above.

Particularly valuable in the first aspect of the present invention is a compound selected from the group consisting of:

N-(1-Azabicyclo[2.2.2]octan-3-yl)-3-(2-pyridinyl)-2-quinoxalinamine;

N-[3-(1H-Imidazol-1-yl)propyl]-3-(2-pyridinyl)-2-quinoxalinamine;

N-[2-(1-Methyl-2-pyrrolidinyl)ethyl]-3-(2-pyridinyl)-2-quinoxalinamine;

1-[3-[[3-Pyridinyl)-2-quinoxalinamine]amino]propyl]-2-pyrrolidinone;

N-[4-(4-Morpholinyl)phenyl]-3-(2-pyridinyl)-2-quinoxalinamine;

N-(4-Piperidinylmethyl)-3-(2-pyridinyl)-2-quinoxalinamine;

N-[4-(Dimethylamino)phenyl]-3-(2-pyridinyl)-2-quinoxalinamine;

N-Methyl-N-[4-[[3-(2-pyridinyl)-2-quinoxalinyl]amino]phenyl]-acetamide;

N-(6,7-Dichloro-3-pyridin-2-yl-quinoxalin-2-yl)-N',N'-dimethylcyclohexane-1,4-diamine;

N-(6,7-Dichloro-3-pyridin-2-yl-quinoxalin-2-yl) cyclohexane-1,4-diamine;

2-[1,4']Bipiperidinyl-1'-yl-6,7-dichloro-3-pyridin-2-yl-quinoxaline;

(6,7-Dichloro-3-pyridin-2-yl-quinoxalin-2-yl)-(4-diethylaminomethylphenyl)-amine;

N'-(6,7-Dichloro-3-furan-2-yl-quinoxalin-2-yl)-N,N-dimethyl-propane-1,3-diamine;

N'-(6,7-Dichloro-3-thiophen-2-yl-quinoxalin-2-yl)-N,N-dimethyl-propane-1,3-diamine;

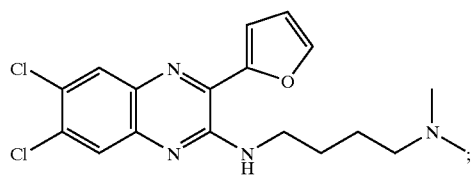
N'-(6,7-Difluoro-3-thiophen-2-yl-quinoxalin-2-yl)-N,N-dimethyl-butane-1,4-diamine;
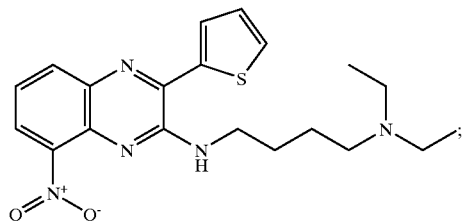
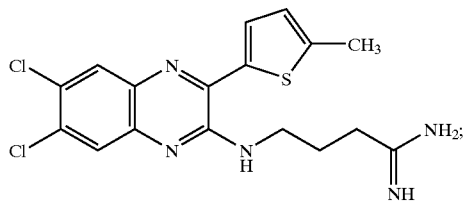
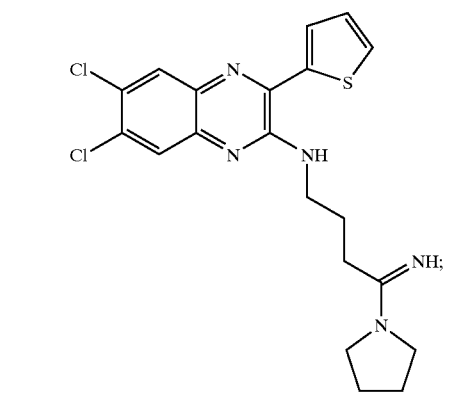
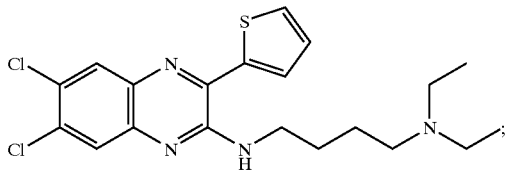
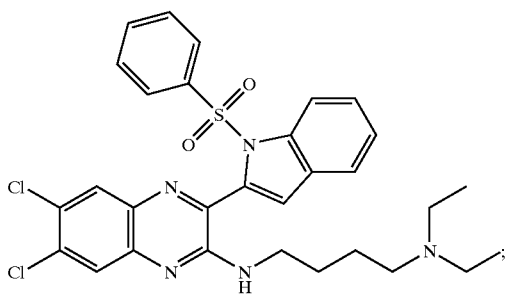
N'-[6,7-Dichloro-3-(1H-indol-2-yl)-quinoxalin-2-yl]-N,N-diethyl-butane-1,4-diamine;
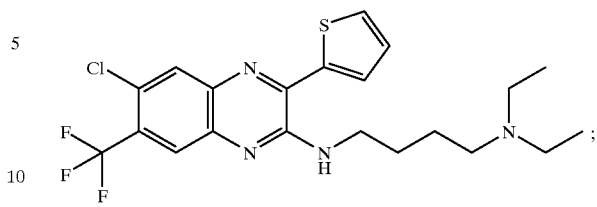
N'-(3-Benzo[b]thiophen-2-yl-6,7-dichloro-quinoxalin-2-yl)-N,N-diethyl-butane-1,4-diamine;
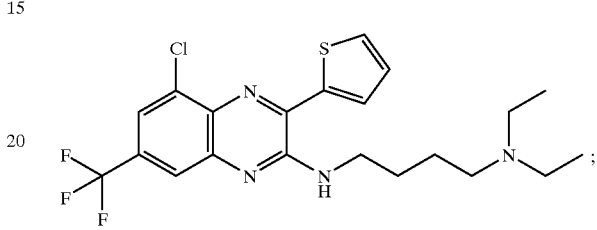
N,N-Diethyl-N'-(3-thiophen-2-yl-7-trifluoromethyl-quinoxalin-2-yl)-butane-1,4-diamine;
N'-[6,7-Dichloro-3-(5-methyl-thiophen-2-yl)-quinoxalin-2-yl]-N,N-diethyl-butane-1,4-diamine;
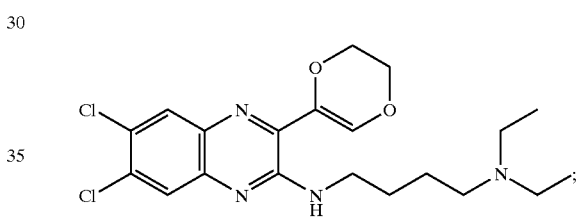
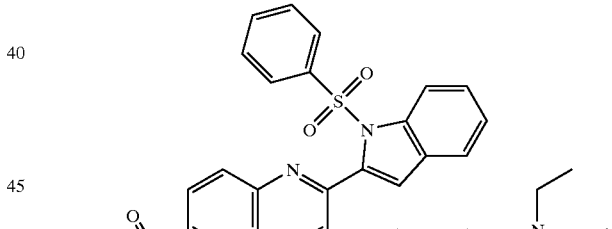
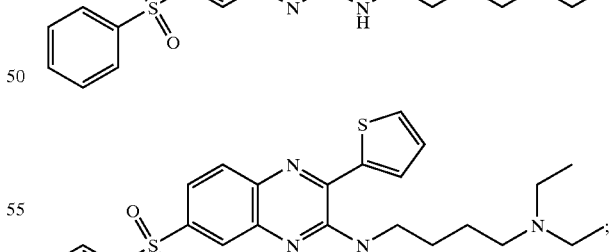
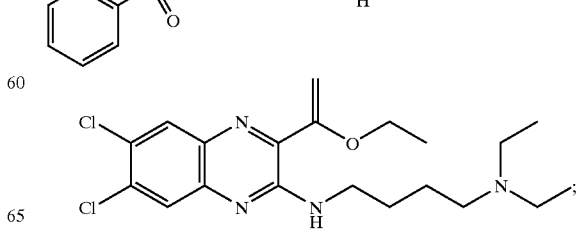

N'-(6,7-Dichloro-3-thiazol-2-yl-quinoxalin-2-yl)-N,N-dimethyl-propane-1,3-diamine;
N'-(3-[2,2']Bithiophenyl-5-yl-6,7-dichloro-quinoxalin-2-yl)-N,N-diethyl-butane-1,4-diamine;
N'-[6,7-Dichloro-3-(5-chloro-thiophen-2-yl)-quinoxalin-2-yl]-N,N-diethyl-butane-1,4-diamine;
N'-[6,7-Dichloro-3-(5-methoxy-thiophen-2-yl)-quinoxalin-2-yl]-N,N-diethyl-butane-1,4-diamine;
N'-[6,7-Dichloro-3-(5-propyl-thiophen-2-yl)-quinoxalin-2-yl]-N,N-diethyl-butane-1,4-diamine;
N'-(3-Benzofuran-2-yl-6,7-dichloro-quinoxalin-2-yl)-N,N-diethyl-butane-1,4-diamine;

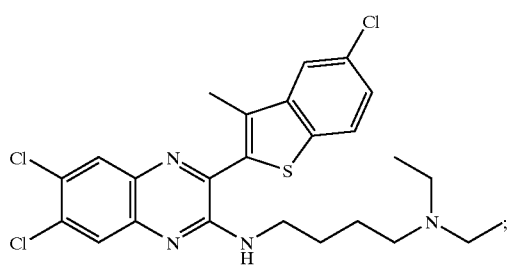

N'-[6,7-Dichloro-3-dibenzothiophen-4-yl-quinoxalin-2-yl)-N,N-diethyl-butane-1,4-diamine;

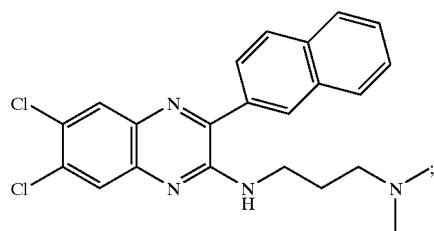

[6,7-Dichloro-3-(5-phenyl-oxazol-2-yl)-quinoxalin-2-yl]-(4-pyrrolidin-1-yl-butyl)-amine;
[6,7-Dichloro-3-(5-thiophen-2-yl-oxazol)-quinoxalin-2-yl]-(4-pyrrolidin-1-yl-butyl)-amine;

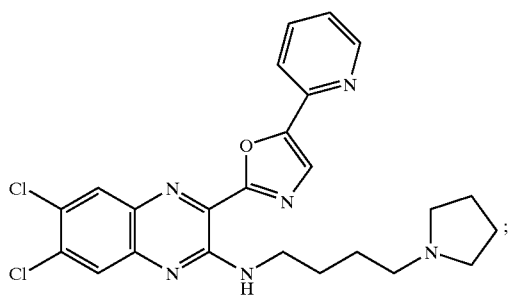

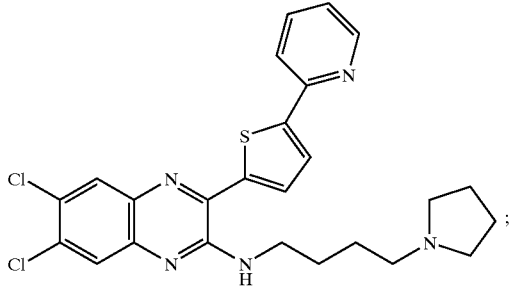

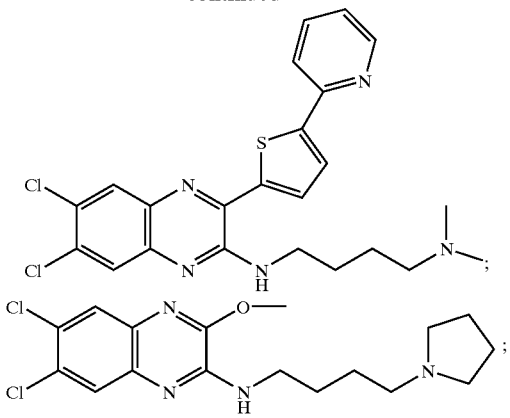

N-(6,7-Dichloro-3-pyridin-3-yl-quinoxalin-2-yl)-N',N'-dimethyl-cyclohexane-1,4-diamine;
N-(6,7-Dichloro-3-pyridin-4-yl-quinoxalin-2-yl)-N',N'-dimethyl-cyclohexane-1,4-diamine;
N-(6,7-Dimethoxy-3-pyridin-2-yl-quinoxalin-2-yl)-N',N'-dimethyl-cyclohexane-1,4-diamine;
N,N-Dimethyl-N'-(3-pyridin-2-yl-7,8-dihydro-6H-cyclopenta[g]quinoxalin-2-yl)-cyclohexane-1,4-diamine;
N'-(6,7-Dichloro-3-pyridin-2-yl-quinoxalin-2-yl)-N,N-dimethyl-ethane-1,2-diamine;
N'-(6,7-Dichloro-3-pyridin-2-yl-quinoxalin-2-yl)-N,N-dimethyl-propane-1,3-diamine;
N'-(6,7-Dichloro-3-pyridin-2-yl-quinoxalin-2-yl)-N,N-dimethyl-butane-1,4-diamine;
N'-(6,7-Dichloro-3-pyridin-2-yl-quinoxalin-2-yl)-N,N-dimethyl-pentane-1,5-diamine;
N-(6,7-Dichloro-3-pyridin-2-yl-quinoxalin-2-yl)-pentane-1,5-diamine;
N-(6,7-Dichloro-3-pyridin-2-yl-quinoxalin-2-yl)-N,N-dimethyl-hexane-1,6-diamine;
[3-(6,7-Dichloro-3-pyridin-2-yl-quinoxalin-2-ylsulfanyl)-propyl]-dimethylamine;
(6,7-Dichloro-3-pyridin-2-yl-quinoxalin-2-yl)-(3-morpholin4-yl-propyl)-amine;
(6,7-Dichloro-3-pyridin-2-yl-quinoxalin-2-yl)-(3-methoxypropyl)-amine;
N'-1-[3-(6,7-Dichloro-3-pyridin-2-yl-quinoxalin-2-ylamino)-propyl]-N'-1-methyl-propane-1,3-diamine;
2-{[3-(6,7-Dichloro-3-pyridin-2-yl-quinoxalin-2-ylamino)-propyl]-(2-hydroxy-ethyl)-amino}-ethanol;
{4-[4-(2-Chloro-phenyl)-piperidin-1-yl]-butyl-(6,7-dichloro-3-pyridin-2-yl-quinoxalin-2-yl)}amine;
(6,7-Dichloro-3-pyridin-2-yl-quinoxalin-2-yl)-(1-phenyl-4-piperidin-1-yl-butyl)-amine;
[6,7-Dichloro-3-(1-ethyl-5-phenyl-imidazol-2-yl)-quinoxalin-2-yl]-(4-pyrrolidin-1-yl-butyl)-amine;
[6,7-Dichloro-3-(1-phenyl-imidazol-2-yl)-quinoxalin-2-yl]-(4-pyrrolidin-1-yl-butyl)-amine;
[6,7-Dichloro-3-[1-ethyl-5-(5-methyl-thiophene-2-yl)-imidazol-5-yl]-quinoxalin-2-yl]-(4-pyrrolidin-1-yl-butyl)-amine; and
[6,7-Dichloro-3-(1-phenyl-pyrazolo-5-yl)-quinoxalin-2-yl]-(4-pyrrolidin-1-yl-butyl)-amine;
or a pharmaceutically acceptable salt thereof.

A preferred compound of Formula II in the second aspect of the present invention is one wherein A is selected from the group consisting of:

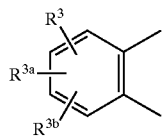

wherein $R^3$, $R^{3a}$, and $R^{3b}$ are each independently the same or different and are hydrogen,
alkyl,
aryl,
heteroaryl,
—$OR^4$ wherein $R^4$ is hydrogen,
  alkyl,
  aryl,
  aralkyl,
  acetyl, or

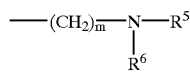

wherein
  $R^5$ and $R^6$ are each the same or different and are hydrogen, alkyl, cycloalkyl, acetyl, or $R^5$ and $R^6$ are taken together to form a 5- to 7-membered ring optionally containing an oxygen atom or N—$R^4$ wherein $R^4$ is as defined above and m is an integer of 2 to 5,

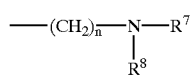

wherein n is zero or an integer of 1 and $R^7$ and $R^8$ are each independently the same or different and are hydrogen,
alkyl,
aryl,
aralkyl,
acetyl, or

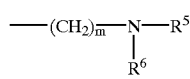

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

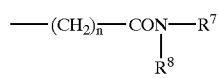

wherein $R^7$, $R^8$, and n are as defined above,

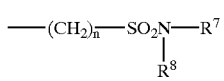

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$,

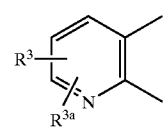

wherein $R^3$ and $R^{3a}$ are as defined above,

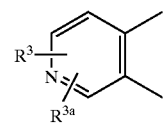

wherein $R^3$ and $R^{3a}$ are as defined above,

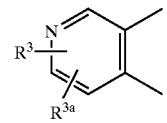

wherein $R^3$ and $R^{3a}$ are as defined above, or

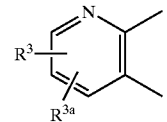

wherein $R^3$ and $R^{3a}$ are as defined above;

$R^{1a}$ is 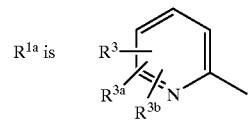

wherein $R^3$, $R^{3a}$, and $R^{3b}$ are as defined above,

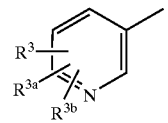

wherein $R^3$, $R^{3a}$, and $R^{3b}$ are as defined above,

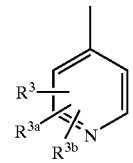

wherein $R^3$, $R^{3a}$, and $R^{3b}$ are as defined above,

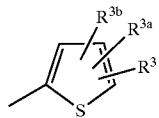

wherein $R^3$, $R^{3a}$, and $R^{3b}$ are as defined above,

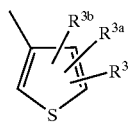

wherein $R^3$, $R^{3a}$, and $R^{3b}$ are as defined above,

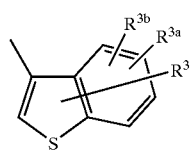

wherein $R^3$, $R^{3a}$, and $R^{3b}$ are as defined above,

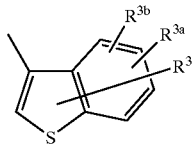

wherein $R^3$, $R^{3a}$, and $R^{3b}$ are as defined above,

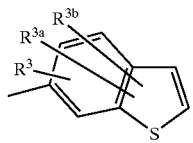

wherein $R^3$, $R^{3a}$, and $R^{3b}$ are as defined above,

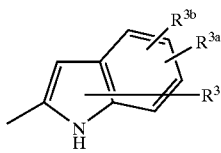

wherein $R^3$, $R^{3a}$, and $R^{3b}$ are as defined above,

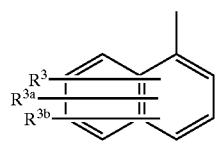

wherein $R^3$, $R^{3a}$, an $R^{3b}$ are as defined above,

wherein $R^3$, $R^{3a}$, and $R^{3b}$ are as defined above,

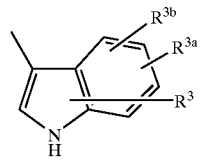

wherein $R^3$, $R^{3a}$, and $R^{3b}$ are as defined above,

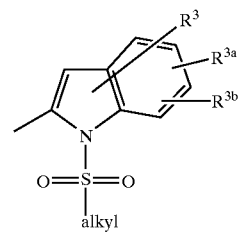

wherein $R^3$, $R^{3a}$, and $R^{3b}$ are as defined above,

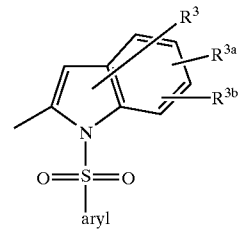

wherein $R^3$, $R^{3a}$, and $R^{3b}$ are as defined above,

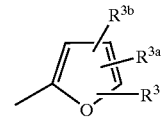

wherein $R^3$, $R^{3a}$, and $R^{3b}$ are as defined above,

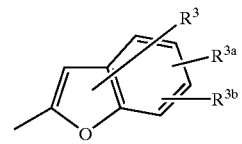

wherein $R^3$, $R^{3a}$, and $R^{3b}$ are as defined above,

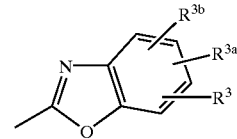

wherein $R^3$, $R^{3a}$, and $R^{3b}$ are as defined above,

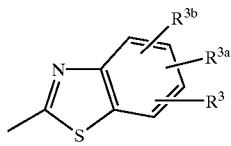

wherein $R^3$, $R^{3a}$, and $R^{3b}$ are as defined above,

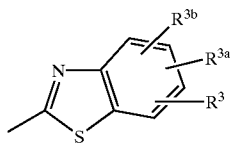

wherein $R^3$, $R^{3a}$, and $R^{3b}$ are as defined above,

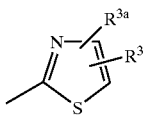

wherein $R^3$ and $R^{3a}$ are as defined above,

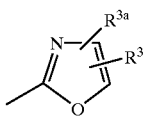

wherein $R^3$ and $R^{3a}$ are as defined above,
halogen, or
alkoxy; and $R^{2a}$ is $CF_3$,
$CCl_3$,
$CBr_3$, or

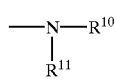

wherein $R^{10}$ is hydrogen and $R^{11}$ is 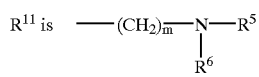

wherein m, $R^5$, and $R^6$ are as defined above, or

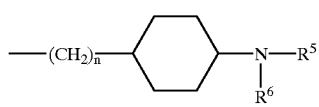

wherein n, $R^5$, and $R^6$ are as defined above.

A more preferred compound of Formula II in the second aspect of the present invention is one wherein A is

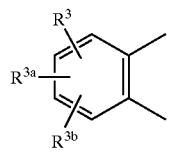

wherein $R^3$, $R^{3a}$, and $R^{3b}$ are each independently the same or different and are hydrogen,
alkyl,
aryl,
heteroaryl,
—$OR^4$ wherein $R^4$ is hydrogen,
alkyl,
aryl,
aralkyl,
acetyl, or

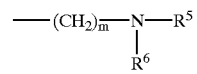

wherein
$R^5$ and $R^6$ are each the same or different and are hydrogen, alkyl, cycloalkyl, acetyl, or $R^5$ and $R^6$ are taken together to form a 5- to 7-membered ring optionally containing an oxygen atom or N—$R^4$ wherein $R^4$ is as defined above and m is an integer of 2 to 5,

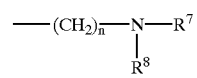

wherein n is zero or an integer of 1 and $R^7$ and $R^8$ are each independently the same or different and are hydrogen,
alkyl,
aryl,
aralkyl,
acetyl, or

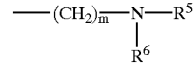

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

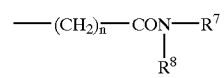

wherein $R^7$, $R^8$, and n are as defined above,

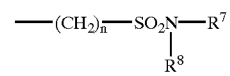

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above, —$CH_2OR^4$ wherein $R^4$ is as defined above,
halogen,
$CF_3$,
$CBr_3$,
$CCl_3$, or
$NO_2$;

$R^{1a}$ is 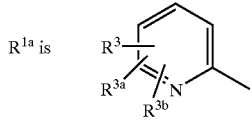

wherein $R^3$, $R^{3a}$, and $R^{3b}$ are as defined above,

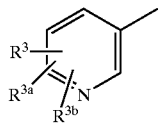

wherein $R^3$, $R^{3a}$, and $R^{3b}$ are as defined above,

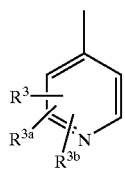

wherein $R^3$, $R^{3a}$, and $R^{3b}$ are as defined above,

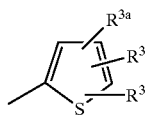

wherein $R^3$, $R^{3a}$, and $R^{3b}$ are as defined above,

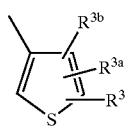

wherein $R^3$, $R^{3a}$, and $R^{3b}$ are as defined above,

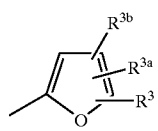

wherein $R^3$, $R^{3a}$, and $R^{3b}$ are as defined above,

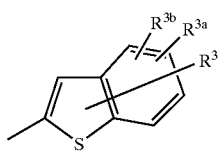

wherein $R^3$, $R^{3a}$, and $R^{3b}$ are as defined above,

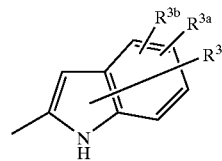

wherein $R^3$, $R^{3a}$, and $R^{3b}$ are as defined above,

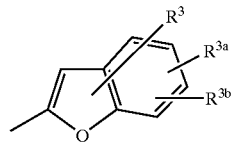

wherein $R^3$, $R^{3a}$, and $R^{3b}$ are as defined above, or

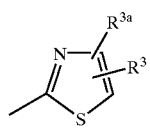

wherein $R^3$ and $R^{3a}$ are as defined above; and
$R^{2a}$ is $CF_3$,
$CCl_3$,
$CBr_3$, or

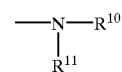

wherein $R^{10}$ is hydrogen and $R^{11}$ is 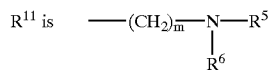

wherein m, $R^5$, $R^6$ are as defined above, or

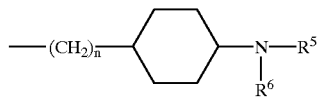

wherein n, $R^5$, $R^6$ are as defined above.

Another more preferred compound of Formula II in the second aspect of the present invention is one wherein A is 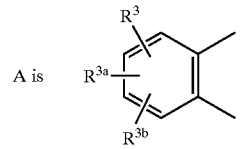

wherein $R^3$, $R^{3a}$, and $R^{3b}$ are each independently the same or different and are hydrogen,
alkyl,
aryl,
heteroaryl,
—$OR^4$ wherein $R^4$ is hydrogen,
alkyl,
aryl, aralkyl,
acetyl, or

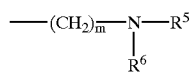

wherein
$R^5$ and $R^6$ are each the same or different and are hydrogen, alkyl, cycloalkyl, acetyl, or $R^5$ and $R^6$ are taken together to form a 5- to 7-membered ring optionally containing an oxygen atom or N—$R^4$ wherein $R^4$ is as defined above and m is an integer of 2 to 5,

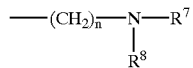

wherein n is zero or an integer of 1 and $R^7$ and $R^8$ are each independently the same or different and are hydrogen,
alkyl,
aryl,
aralkyl,
acetyl, or

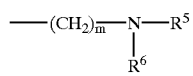

wherein $R^5$ and $R^6$ are as defined above or
$R^7$ and $R^8$ taken together to form a 5- to 7-membered ring optionally containing an oxygen atom or N—$R^4$ wherein $R^4$ and m are is as defined above,

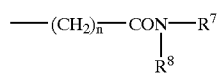

wherein $R^7$, $R^8$, and n are as defined above,

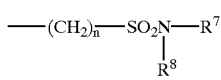

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$;

$R^{1a}$ is 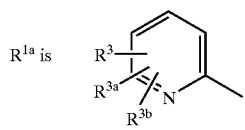

wherein $R^3$, $R^{3a}$, and $R^{3b}$ are as defined above,

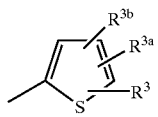

wherein $R^3$, $R^{3a}$, and $R^{3b}$ are as defined above,

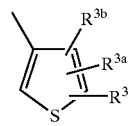

wherein $R^3$, $R^{3a}$, and $R^{3b}$ are as defined above,

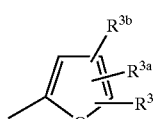

wherein $R^3$, $R^{3a}$, and $R^{3b}$ ere defined above,

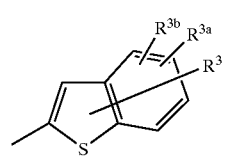

wherein $R^3$, $R^{3a}$, and $R^{3b}$ are as defined above,

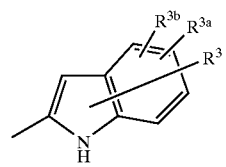

wherein $R^3$, $R^{3a}$, and $R^{3b}$ are as defined above, or

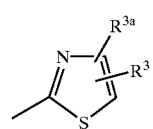

wherein $R^3$ and $R^{3a}$ are as defined above; and
$R^{2a}$ is $CF_3$,
$CCl_3$,
$CBr_3$, or

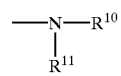

wherein $R^{10}$ is hydrogen and $R^{11}$ is 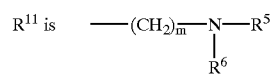

wherein m, $R^5$, and $R^6$ are as defined above, or

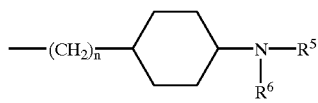

wherein n, $R^5$, and $R^6$ are as defined above.

A most preferred compound of Formula II in the second aspect of the present invention is one wherein A is 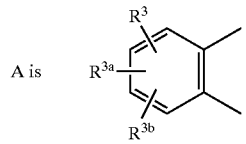

wherein $R^3$, $R^{3a}$, and $R^{3b}$ are each independently the same or different and are hydrogen, alkyl,
aryl,
heteroaryl,
—$OR^4$ wherein $R^4$ is hydrogen,
  alkyl,
  aryl,
  aralkyl,
  acetyl, or

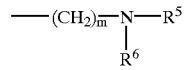

wherein
$R^5$ and $R^6$ are each the same or different and are hydrogen, alkyl, cycloalkyl, acetyl, or
$R^5$ and $R^6$ are taken together to form a 5- to 7-membered ring optionally containing an oxygen atom or N—$R^4$ wherein $R^4$ is as defined above and m is an integer of 2 to 5,

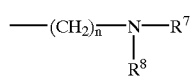

wherein n is zero or an integer of 1 and $R^7$ and $R^8$ are each independently the same or different and are hydrogen,
alkyl,
aryl,
aralkyl,
acetyl, or

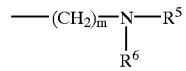

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

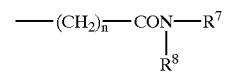

wherein $R^7$, $R^8$, and n are as defined above,

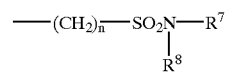

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$;

$R^{1a}$ is 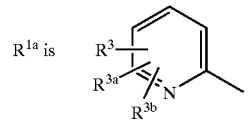

wherein $R^3$, $R^{3a}$, and $R^{3b}$ are as defined above,

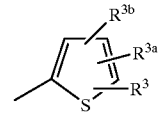

wherein $R^3$, $R^{3a}$, and $R^{3b}$ are as defined above,

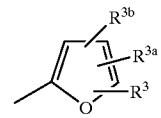

wherein $R^3$, $R^{3a}$, and $R^{3b}$ are as defined above,

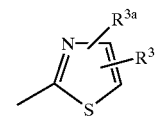

wherein $R^3$ and $R^{3a}$ are as defined above,

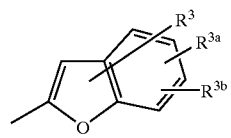

wherein R³, R³ᵃ, and R³ᵇ are as defined above, or

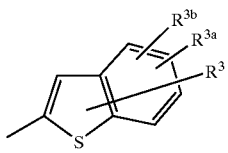

wherein R³, R³ᵃ, and R³ᵇ are as defined above; and

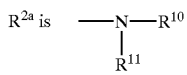

wherein R¹⁰ is hydrogen and

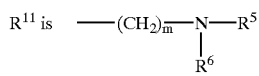

wherein m, R⁵, and R⁶ are as defined above, or

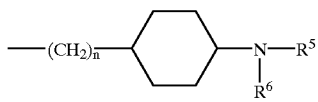

wherein n, R⁵, R⁶ are as defined above.

Particularly valuable in the second aspect of the present invention is a compound selected from the group consisting of:

N'-[6-Chloro-3-(2-pyridinyl)-2-quinoxalinyl]-N,N-diethyl-1,2-ethanediamine;
N'-[7-Chloro-3-(2-pyridinyl)-2-quinoxalinyl]-N,N-diethyl-1,2-ethanediamine;
N'-[6,7-Dichloro-3-(2-pyridinyl)-2-quinoxalinyl]-N,N-diethyl-1,2-ethanediamine;
6,7-Dichloro-3-(2-pyridinyl)-N-[3-(1-pyrrolidinyl)propyl]-2-quinoxalinamine;
6-Chloro-3-(2-pyridinyl)-N-[2-(1-pyrrolidinyl)ethyl]-2-quinoxalinamine;
7-Chloro-3-(2-pyridinyl)-N-[2-(1-pyrrolidinyl)ethyl]-2-quinoxalinamine;
N'-[6,7-Dimethyl-3-(2-pyridinyl)-2-quinoxalinyl]-N,N-diethyl-1,2-ethanediamine;
6-Chloro-3-(2-pyridinyl)-N-[3-(1-pyrrolidinyl)propyl]-2-quinoxalinamine;
7-Chloro-3-(2-pyridinyl)-N-[3-(1-pyrrolidinyl)propyl]-2-quinoxalinamine;
N'-[6,7-Dimethyl-3-(2-pyridinyl)-2-quinoxalinyl]-N,N-dimethyl-1,3-propanediamine;
N'-[6-Chloro-3-(2-pyridinyl)-2-quinoxalinyl]-N,N-dimethyl-1,3-propanediamine;
N'-[7-Chloro-3-(2-pyridinyl)-2-quinoxalinyl]-N,N-dimethyl-1,3-propanediamine;
6-Chloro-N-[4-(dimethylamino)cyclohexyl]-3-(2-pyridinyl)-2-quinoxalinamine;
7-Chloro-N-[4-(dimethylamino)cyclohexyl]-3-(2-pyridinyl)-2-quinoxalinamine;
2,6,7-Trimethyl-3-piperazin-1-yl-quinoxaline;
N,N-Dimethyl-N'-(3-methyl-quinoxalin-2-yl)-propane-1,3-diamine;
2-Methyl-3-(4-methyl-piperazin-1-yl)-quinoxaline;
2-Ethyl-3-piperazin-1-yl-quinoxaline;
6,7-Dichloro-2-methyl-3-piperazin-1-yl-quinoxaline;
2-Phenyl-3-piperidin-1-yl-quinoxaline;
Benzyl-(3-phenyl-quinoxalin-2-yl)-amine;
Phenyl-(3-phenyl-quinoxalin-2-yl)-amine;
Methyl-(3-phenyl-quinoxalin-2-yl)-amine;
3-Phenyl-quinoxalin-2-ylamine;
2-Methyl-3-piperazin-1-yl-quinoxaline;
2-Methyl-3-piperidino-quinoxaline;
5-[4-(3-Methyl-quinoxalin-2-yl)-piperazin-1-yl]-pentan-1-ol;
N,N-Dimethyl-N'-(3-methyl-quinoxalin-2-yl)-ethane-1,2-diamine;
N,N-Diethyl-N'-(3-methyl-quinoxalin-2-yl)-ethane-1,2-diamine;
(3-Methyl-quinoxalin-2-yl)-(3-morpholin-4-yl-propyl)-amine;
N,N-Dimethyl-N'-(3-phenyl-quinoxalin-2-yl)-propane-1,3-diamine;
3-Phenyl-quinoxalin-2-ylamine;
2-Methyl-3-pyrrolidin-1-yl-quinoxaline;
N-(1-Azabicyclo[2.2.2]octan-3-yl)-3-(2-pyridinyl)-2-quinoxalinamine;
N-[3-(1H-Imidazol-1-yl)propyl]-3-(2-pyridinyl)-2-quinoxalinamine;
N-[2-(1-Methyl-2-pyrrolidinyl)ethyl]-3-(2-pyridinyl)-2-quinoxalinamine;
1-[3-[[3-Pyridinyl)-2-quinoxalinamine]amino]propyl]-2-pyrrolidinone;
N-[4-(4-Morpholinyl)phenyl]-3-(2-pyridinyl)-2-quinoxalinamine;
N-(4-Piperidinylmethyl)-3-(2-pyridinyl)-2-quinoxalinamine;
N-[4-(Dimethylamino)phenyl]-3-(2-pyridinyl)-2-quinoxalinamine;
N-Methyl-N-[4-[[3-(2-pyridinyl)-2-quinoxalinyl]amino]phenyl]-acetamide;
N-(6,7-Dichloro-3-pyridin-2-yl-quinoxalin-2-yl)-N',N'-dimethylcyclohexane-1,4-diamine;
N-(6,7-Dichloro-3-pyridin-2-yl-quinoxalin-2-yl)-cyclohexane-1,4-diamine;
2-[1,4']Bipiperidinyl-1'-yl-6,7-dichloro-3-pyridin-2-yl-quinoxaline;
(6,7-Dichloro-3-pyridin-2-yl-quinoxalin-2-yl)-(4-diethylaminomethylphenyl)-amine;
N'-(6,7-Dichloro-3-furan-2-yl-quinoxalin-2-yl)-N,N-dimethyl-propane-1,3-diamine;
N'-(6,7-Dichloro-3-thiophen-2-yl-quinoxalin-2-yl)-N,N-dimethyl-propane-1,3-diamine;

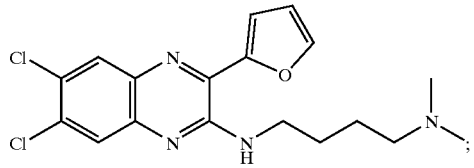

N'-(6,7-Difluoro-3-thiophen-2-yl-quinoxalin-2-yl)-N,N-dimethyl-butane-1,4-diamine;

N'-(3-Benzo[b]thiophen-2-yl-6,7-dichloro-quinoxalin-2-yl)-N,N-diethyl-butane-1,4-diamine;

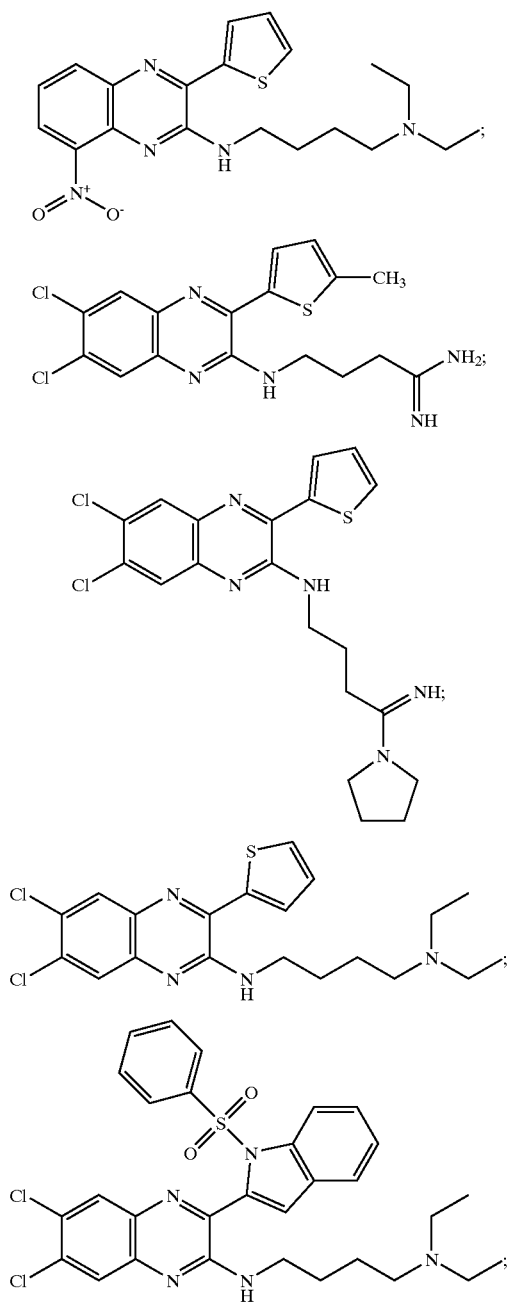

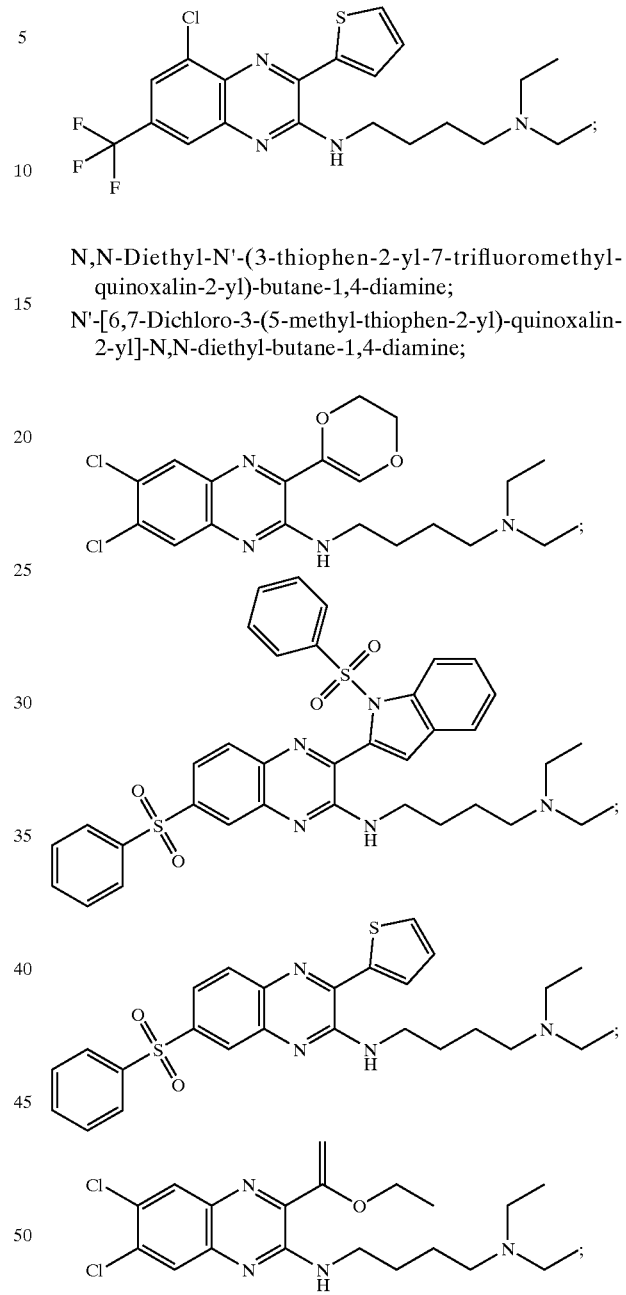

N,N-Diethyl-N'-(3-thiophen-2-yl-7-trifluoromethyl-quinoxalin-2-yl)-butane-1,4-diamine;

N'-[6,7-Dichloro-3-(5-methyl-thiophen-2-yl)-quinoxalin-2-yl]-N,N-diethyl-butane-1,4-diamine;

N'-[6,7-Dichloro-3-(1H-indol-2-yl)-quinoxalin-2-yl]-N,N-diethyl-butane-1,4-diamine;

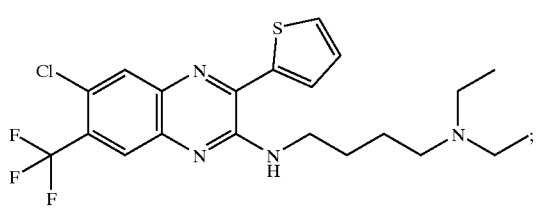

N'-(6,7-Dichloro-3-thiazol-2-yl-quinoxalin-2-yl)-N,N-dimethyl-propane-1,3-diamine;

N'-(3-[2,2']Bithiophenyl-5-yl-6,7-dichloro-quinoxalin-2-yl)-N,N-diethyl-butane-1,4-diamine;

N'-[6,7-Dichloro-3-(5-chloro-thiophen-2-yl)-quinoxalin-2-yl]-N,N-diethyl-butane-1,4-diamine;

N'-[6,7-Dichloro-3-(5-methoxy-thiophen-2-yl)-quinoxalin-2-yl]-N,N-diethyl-butane-1,4-diamine;

N'-[6,7-Dichloro-3-(5-propyl-thiophen-2-yl)-quinoxalin-2-yl]-N,N-diethyl-butane-1,4-diamine;

N'-(3-Benzofuran-2-yl-6,7-dichloro-quinoxalin-2-yl)-N,N-diethyl-butane-1,4-diamine;

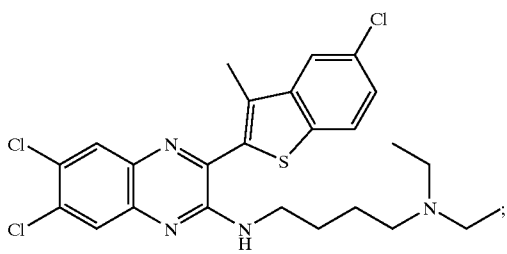

N'-[6,7-Dichloro-3-dibenzothiophen-4-quinoxalin-2-yl)-
N,N-diethyl-butane-1,4-diamine;

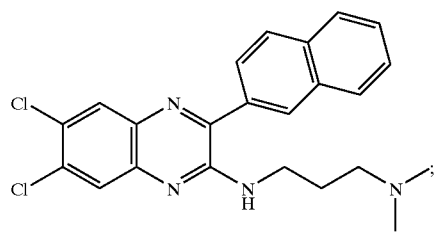

[6,7-Dichloro-3-(5-phenyl-oxazol-2-yl)-quinoxalin-2-
yl]-(4-pyrrolidin-1-yl-butyl)-amine;

[6,7-Dichloro-3-(5-thiophen-2-yl-oxazol)-quinoxalin-2-
yl]-(4-pyrrolidin-1-yl-butyl)-amine;

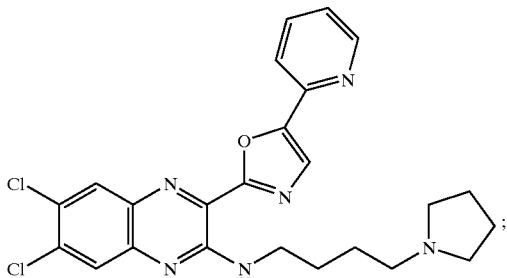

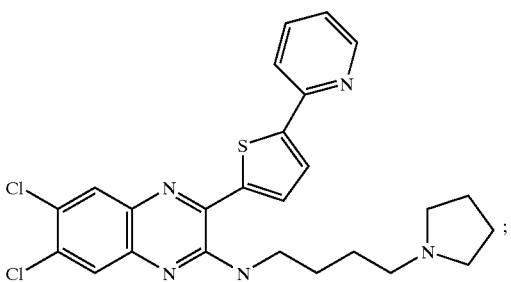

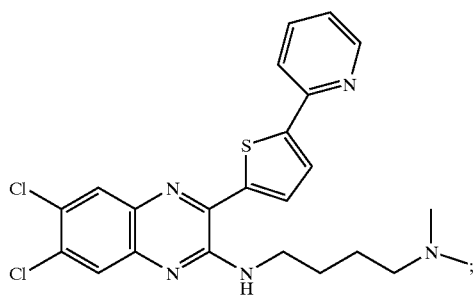

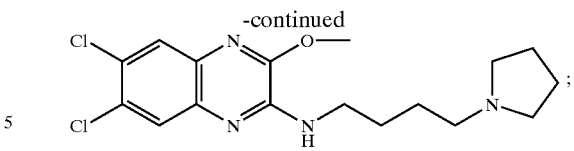

N-(6,7-Dichloro-3-pyridin-3-yl-quinoxalin-2-yl)-N',N'-
dimethylcyclohexane-1,4-diamine;

N-(6,7-Dichloro-3-pyridin-4-yl-quinoxalin-2-yl)-N',N'-
dimethylcyclohexane-1,4-diamine;

N-(6,7-Dimethoxy-3-pyridin-2-yl-quinoxalin-2-yl)-N',
N'-dimethylcyclohexane-1,4-diamine;

N,N-Dimethyl-N'-(3-pyridin-2-yl-7,8-dihydro-6H-
cyclopenta[g]quinoxalin-2-yl)-cyclohexane-1,4-
diamine;

N'-(6,7-Dichloro-3-pyridin-2-yl-quinoxalin-2-yl)-N,N-
dimethyl-ethane-1,2-diamine;

N'-(6,7-Dichloro-3-pyridin-2-yl-quinoxalin-2-yl)-N,N-
dimethyl-propane-1,3-diamine;

N'-(6,7-Dichloro-3-pyridin-2-yl-quinoxalin-2-yl)-N,N-
dimethyl-butane-1,4-diamine;

N'-(6,7-Dichloro-3-pyridin-2-yl-quinoxalin-2-yl)-N,N-
dimethyl-pentane-1,5-diamine;

N-(6,7-Dichloro-3-pyridin-2-yl-quinoxalin-2-yl)-
pentane-1,5-diamine;

N'-(6,7-Dichloro-3-pyridin-2-yl-quinoxalin-2-yl)-N,N-
dimethyl-hexane-1,6-diamine;

[3-(6,7-Dichloro-3-pyridin-2-yl-quinoxalin-2-
ylsulfanyl)-propyl]-dimethylamine;

(6,7-Dichloro-3-pyridin-2-yl-quinoxalin-2-yl)-(3-
morpholin-4-yl-propyl)-amine;

(6,7-Dichloro-3-pyridin-2-yl-quinoxalin-2-yl)-(3-
methoxypropyl)-amine;

N'-1-[3-(6,7-Dichloro-3-pyridin-2-yl-quinoxalin-2-
ylamino)-propyl]-N'-1-methyl-propane-1,3-diamine;

2-{[3-(6,7-Dichloro-3-pyridin-2-yl-quinoxalin-2-
ylamino)-propyl]-(2-hydroxy-ethyl)-amino}-ethanol;

{4-[4-(2-Chloro-phenyl)-piperidin-1-yl]-butyl-(6,7-
dichloro-3-pyridin-2-yl-quinoxalin-2-yl)}amine;

(6,7-Dichloro-3-pyridin-2-yl-quinoxalin-2-yl)-(1-phenyl-
4-piperidin-1-yl-butyl)-amine;

[6,7-Dichloro-3-(1-ethyl-5-phenyl-imidazol-2-yl)-
quinoxalin-2-yl]-(4-pyrrolidin-1-yl-butyl)-amine;

[6,7-Dichloro-3-(1-phenyl-imidazol-2-yl)-quinoxalin-2-
yl]-(4-pyrrolidin-1-yl-butyl)-amine;

[6,7-Dichloro-3-[1-ethyl-5-(5-methyl-thiophene-2-yl)-
imidazol-5-yl]-quinoxalin-2-yl]-(4-pyrrolidin-1-yl-
butyl)-amine; and

[6,7-Dichloro-3-(1-phenyl-pyrazolo-5-yl)-quinoxalin-2-
yl]-(4-pyrrolidin-1-yl-butyl)-amine;

or a pharmaceutically acceptable salt thereof.

The compounds of Formula I and II are valuable receptor antagonists of IL-8.

The IL-8 chemokine inhibitory effects of compounds of the present invention were determined by the following procedures:

Chemotaxis Assay

Compounds of Formula I and II were evaluated for their effect on chemotaxis using methodology known in the art, e.g., Carr M. W., Roth S. J., Luther E., Rose S. S., and Springer T. A., "Monocyte chemoattractant protein 1 acts as a T-lymphocyte chemoattractant." *Proc. Natl. Acad Sci. USA*, 1994;91:3652; Qin S., Larosa G., Campbell J. J. et al., "Expression of MCP-1 and IL-8 receptors on subset on T-cells, and correlation with transendothelial chemotactic potential," *Eur. J. Immu.*, 1996;26:640.

Briefly, freshly isolated human neutrophils were resuspended in chemotaxis buffer, which is made of one part of RPMI 1640 medium, one part of Medium 199, and 0.5% BSA. The cells were incubated with or without compounds for 5 minutes. Similarly, rhIL-8 was incubated in a separate plate, then transferred into lower chambers of chemotaxis plate. Neutrophils were added onto the top chamber. The plates were incubated at 37° C. for 30 minutes. The top chamber was then removed and the plate frozen at −80° C. for 30 minutes. After thawing, migrated cells were stained with Cytoquant Cell Proliferation Assay Kit (Molecular Probes No. C-7026) and quantitated by reading the plate on a fluorescent plate reader.

Calcium Flux Assay

Compounds of Formula I and II were evaluated for their effect on calcium flux using methodology known in the art, e.g., Neote K., DiGregorio D., Mak J. Y., Horuk R., and Schall T. J., "Molecular cloning, functional expression, and signaling characteristics of a C—C chemokine receptor," *Cell*, 1993;72:415.

Briefly, human neutrophils were incubated with the fluorescence dye FLUO-3 for 1 hour. The cells were washed after this loading period, resuspended in HANKs buffer, and loaded into a 96-well plate. Compound was added to each well. After a 2-minute incubation period, the cells were stimulated with human IL-8 and the calcium flux response recorded and quantified.

The Table 1 shows the effect of a representative compound of the present invention on chemotaxis and calcium flux.

TABLE 1

| Example | IL-8 Chemotaxis (IC$_{50}$ = µM) | IL-8 Ca$^{+2}$ Flux % Inhibition (µM) |
|---|---|---|
| 1 | 0.89 | 34% @ 11 |
| 14 | 1.8 | |

TABLE 1-continued

| Example | IL-8 Chemotaxis (IC$_{50}$ = µM) | IL-8 Ca$^{+2}$ Flux % Inhibition (µM) |
|---|---|---|
| 15 | 0.32 | |
| 25 | 0.31 | |
| 28 | 0.4 | |
| 34 | 0.08 | |

The compounds of Formula I and II may be obtained by applying synthetic methodology known in the art, such as, for example, Werbel L. et al., *J. Med. chem.*, 1968;11:630; Moderhack D., et al., *Chem. Ber.*, 1994:1633; Loriga M, et al., *Farmaco*, 1995;50(5):289; *Chin. Chem. Lett.*, 1990;1(3): 25; Shepard T. and Smith D. M., *J. Chem. Soc.*, Perkin Trans I, 1987;3(501):11.

The procedures which may be used for the preparation of compounds 2 to 8 of Scheme 1 from compound 1 are described below.

Compounds of structure 4 in Scheme 1 are prepared by treating diamine 1 with the appropriate glyoxylate oxime in 20% to 40% H$_2$SO$_4$ at 50° C. to 80° C. for up to 2 days to give 2. Compound 3 is prepared by treatment of 2 with phosphorous oxychloride at reflux for up to 1 day. Treatment of 3 with two or more equivalents of the appropriate diamine in aromatic or ether solvents at reflux for up to 3 days gives 4. If one equivalent of diamine is used, treatment of one equivalent of an organic base or K$_2$CO$_3$ in aromatic solvents at reflux for up to 3 days is used to prepare 4 from 3.

Compounds of structure 5 are prepared by treating 3 with two or more equivalents of the corresponding thiol or amine in aromatic solvents at reflux for up to 3 days. If the acid salt of the thiol or amine is used, one or two equivalents of an organic base in aromatic solvents or ethers at reflux for up to 3 days may be used to prepare 5 from 3.

Compounds of structure 7 or 8 are prepared by treating 3 with 2 equivalents of the corresponding protected amine in aromatic solvents at reflux for up to 3 days to give 6. Compound 7 is prepared from 6 by treatment with concentrated mineral acid or gaseous HCl in aromatic solvent or alcohols at 0° to room temperature for up to 1 day. Treatment of 7 with formalin and formic acid at 50° C. to 100° C. for up to 2 days gives 8.

Scheme 1

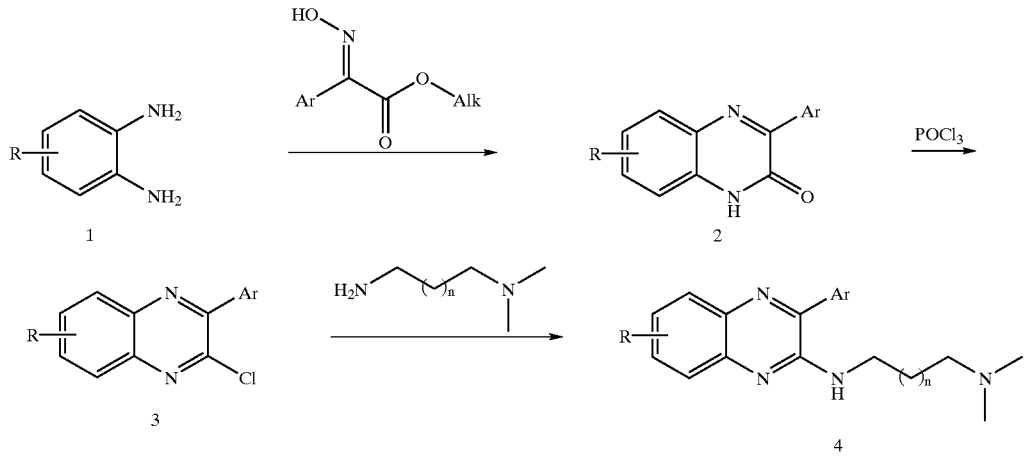

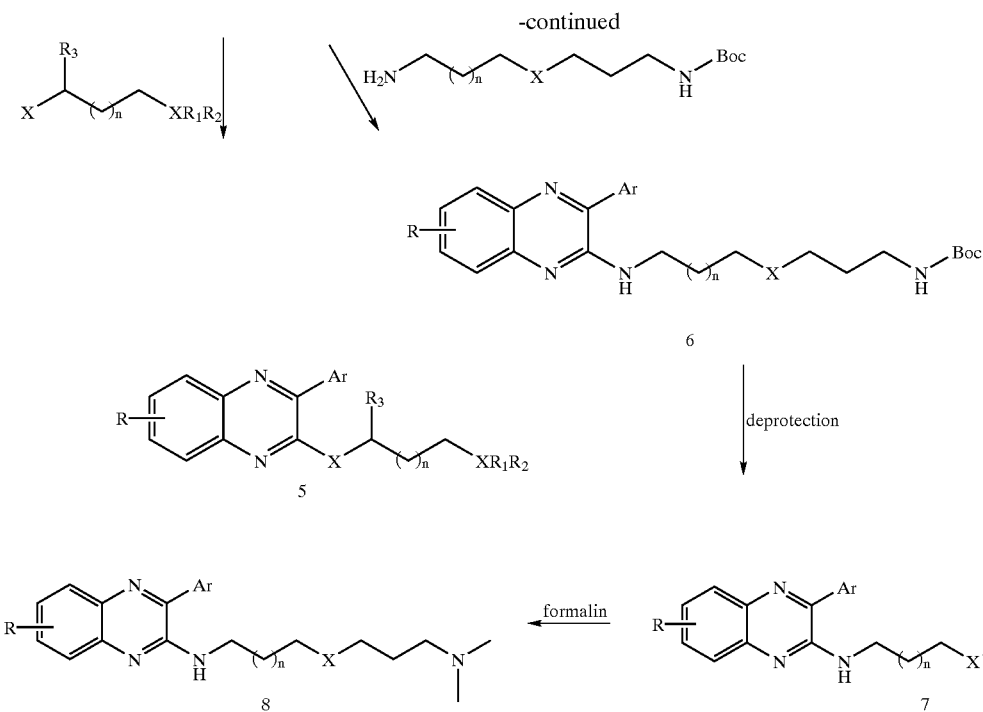
wherein Ar is Aryl or Pyridine and n=0 to 6;
R=Alkyl, alkoxy, halogen, or H;
$R_1$=Alkyl, aryl, or H;
$R_2$=Alkyl, aryl, or H;
X=Sulfur, oxygen, nitrogen, N—Me.
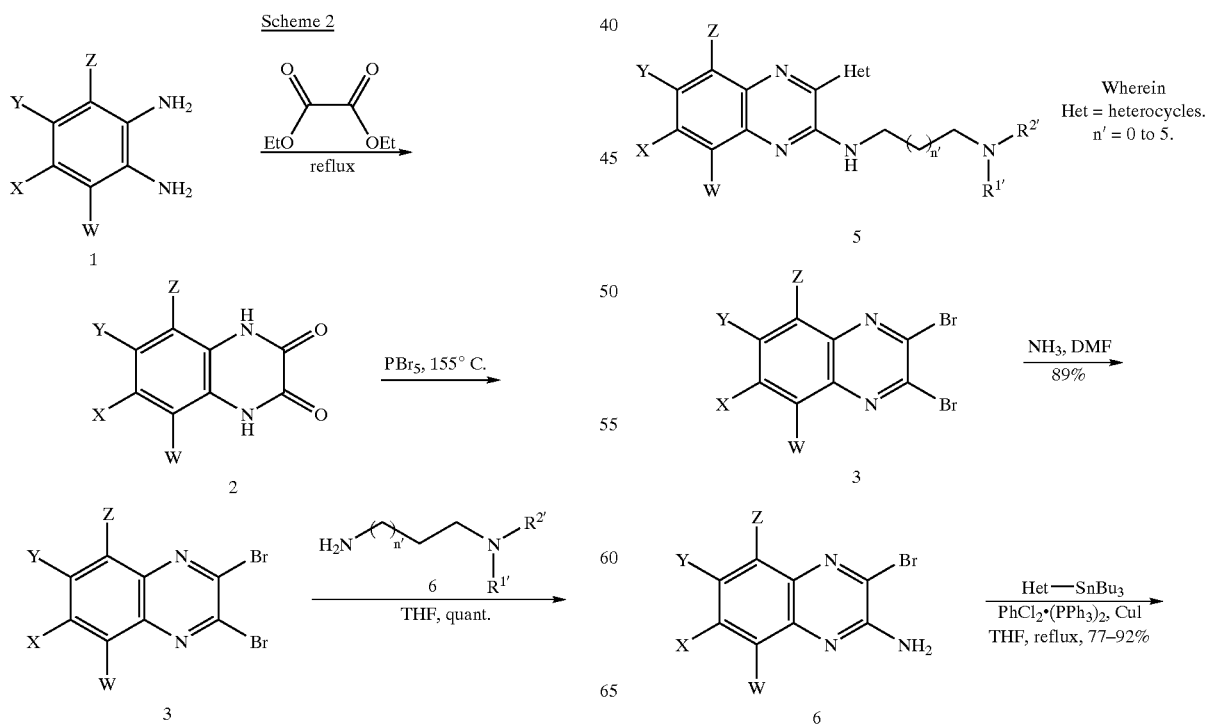

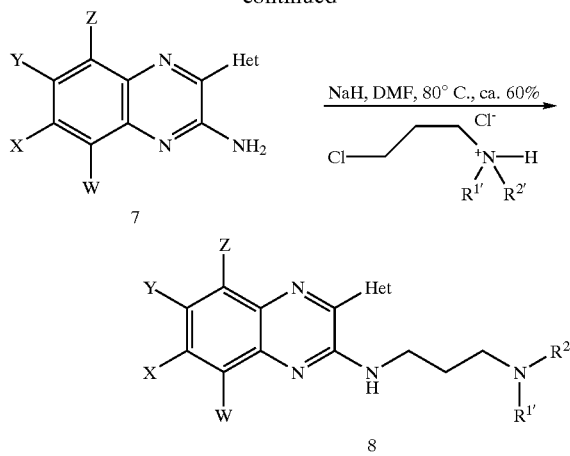

The procedure for the preparation of compound 2 to 8 of Scheme 2 are described below.

Compounds of structure 5 in Scheme 2 are prepared by treating diamine 1 with dialkyl oxalate at reflux (150–250° C.) for up to 10 hours to give 2. Compounds 3 are prepared upon treatment of 2 with a bromination reagent, preferably $PBr_5$ at 100° C. to 200° C. for up to 3 hours. The dibromide 3 is dissolved in diethyl ether or THF solvent and treated with two or more equivalents of the diamine 6 at 0° C. to room temperature for up to 5 hours to give compound 4. Compounds of structure 5 are prepared by treating 4 with heterocyclic stannanes, 1–10% catalytic palladium catalyst, preferably $Pd(PPh_3)_2Cl_2$, with 2–20% copper salt, such as CuI at 50° C. to 100° C. Additionally, compounds of structure 8 are prepared by reacting compounds 3 with ammonia followed by Stille-coupling reaction and alkylation as shown in Scheme 2.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or II or a corresponding pharmaceutically acceptable salt of a compound of Formula I or II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of psoriasis, or atopic dermatitis, disease associated with pathological angiogenesis (i.e., cancer), asthma, chronic obstructive pulmonary disease, adult respiratory distress syndrome, arthritis, inflammatory bowel disease, Crohn's disease, ulcerative colitis, gastric ulcer, septic shock, endotoxic shock, gram-negative sepsis, toxic shock syndrome, stroke, cardiac and renal reperfusion injury, glomerulo-nephritis, or thrombosis, Alzheimer's disease, graft versus host reaction, allograft rejections, or allergic diseases, the compounds utilized in the pharmaceutical method of this invention can be administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

SYNTHESIS OF INTERMEDIATES

Intermediate a 6,7-Dichloro-1,4-dihydroquinoxaline-2,3-dione

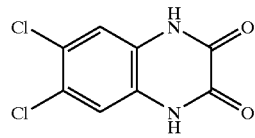

A mixture of 4,5-dichlorophenylenediamine (54 g, 305 mmol) and diethyl oxalate (124 mL, 146.1 g, 920 mmol) was refluxed overnight, cooled to room temperature, and filtered. The residue was washed with ethanol and dried in vacuo to give the title product as a gray solid powder (67.5 g, 96%); mp>320° C.; IR (KBr, cm$^{-1}$) 3188, 3156, 3057, 2918, 1724, 1693, 1613, 1497, 1452, 1340, 1338, 1250, 1131, 877, 811, 676, 669, 565; $^1$H NMR (DMSO) δ 12.00 (s, 2H), 7.18 (s, 2H); $^{13}$C NMR (DMSO) δ 154.8, 126.0, 124.4, 116.0; MS (ACPI), m/z 231.0 (M$^+$); Anal. Calcd for $C_8H_4N_2O_2Cl_2$: C, 41.59; H, 1.75; N, 12.12. Found: C, 41.60; H, 1.85; N, 12.05.

Intermediate b 2,3-Dibromo-6,7-dichloroquinoxaline

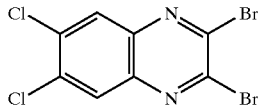

6,7-Dichloro-1,4-dihydro-quinoxaline-2,3-dione (5.39 g, 23.3 mmol) and phosphorus pentabromide (20.1 g, 46.7 mmol) were charged in a 100 mL round-bottom flask equipped with a condenser with an outlet half immersed in 10% NaOH aqueous solution (to absorb HBr generated during the reaction). The reaction was heated at 155° C. using an oil-bath for 2 hours when the formation of HBr ceased. The reaction content was poured into ice-water (100 mL) and basified with NH$_4$OH. After filtration, the solid was dried and recrystallized using EtOH to give the desired product as a white solid (7.84 g, 94% yield): mp 169–70° C.; $R_f$=0.50, CH$_2$Cl$_2$; IR (KBr, cm$^{-1}$) 3088, 1539, 1451, 1240, 1128, 964, 997; $^1$H NMR (CDCl$_3$) δ 8.13 (s, 2H); $^{13}$C NMR (CDCl$_3$) δ 142.4, 139.7, 136.3; MS (ACPI), m/z 338.4 (MH$^+$); Anal. Calcd for $C_8H_2N_2Cl_2Br_2$: C, 26.93; H, 0.56; N, 7.85. Found: C, 26.93; H, 0.56; N, 7.86.

Intermediate c

2-Bromo-3amino-6,7-dichloroquinoxaline

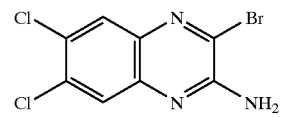

2,3-Dibromo-6,7-dichloro-quinoxaline (2.75 g, 7.7 mmol) was dissolved in DMF (50 mL). Anhydrous ammonia was bubbled into the solution. After 2 hours, DMF was removed in vacuo at 70° C. The residue was filtered through a pad of silica gel (one inch thick) eluted with ethyl acetate. After removal of the solvent in vacuo, the residue was recrystallized from acetone to give the desired 2-bromo-3-amino-6,7-dichloroquinoxaline as a white solid. (7.84 g, 89% yield): mp 232–4° C.; $R_f$=0.41, EtOAc:Hex (1:1); IR (KBr, cm$^{-1}$) 3488, 3348, 1617, 1588, 1443, 1406, 1338, 1114, 1036, 965, 893, 867, 577, 557; $^1$H NMR (DMSO) δ 8.02 (s, 1H), 7.76 (s, 1H), 7.51 (broad s, 2H, NH$_2$), 7.18 (s, 2H); $^{13}$C NMR (DMSO) δ 147.7, 136.7, 131.4, 129.0, 128.8, 124.4, 122.3, 121.9; MS (ACPI), m/z 291.8 (M−1)$^-$; Anal. Calcd for $C_8H_4N_3BrCl_2$: C, 32.80; H, 1.38; N, 14.34. Found: C, 32.98; H, 1.43; N, 14.34.

Intermediate d

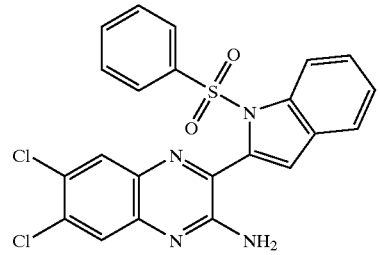

A 50 mL round-bottom flask was charged with 2-bromo-3-amino-6,7-dichloro-quinoxaline (1.03 g, 3.52 mmol), 1-benzenesulfonyl-2-tributylstannyl-1H-indole (2.30 g, 4.21 mmol), bis(triphenylphosphine)palladium (II) chloride (259 mg, 0.352 mmol), CuI (77 mg, 0.703 mmol), and THF (40 mL). The suspension was refluxed for 30 minutes, cooled to room temperature. Charcoal was added, and the reaction mixture was heated to boil and filtered through a pad of Celite (1 inch thick). The filtrate was concentrated in vacuo, and the residue was chromatographed using neutral alumina and eluting with 0–5% CH$_3$OH/EtOAc to give the desired product as a yellow solid (1.51 g, yield 92%): mp 129–132° C.; $R_f$=0.26, EtOAc:Hex (1:1); $^1$H NMR (DMSO) δ 8.14 (s, 1H), 8.03 (d, J=8.4 Hz, 1H), 7.86 (d, J=1.6 Hz, 1H), 7.84 (d, 1H), 7.63 (m, 4H), 7.43 (dt, J1=7.32, 1.1 Hz, 1H), 7.31 (dt, J=7.32, 0.9 Hz, 1H), 7.17 (broad s, 2H); $^{13}$C NMR (DMSO) δ 153.6, 141.8, 141.1, 136.7, 136.4, 134.7, 134.6, 134.3, 132.8, 130.0, 129.6, 129.4, 126.9, 125.9, 125.7, 125.6, 124.2, 122.0, 114.7; MS (ACPI), m/z 469.0.0 (M$^+$+1), 471.0 (M$^+$+2); Anal. Calcd for $C_{22}H_{14}N_4Cl_2O_2S_1$: C, 56.30; H, 3.01; N, 11.94. Found: C, 56.22; H, 3.04; N, 11.82.

Intermediate e

2-Amino-3-(2-furanyl)-6,7-dichloroquinoxaline

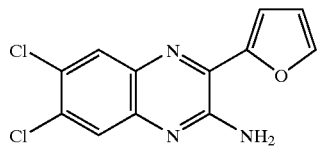

The title compound was prepared according to the experimental procedure for Intermediate d and was obtained as a yellow crystalline solid (yield 84%): mp 222–223° C.; $R_f$=0.26, EtOAc:Hex (1:1); $^1$H NMR (DMSO) 8.14 (s, 1H), 8.03 (d, J=8.4 Hz, 1H), 7.86 (d, J=1.6 Hz, 1H), 7.84 (d, 1H), 7.63 (m, 4H), 7.43 (dt, J1=1.1 Hz, J2=7.32 Hz, 1H), 7.31 (dt, J=6.77, 0.9 Hz, 1H), 7.17 (broad s, 2H); $^{13}$C NMR (DMSO) δ 153.6, 141.8, 141.1, 136.7, 136.4, 134.7, 134.6, 134.3, 132.8, 130.0, 129.6, 129.4, 126.9, 125.9, 125.7, 125.6, 124.2, 122.0, 114.7; MS (ACPI), m/z 469.0.0 (M$^+$+1), 471.0 (M$^+$+2); Anal. Calcd for $C_{22}H_{14}N_4Cl_2O_2S_1$: C, 56.30; H, 3.01; N, 11.94. Found: C, 56.22; H, 3.04; N, 11.82.

Intermediate f

2-Amino-3-(2-thiophenyl)-6,7-dichloroquinoxaline

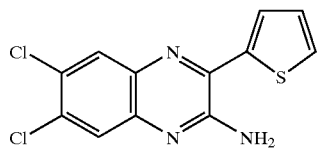

The title compound was prepared according to the experimental procedure for Intermediate d and was obtained as a yellow crystalline solid (yield 77%): mp 235–237° C.; $R_f$=0.17, EtOAc:Hex (1:2); IR (KBr, cm$^{-1}$) 3472, 3311, 1614, 1588, 1463, 1432, 1404, 1351, 1329, 1227, 1110, 948, 879, 849, 728, 597; $^1$H NMR (DMSO) 7.19 (broad s, 1H), 7.24 (dd, J=5.1, 3.8 Hz, 1H), 7.72 (s, 1H), 7.83 (dd, J=5.1, 0.9 Hz, 1H), 7.94 (dd, J=5.1, 0.9 Hz, 1H), 7.96 (s, 1H); $^{13}$C NMR (DMSO) δ 151.1, 140.4, 140.3, 140.2, 135.3, 131.7, 130.8, 128.8, 126.2, 125.6; MS (ACPI), m/z 295.9 (M$^+$), 293.9 (M$^+$-2); Anal. Calcd for $C_{12}H_7N_3Cl_2S_1$: C, 48.66; H, 2.38; N, 14.19. Found: C, 48.74; H, 2.58; N, 14.06.

Intermediate g

2-Amino-3-(2-thiazole)-6,7-dichloroquinoxaline

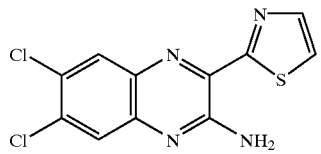

The title compound was prepared according to the experimental procedure for Intermediate d and was obtained as a bright yellow crystalline solid (yield 81%): mp 219–221° C.; $R_f$=0.19, EtOAc:Hex (1:2); IR (KBr, cm$^{-1}$) 3426, 3363, 3320, 3200, 1624, 1459, 1341, 1235, 1208, 1109, 953, 884, 812, 462; $^1$H NMR (DMSO) 7.29 (broad s, 1H), 7.79 (s, 1H), 8.05 (s, 1H), 8.67 (s, 1H), 9.31 (s, 1H); $^{13}$C NMR (DMSO) δ 158.0, 151.4, 143.8, 140.4, 139.2, 135.7, 132.4, 128.8, 126.5, 125.8; MS (ACPI), m/z 296.9 (M$^+$+1), 298.9 (M$^+$+2); Anal. Calcd for $C_{11}H_6N_4Cl_2S_1$: C, 44.46; H, 2.04; N, 18.85. Found: C, 44.39; H, 2.10; N, 18.56.

Intermediate h

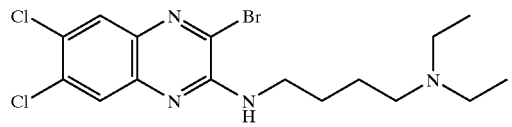

To a solution of 2,3-dibromo-6,7-dichloroquinoxaline (intermediate b) (10.35 g, 29.0 mmol) in THF (100 mL), 4-(diethylamino)butyl amine (8.35 g, 58.0 mmol) was added at room temperature. After 30 minutes, the reaction mixture was filtered to remove the precipitate. After the removal of the solvent in vacuo, the residue was chromatographed using silica gel, eluted with 2.5% Et$_3$N, 2.5% MeOH, 95% EtOAc, to give the desired product as a orange-yellow oil (12.18 g, 100%) $^1$H NMR (CDCl$_3$) 1.03 (t, J=7.14 Hz), 1.61 (m, 2H), 1.72 (m, 2H), 2.52 (m, 6H), 3.56 (m, 2H), 5.96 (t, J=4.94 Hz), 7.79 (s, 1H), 7.87 (s, 1H); Anal. Calcd for $C_{16}H_{21}N_4Br_1Cl_2$: C, 42.08; H, 4.86; N, 12.27; Found: C, 42.09; H, 4.79; N, 11.88.

Intermediate i

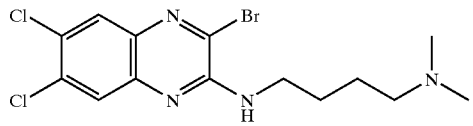

To a solution of 2,3-dibromo-6,7-dichloroquinoxaline (intermediate b) (10.4 g, 29.1 mmol) in THF (100 mL), 4-(dimethylamino)butyl amine (5.2 g, 44.8 mmol) was added at room temperature. After 30 minutes, the reaction mixture was filtered to remove the precipitate. After the removal of the solvent in vacuo, the residue was chromatographed using silica gel, eluted with 2.5% Et$_3$N, 2.5% MeOH, 95% EtOAc, to give the desired product as a orange-yellow oil (11.40 g, 100%).

EXAMPLE 1

6-Chloro-N-[4-(dimethylamino)cyclohexyl]-3-(2-pyridinyl)-2-quinoxalinamine and 7-Chloro-N-[4-(dimethylamino)cyclohexyl]-3-(2-pyridinyl)-2-quinoxalinamine, Dihydrochloride, Hydrate mp 151–153° C. (Werbel et al., *J. Med. Chem.*, 1968;11:630).

EXAMPLE 2

N-(1-Azabicyclo[2.2.2]octan-3-yl)-3-(2-pyridinyl)-2-quinoxalinamine mp 63–65° C.

EXAMPLE 3

N-[3-(1H-Imidazol-1-yl)propyl]-3-(2-pyridinyl)-2-quinoxalinamine mp 85–86° C.

EXAMPLE 4

N-[2-(1-Methyl-2-pyrrolidinyl)ethyl]-3-(2-pyridinyl)-2-quinoxalinamine mp 186–188° C.

EXAMPLE 5

1-[3-[[3-Pyridinyl)-2-quinoxalinamine]amino]propyl]-2-pyrrolidinone

Pale amber viscous liquid.

EXAMPLE 6

N-[4-(4-Morpholinyl)phenyl]-3-(2-pyridinyl)-2-quinoxalinamine mp 205–206° C.

EXAMPLE 7

N-(4-Pyridinylmethyl)-3-(2-pyridinyl)-2-quinoxalinamine mp 142–144° C.

EXAMPLE 8

N-[4-(Dimethylamino)phenyl]-3-(2-pyridinyl)-2-quinoxalinamine mp 169–170° C.

EXAMPLE 9

N-Methyl-N-[4-[[3-(2-pyridinyl)-2-quinoxalinyl]amino]phenyl]-acetamide mp 165–166° C.

EXAMPLE 10

N-(6,7-Dichloro-3-pyridin-2-yl-quinoxalin-2-yl)-N',N'-dimethyl-cyclohexane-1,4-diamine

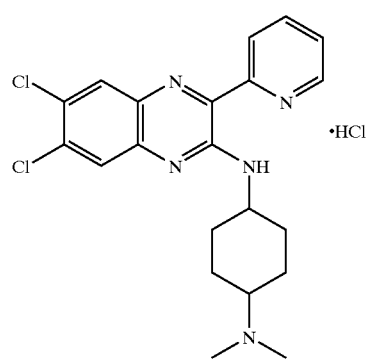

The title compound was prepared according to the experimental procedure for Example 1 and was obtained as a yellow solid (84% yield); mp 180–182° C.; $^1$H NMR (DMSO) δ 1.80–2.45 (m, 8H), 2.92 (s, 6H), 4.58 (broad s, 1H), 7.80 (m, 1H), 7.75 (s, 1H), 8.07 (s, 1H), 8.10 (m, 1H), 8.82 (m, 1H); $^1$Anal. Calcd for $C_{21}H_{23}N_5Cl_2 \cdot 1.0HCl$: C, 55.70; H, 5.34; N, 15.47. Found: C, 55.52; H, 5.22; N, 15.42.

EXAMPLE 11

N-(6,7-Dichloro-3-pyridin-2-yl-quinoxalin-2-yl)-cyclohexane-1,4-diamine

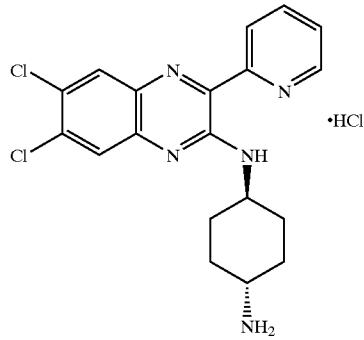

The title compound was prepared according to the experimental procedure for Example 1 following removal of BOC protecting group with HCl and was obtained as a yellow solid (98% yield); mp 280–282° C. (dec.); $^1$H NMR (DMSO) δ 1.82 (m, 4H), 2.22 (m, 2H), 2.46 (m, 2H), 4.38 (broad, s, 1H), 7.74 (dd, $J_1$=7.0, 4.7 Hz, 1H), 8.21 (dd, J=15.0, 7.0 Hz, 1H), 8.82 (dd, J=8.0, 4.0 Hz, 1H); $^1$Anal. Calcd for $C_{19}H_{19}N_5Cl_2 \cdot 2.0HCl$: C, 49.48; H, 4.59; N, 15.18. Found: C, 49.03; H, 4.64; N, 14.98.

EXAMPLE 12

2-[1,4']Bipiperidinyl-1'-yl-6,7-dichloro-3-pyridin-2-yl-quinoxaline

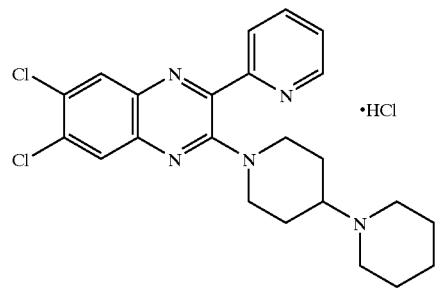

The title compound was prepared according to the experimental procedure for Example 1 and was obtained as a bright yellow solid (92%); mp 275–277° C. (dec.); $^1$H NMR (CDCl$_3$) δ 1.33–1.82 (m, 12H), 2.48 (s, 3H), 2.75 (t, J=12.7 Hz, 2H), 7.35 (t, J=6.1 Hz, 1H), 7.87 (s, 1H), 7.37 (m, 1H), 8.06 (s, 1H), 8.76 (s, 1H); Anal. Calcd for $C_{23}H_{25}N_5Cl_2 \cdot 1.32HCl$: C, 56.32; H, 5.41; N, 14.28. Found: C, 56.33; H, 5.36; N, 14.07.

EXAMPLE 13

(6,7-Dichloro-3-pyridin-2-yl-quinoxalin-2-yl)-(4-diethylaminomethyl-phenyl)-amine

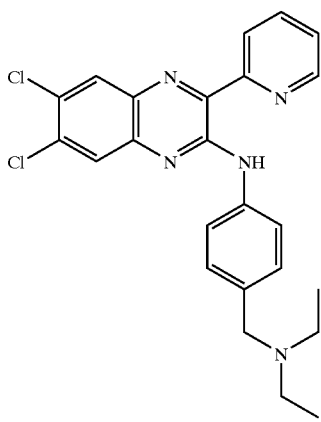

The title compound was prepared according to the experimental procedure for Example 1 and was obtained as an orange powder (83%); mp 250–252° C. (dec.); $^1$H NMR (CDCl$_3$) δ 1.04 (t, J=7.1 Hz, 6H), 2.57 (q, J=7.1 Hz, 4H), 3.61 (s, 2H), 7.38 (d, J=8.4 Hz, 2H), 7.48 (dd, J=5.0, 1.0 Hz, 1H), 7.93 (s, 1H), 7.90(s, 2H), 7.97 (dt, J=8.1, 2.0 Hz, 1H), 8.03 (s, 1H), 8.73 (d, J=4.8 Hz, 1H), 8.84 (d, J=8.1 Hz, 1H), 12.87 (s, 1H); Anal. Calcd for C$_{24}$H$_{23}$N$_5$Cl$_2$·0.42 H$_2$O: C, 62.67; H, 5.22; N, 15.23. Found: C, 62.70; H, 5.05; N, 15.04.

EXAMPLE 14

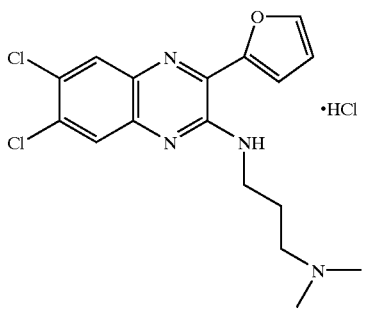

N'-(6,7-Dichloro-3-furan-2-yl-quinoxalin-2-yl)-N,N-dimethyl-propane-1,3-diamine

To a solution of NaH (150 mg, 60% in mineral oil, 3.75 mmol) in DMF (10 mL) was added quinoxaline amine intermediate e (420 mg, 1.50 mmol) and 3-dimethylaminopropyl chloride hydrochloride (237 mg, 1.5 mmol). The reaction was heated at 80° C. for 2 hours, cooled to room temperature. After removal of DMF in vacuo, the residue was chromatographed using neutral alumina eluted with 5–15% CH$_3$OH/EtOAc to give the desired product as a dark-yellow solid (94 mg, yield 60%); as a bis-HCl, salt was obtained as a yellow solid by bubbling HCl gas into its EtOAc solution; mp 175–177° C.

EXAMPLE 15

N'-(6,7-Dichloro-3-thiophen-2-yl-quinoxalin-2-yl)-N,N-dimethyl-propane-1,3-diamine

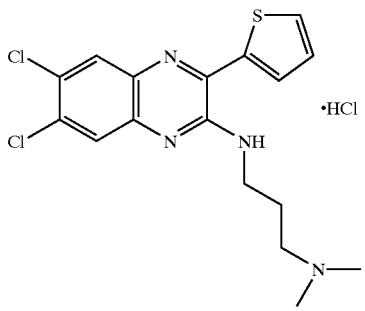

The title compound was prepared according to the experimental procedure for Example 14 using Intermediate f and was obtained as a bis-HCl salt; mp 220–223° C.; $^1$H NMR (DMSO) δ 2.10 (m, 2H), 2.73 (δ, J=4.8 Hz, 6H), 3.13 (m, 2H), 3.60 (m, 2H), 7.28 (dd, J$_1$=5.1 Hz, J$_2$=3.7 Hz, 1H), 7.58 (broad t, 1H, NH), 7.86 (s, 1H), 7.88 (d, J=5.1, 1.0 Hz, 1H), 7.98 (dd, J=4.0, 1.0 Hz, 1H), 8.00 (s, 1H), 10.80 (broad s, 1H); Anal. Calcd for C$_{17}$H$_{18}$N$_4$Cl$_2$O: C, 46.60; H, 4.60; N, 12.79. Found: C, 46.62; H, 4.62; N, 12.57.

EXAMPLE 16

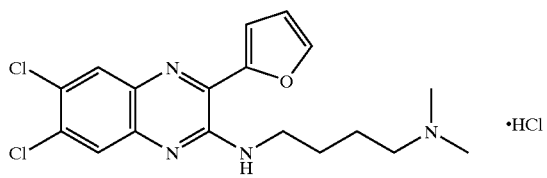

The quinoxaline bromide Intermediate i (890 mg, 2.27 mmol) was dissolved in THF (30 mL). To this solution was added tributylstannyl-2-furan (1.05 g, 2.95 mmol), PdCl$_2$·(PPh$_3$)$_2$ (80 mg, 0.113 mmol), and CuI (25 mg, 0.23 mmol). The resulting suspension was refluxed for 2 hours, cooled to room temperature, and filtered. The volatiles were removed in vacuo, and the residue was chromatographed using silica gel eluting with 5% Et$_3$N and 5% CH$_3$OH in EtOAc to give the desired product as a viscous oil. The bis HCl salt was prepared by bubbling HCl gas into the EtOAc solution of the free base; mp 247–248° C.

EXAMPLE 17

N'-(6,7-Difluoro-3-thiophen-2-yl-quinoxalin-2-yl)-N,N-dimethyl-butane-1,4-diamine

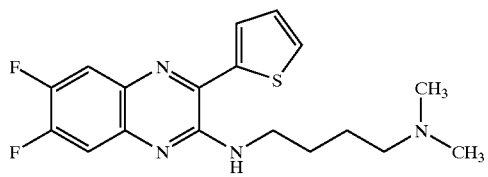

The title compound was prepared according to the experimental procedure for Example 16, and the free base was obtained as a yellow solid; mp 175–177° C.; $^1$H NMR (DMSO) δ, 1.60–1.80 (m, 4H), 2.19 (s, 6H), 2.36 (t, J=7.0 Hz, 2H), 3.55 (q, J=6.5 Hz, 2H), 6.12 (broad s, 1H), 7.18 (dd, J1=5.0, 3.9 Hz, 1H), 7.42 (dd, J=11.4, 8.0 Hz, 1H), 7.54 (dd, J=5.1, 0.9 Hz, 1H), 7.61 (dd, J=11.8, 7.4 Hz, 1H), 7.68 (dd, J=3.5, 0.5 Hz, 1H); Anal. Calcd for $C_{18}H_{20}N_4F_2S \cdot 0.72H_2O$: C, 57.59; H, 5.76; N, 14.92. Found: C, 57.60; H, 5.44; N, 14.80.

EXAMPLE 18

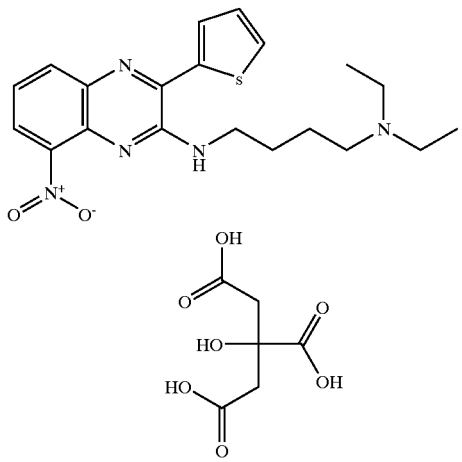

The title compound was prepared according to the experimental procedure for Example 16, and the mono-citrate was obtained as a bright yellow powder; mp 110–112° C.; $^1$H NMR (DMSO) δ, 1.15 (t, J=7.2 Hz, 6H), 1.57 (m, 4H), 2.50 (q, J=9.7 Hz, 4H), 3.05 (m, 8H), 3.49 (q, J=5.7 Hz, 2H), 7.28 (dd, J=5.1, 3.9 Hz, 1H), 7.43 (t, J=8.0 Hz, 1H), 7.70 (t, J=5.5 Hz, 1H), 7.90 (ddd, J=7.0, 3.8, 0.9 Hz, 1H), 8.04 (ddd, J=13.6, 7.7, 1.3 Hz, 1H); Anal. Calcd for $C_{20}H_{24}N_5O_2S \cdot 1.0C_6H_8O_7 \cdot 1.0H_2O$: C, 51.31; H, 5.63; N, 11.51. Found: C, 51.18; H, 5.43; N, 11.15.

EXAMPLE 19

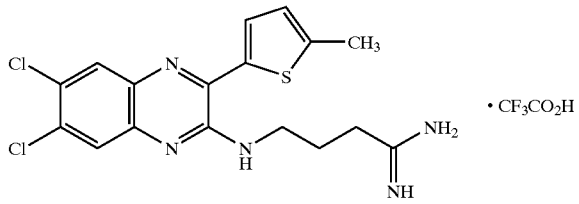

Using the procedure of Example 15, 3-cyano propyl amine intermediate was obtained. The nitrile was subsequently treated with ethanol.HCl followed by ammonia in ethanol. The free base was converted to a TFA salt as a fluffy yellow powder; mp 106–108° C.; $^1$H NMR (DMSO) δ, All peaks are broad singlets, 2.01 (2H), 2.55 (5H), 3.52 (2H), 6.70 (1H), 7.40 (1H), 7.50 (1H), 7.78 (1H), 7.80 (1H), 8.74 (1H), 8.92 (1H).

EXAMPLE 20

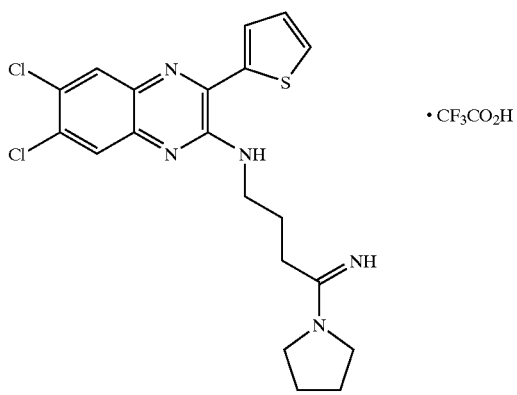

The title compound was prepared from the corresponding nitrile according to the procedure of Example 19 and obtained as a brown waxy oil; $^1$H NMR (CDCl$_3$) δ, All peaks are broad singlets, 1.98 (4H), 2.08 (2H), 2.66 (2H), 3.52 (4H), 3.64 (2H), 6.30 (1H), 7.16 (1H), 7.52 (1H), 7.70 (11H), 7.87 (1H), 7.90 (1H).

EXAMPLE 21

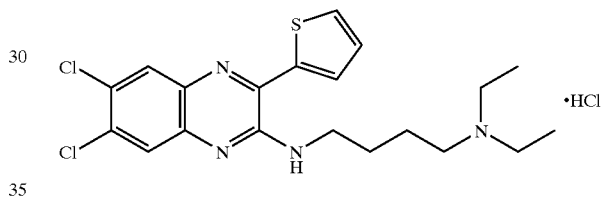

The title compound was prepared according to the experimental procedure for Example 16 using Intermediate h, and was obtained as a yellow-orange oil (quantitative yield). The compound was then dissolved in EtOAc, and HCl gas bubbled in to make the corresponding HCl salt. The salt was a yellow hygroscopic powder: Anal. Calcd for $C_{20}H_{24}N_4Cl_2S \cdot (2)HCl \cdot (1.24)H_2O$: C, 46.32; H, 5.51; N, 10.80. Found: C, 46.32; H, 5.55; N, 10.76.

EXAMPLE 22

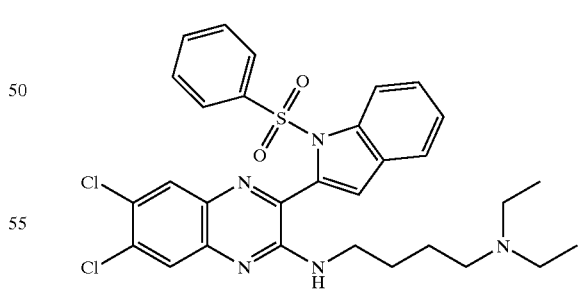

The title compound was prepared according to the experimental procedure for Example 16 using Intermediate h, and was obtained as an orange oil (77%); $^1$H NMR (CDCl$_3$) 0.99 (t, J=7.15 Hz, 6H), 1.59 (m, 2H), 1.68 (m, 2H), 2.55 (m, 6H), 3.57 (dd, J=12.45, 5.49 Hz, 2H), 5.36 (broad t, J=5.49 Hz, 1H), 6.95 (d, J=0.73 Hz, 1H), 7.45 (m, 6H), 7.69 (s, 1H), 7.72 (s, 1H), 7.89 (s, 1H), 7.95 (s, 1H), 8.19 (dd, J=8.33, 0.85, 1H); MS (APCI), M/z 598.1 (M$^+$+1), 599.1 (M$^+$+2).

EXAMPLE 23

N'-[6,7-Dichloro-3-(1H-indol-2-yl)-quinoxalin-2-yl]-N,N-diethyl-butane-1,4-diamine

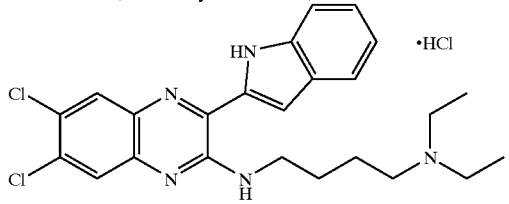

The title compound was prepared by refluxing a sodium hydroxide solution of Example 22 in methanol to remove the toluene sulfonamide protecting group, and the compound was obtained as a red-orange oil. The compound was then dissolved in EtOAc, and treated with HCl in EtOAc to form the HCl salt. The product is a brown-orange solid (98%); mp 145–147° C.; Salt $^1$H NMR (DMSO) 1.15 (broad t, J=6.8 Hz, 6H), 1.72 (broad s, 4H), 3.04 (broad S, 6H), 3.57 (broad s, 2H), 7.03 (t, J=7.32 Hz, 1H), 7.19 (t, J=7.78, 1H), 7.38 (broad s, 1H), 7.49 (d, J=8.05 Hz, 1H), 7.63 (d, J=7.81 Hz, 1H), 7.80 (s, 1H), 7.94 (s, 1H), 10.17 (broad s, 1H), 11.76 (s, 1H); Anal. Calcd for $C_{24}H_{27}N_5Cl_2.(2)HCl.(1.58)H_2O$: C, 51.68; H, 5.81; N, 12.56. Found: C, 51.68; H, 5.83; N, 12.45.

EXAMPLE 24

The title compound was prepared according to the experimental procedure for Example 16, and 2 regioisomers were obtained. The major product was obtained as an orange oil. The oil is dissolved in acetone and treated with 1 eq of 4-bromobenzoic acid and stored at 4° C. for 24 hours to give the salt as a yellow solid (78%); mp 91–92° C.; Free base $^1$H NMR (CDCl$_3$) 1.00 (t, J=7.14 Hz, 3H), 1.59 (m, 2H), 1.73 (m, 2H), 2.49 (m, 6H), 3.61 (dd, J=12.12, 6.87 Hz, 2H), 6.09 (broad t, J=4.90 Hz, 1H), 7.21 (dd, J=5.13, 3.66 Hz, 1H), 7.59 (dd, J=5.13, 0.92 Hz, 1H), 7.69 (dd, J=3.66, 0.92 Hz, 1H), 7.78 (s, 1H), 8.203 (s. 1H); Anal. Calcd for $C_{21}H_{24}N_4Cl_1F_3S.(0.25)C_7H_5O_2Br$: C, 53.87; H, 5.02; N, 11.05; Found: C, 53.72; H, 5.10; N, 11.20.

EXAMPLE 25

N'(3-Benzo[b]thiophen-2-yl-6,7-dichloro-quinoxalin-2-yl)-N,N-4-diethyl-butane-1,4-diamine

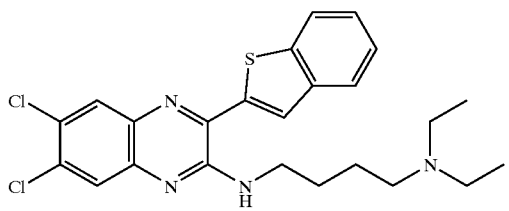

The title compound was prepared according to the experimental procedure for Example 16 using Intermediate h, and was obtained as a yellow oil (99%); $^1$H NMR (CDCl$_3$) 0.99 (t, J=7.14 Hz, 6H), 1.61 (m, 2H), 1.75 (m, 2H), 2.49 (m, 6H), 3.61 (dd, J=12.35, 6.84 Hz, 2H), 6.00 (broad t, J=5.13 Hz, 1H), 7.43 (m, 2H), 7.81 (s, 1H), 7.86 (m, 2H), 7.92 (s, 1H), 7.99 (s, 1H); Anal. Calcd for $C_{24}H_{26}N_4Cl_2S.(0.19)CHCl_3$: C, 58.56; H, 5.32; N, 11.29; Found: C, 58.52; H, 5.38; N, 11.19.

EXAMPLE 26

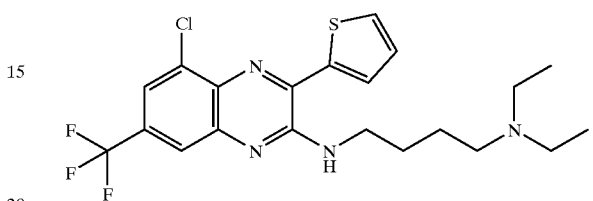

The title compound was prepared according to the experimental procedure for Example 16, and 2 regioisomers were obtained. The major product was collected as an orange oil; $^1$H NMR (CDCl$_3$) 0.99 (t, J=7.14 Hz, 6H), 1.62 (m, 2H), 1.78 (m, 2H), 2.50 (m, 6H), 3.71 (dd, J$_1$=12.37 Hz, J$_2$=6.86 Hz 2H), 6.21 (broad t, J=4.86 Hz, 1H), 7.21 (dd, J=5.03, 3.75 Hz, 1H), 7.61 (dd, J=5.12, 1.10 Hz, 1H), 7.73 (dd, J=3.75, 0.92 Hz, 1H), 7.82 (d, J=1.64 Hz, 1H), 8.08 (t, J=0.97 Hz, 1H); Anal. Calcd for $C_{21}H_{24}N_4Cl_1F_3S$: C, 55.20; H, 5.29; N, 12.26; Found: C, 55.22; H, 5.05; N, 11.77.

EXAMPLE 27

N,N-Diethyl-N'-(3-thiophen-2-yl-7-trifluoromethyl-quinoxalin-2-yl)-butane-1,4-diamine

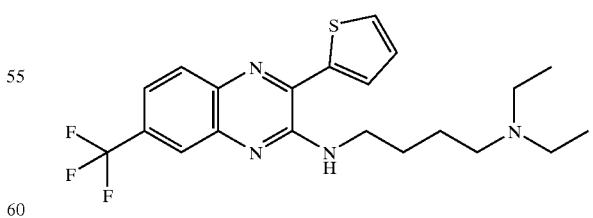

The title compound was prepared according to the experimental procedure for Example 16, and 2 regioisomers were obtained. The major product was collected as an orange oil (92.4%); $^1$H NMR (CDCl$_3$) 1.00 (t, J=7.14 Hz, 6H), 1.60 (m, 2H), 1.74 (m, 2H), 2.50 (m, 6H), 3.63 (m, 2H), 5.95 (broad s, 1H), 7.59 (t, J=4.40 Hz, 1H), 7.58 (d, J=4.51 Hz, 1H), 7.71 (m, 3H), 8.17 (s, 1H); Anal. Calcd for $C_{21}H_{25}N_4F_3S$: C, 59.70; H, 5.96; N, 13.26; Found: C, 60.56; H, 5.94; N, 13.00.

EXAMPLE 28

N'-[6,7-Dichloro-3-(5-methyl-thiophen-2-yl)quinoxalin-2-yl]-N,N-diethyl-butane-1,4-diamine

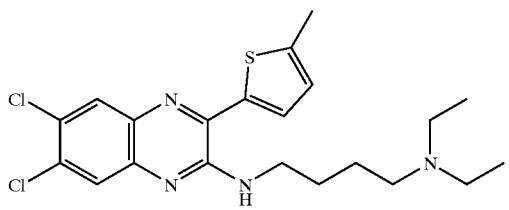

The title compound was prepared according to the experimental procedure for Example 16 using Intermediate h, and the product was obtained as a yellow oil (95.1%); $^1$H NMR (DMSO) 0.89 (t, J=7.14 Hz, 6H), 1.45 (m, 2H), 1.64 (m, 2H), 2.48 (m, 2H), 2.51 (s, 3H), 3.44 (t, J=6.23 Hz, 2H), 6.95 (d, J=3.66 Hz, 1H), 7.27 (t, J=5.31 Hz, 1H), 7.69 (d, J=3.66 Hz, 1H), 7.73 (s, 1H), 7.91 (s, 1H); Anal. Calcd for $C_{21}H_{26}N_4Cl_2S$: C, 57.66; H, 5.99; N, 12.81; Found: C, 57.44; H, 6.01; N, 12.40.

EXAMPLE 29

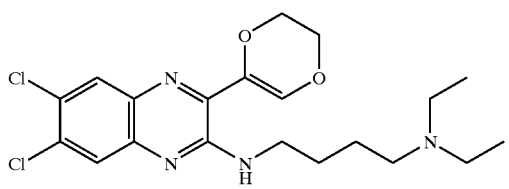

The title compound was prepared according to the experimental procedure for Example 16 using Intermediate h, and the product was obtained as a yellow-orange oil (79%); $^1$H NMR (CDCl$_3$) 1.03 (t, J=7.08 Hz, 6H), 1.59 (m, 2H), 1.68 (m, 2H), 2.52 (m, 6H), 3.52 (dt, J=7.08, 5.37 Hz, 2H), 4.26 (m, 2H), 4.31 (m, 2H), 6.73 (t, J=5.37 Hz, 1H), 7.15 (s, 1H), 7.70 (s, 1H), 7.80 (s, 1H); Anal. Calcd for $C_{20}H_{26}N_4Cl_2O_2$.(0.06)H$_2$O: C, 56.33; H, 6.16; N, 13.14; Found: C, 56.33; H, 6.15; N, 12.86.

EXAMPLE 30

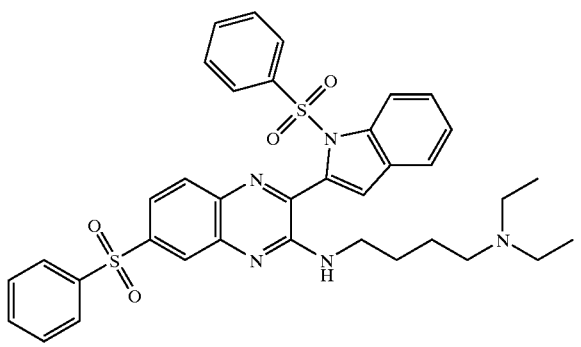

The title compound was prepared according to the experimental procedure for Example 16, and was obtained as a yellow-orange glass (90.2%); $^1$H NMR (CDCl$_3$) 0.99 (t, J=7.08 Hz, 6H), 1.59 (m, 2H), 1.69 (m, 2H), 2.51 (m, 4H), 3.63 (broad s, 2H), 5.59 (t, J=5.20, 1H), 6.95 (s, 1H), 7.32 (t, J=7.56, 1H), 7.39 (t, J=7.81 Hz, 1H), 7.44 (t, J=7.81 Hz, 1H), 7.55 (m, 6H), 7.69, (d, J=8.24 Hz, 1H), 7.79 (d, J=8.79 Hz, 1H), 8.02 (m, 4H), 8.17 (d, J=8.30 Hz, 1H), 8.50 (d, J=1.95 Hz, 1H); Anal. Calcd for $C_{36}H_{37}N_5S_2O_4$.(0.49)H$_2$O: C, 63.90; H, 5.66; N, 10.35; Found: C, 63.91; H, 5.46; N, 9.98.

EXAMPLE 31

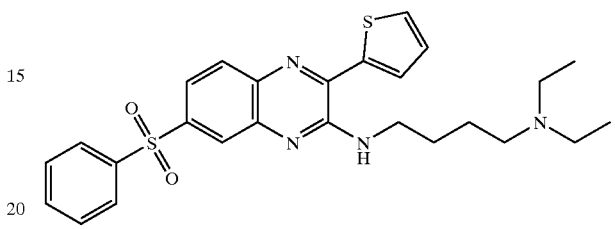

The title compound was prepared according to the experimental procedure for Example 16, and was obtained as a yellow-orange glass (99.2%); $^1$H NMR (CDCl$_3$) 1.00 (t, J=7.15 Hz, 6H), 1.61 (m, 2H), 1.71 (m, 2H), 2.51 (m, 6H), 3.62 (m, 2H), 6.10 (t, J=5.20 Hz, 1H), 7.20 (dd, J=5.13, 3.66 Hz, 1H), 7.52 (m, 3H), 7.59 (d, J=5.12 Hz, 1H), 7.69 (d, J=3.66 Hz, 1H), 7.71 (d, J=9.03 Hz, 1H), 8.00 (m, 3H), 8.51 (d, J=6.60 Hz, 1H); Anal. Calcd for $C_{26}H_{30}N_4S_2O_2$: C, 63.13; H, 6.11; N, 11.33; Found: C, 62.98; H, 6.08; N, 10.96.

EXAMPLE 32

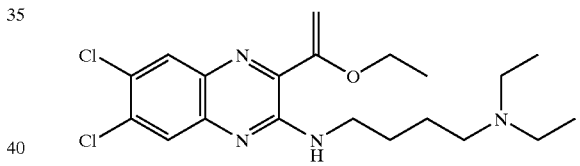

The title compound was prepared according to the experimental procedure for Example 16 using Intermediate h, and was obtained as a yellow-orange oil; $^1$H NMR (CDCl$_3$) 1.04 (m, 6H), 1.24 (m, 6H), 1.69 (m, 4H), 2.04 (m, 1H), 2.29 (m, 1H), 2.55 (m, 6H), 3.51 (m, 2H), 3.64 (m, 1H), 3.81 (m, 11), 6.67 (s, 1H), 7.08 (s, 1H), 3.37 (broad t, J=4.59 Hz, 1H), 7.68 (s, 1H), 7.76(s, 1H); Anal. Calcd for $C_{20}H_{28}N_4Cl_2O_1$: C, 58.39; H, 6.86; N, 13.62; Found: C, 58.49; H, 6.71; N, 13.28.

EXAMPLE 33

N'-(6,7-Dichloro-3-thiazol-2-yl-quinoxalin-2-yl)-N,N-dimethyl-propane-1,3-diamine

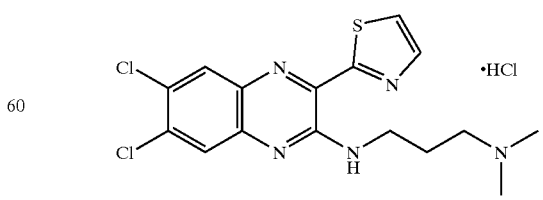

The title compound was prepared according to the experimental procedure for Example 14 using Intermediate g, and the free base converted into the HCl salt by treating it with EtOAc.HCl (39.5%). The salt is a yellow solid; $^1$H NMR (DMSO) 2.08 (m, 2H), 2.74 (d, J=4.95 Hz, 6H), 3.14 (m, 2H), 3.57 (m, 2H), 7.59 (m, 1H), 7.87 (s, 1H), 8.05 (s, 1H), 8.70 (s, 1H), 7.37 (s, 1H), 10.59 (broad s, 1H); Anal. Calcd for $C_{16}H_{17}N_5Cl_2S_1$.(1.5)HCl: C, 44.14; H, 4.23; N, 16.02; Found: C, 44.14; H, 4.23; N, 16.02.

EXAMPLE 34

N'-(3-[2,2']Bithiophenyl-5-yl-6,7-dichloro-quinoxalin-2-yl)-N,N-diethyl-butane-1,4-diamine mp ca 180° C.

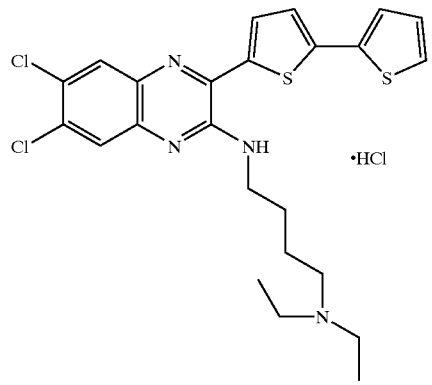

EXAMPLE 35

N'-[6,7-Dichloro-3-(5-chloro-thiophen-2-yl)-quinoxalin-2-yl]-N,N-diethyl-butane-1,4-diamine mp 98–100° C.

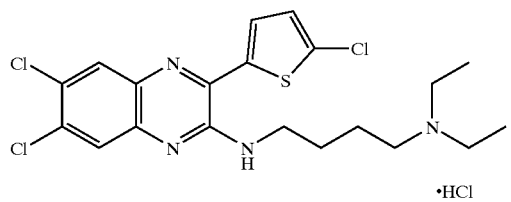

EXAMPLE 36

N'-[6,7-Dichloro-3-(5-methoxy-thiophen-2-yl)-quinoxalin-2-yl]-N,N-diethyl-butane-1,4-diamine glass

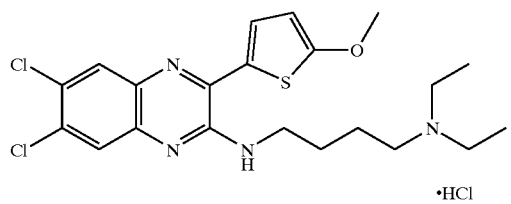

EXAMPLE 37

N'-[6,7-Dichloro-3-(5-propyl-thiophen-2-yl)-quinoxalin-2-yl]-N,N-diethyl-butane-1,4-diamine mp 165–167° C.

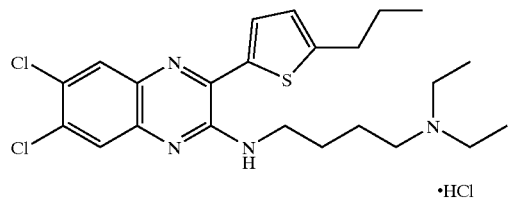

EXAMPLE 38

N'-(3-Benzofuran-2-yl-6,7-dichloro-quinoxalin-2-yl)-N,N-diethyl-butane-1,4-diamine mp 220° C.

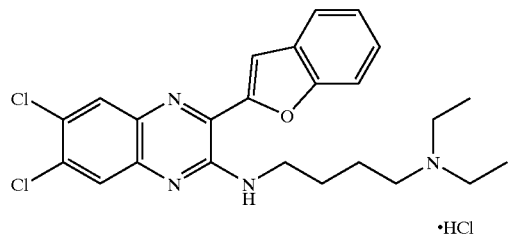

EXAMPLE 39

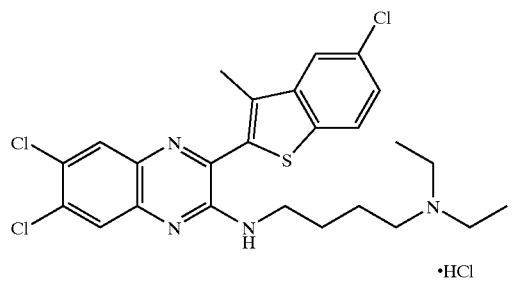

mp 132° C.

EXAMPLE 40

N'-(6,7-Dichloro-3-dibenzothiophen-4-yl-quinoxalin-2-yl)-N,N-diethyl-butane-1,4-diamine mp 134–136° C.

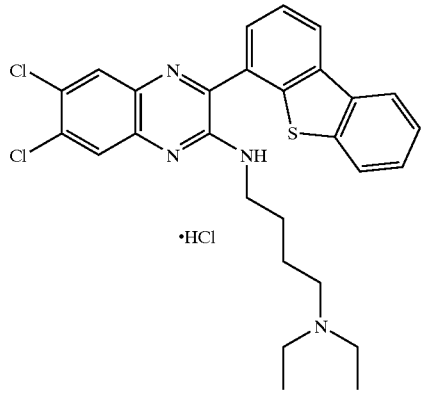

EXAMPLE 41

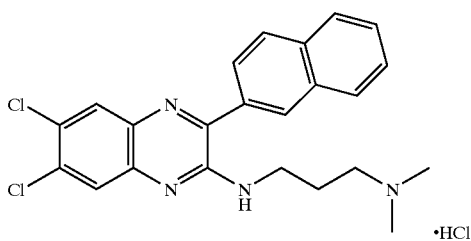

mp 260–262° C.

EXAMPLE 42

[6,7-Dichloro-3-(5-phenyl-oxazol-2-yl)-quinoxalin-2-yl]-(4-pyrrolidin-1-yl-butyl)-amine

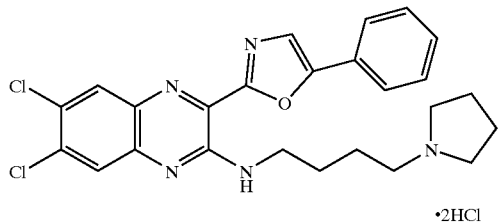

A solution of aminoquinoxaline bromide (159 mg, 0.38 mmol) in anhydrous THF (10 mL) was treated with 5-phenyloxazole (73 mg, 0.5 mmol), $PdCl_2(PPh_3)_2$ (18 mg, 0.025 mol), CuI (10 mg, 0.05 mmol), and potassium acetate (74 mg, 0.75 mmol). The mixture was heated to reflux under argon for 24 hours. Volatiles were removed in vacuo, and the residue was chromatographed on silica gel eluting with 10% $CH_3OH$ and 3% $Et_3N$ in ethyl acetate to give the free base as a viscous oil (80 mg, 44%). The bis.HCl salt was prepared by treating the free base with methanolic HCl; $^1H$ NMR (free base, $CDCl_3$) δ 1.80 (m, 8H), 2.54 (m, 6H), 3.62 (m, 2H), 7.43 (m, 3H), 7.72 (s, 1H), 7.80 (m, 2H), 8.00 (s, 1H), 8.86 (broad t, 1H); Anal. Calcd for $C_{25}H_{25}N_5OCl_2.2HCl.1.9H_2O$: C, 50.93; H, 5.26; N, 11.87; Found: C, 51.13; H, 4.95; N, 11.52.

EXAMPLE 43

[6,7-Dichloro-3-(5-thiophen-2-yl-oxazol-2-yl)-quinoxalin-2-yl]-(4-pyrrolidin-1-yl-butyl)-amine

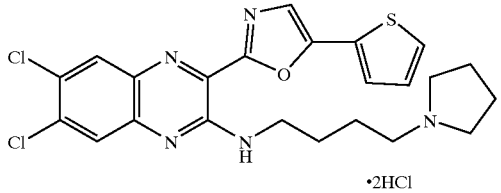

The title compound was prepared according to the experimental procedure for Example 42; $^1H$ NMR (free-base, $CDCl_3$) δ 1.80 (m, 8H), 2.53 (m, 6H), 3.61 (m, 2H), 7.12 (m, 1H), 7.33 (s, 1H), 7.40 (m, 1H), 7.52 (m, 1H), 7.70 (s, 1H), 7.98 (s, 1H), 8.76 (broad t, 1H); Anal. Calcd for: $C_{23}H_{23}N_5OSCl_2.2HCl.H_2O$; C, 47.59; H, 4.86; N, 12.06; Found: C, 47.23; H, 4.86; N, 11.86.

EXAMPLE 44

[6,7-Dichloro-3-(5-pyridin-2-yl-oxazol-2-yl)-quinoxalin-2-yl]-(4-pyrrolidin-1-yl-butyl)-amine

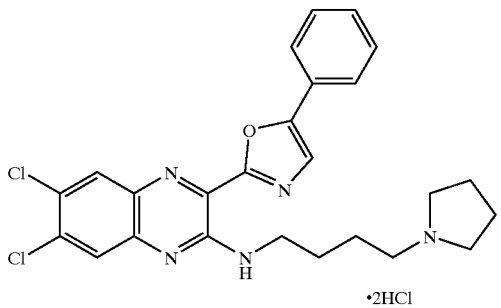

The title compound was prepared according to the experimental procedure for Example 42; $^1H$ NMR (free-base, $CDCl_3$) δ 1.80 (m, 8H), 2.54 (m, 6H), 3.68 (m, 2H), 7.30 (m, 1H), 7.80 (s, 1H), 7.84 (m, 1H), 7.92 (s, 1H), 7.98 (m, 1H), 8.07 (s, 1H), 8.69 (m, 1H), 8.91 (broad t, 1H); Anal. Calcd for: $C_{24}H_{24}ON_6Cl_2.2HCl$; C, 51.81, H, 4.71, N, 15.10; Found: C, 51.66, H, 4.78; N, 14.90.

EXAMPLE 45

[6,7-Dichloro-3-(5-phenyl-thiophen-2-yl)-quinoxalin-2-yl]-(4-pyrrolidin-1-yl-butyl)-amine

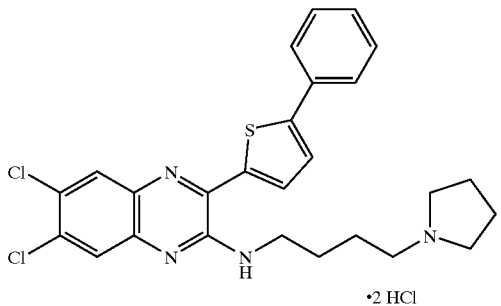

The title compound was prepared according to the experimental procedure for Example 16; $^1H$ NMR (free-base, CDCl$_3$) δ 1.77 (m, 8H), 2.48 (m, 6H), 3.58 (m, 2H), 5.29 (broad t, 1H), 7.40 (m, 4H), 7.67 (m, 3H), 7.78 (s, 1H), 7.94 (s, 1H); Anal. Calcd for C$_{26}$H$_{26}$N$_4$SCl$_2$.2HCl.1.5H$_2$O: C, 52.27; H, 5.22; N, 9.37; Found: C, 52.47; H, 4.85; N, 9.05.

EXAMPLE 46

[6,7-Dichloro-3-(5-phenyl-thiophen-2-yl)-quinoxalin-2-yl]-N,N-dimethyl-butane-1,4-diamine

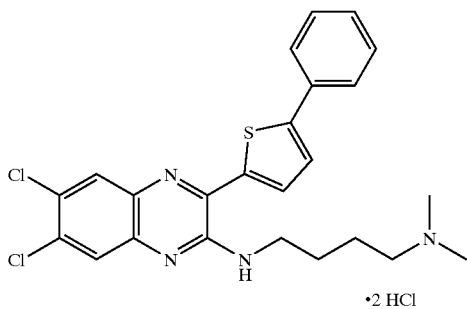

•2 HCl

The title compound was prepared according to the experimental procedure for Example 16, using Intermediate i; $^1$H NMR (free-base, CDCl$_3$) δ 1.65 (m, 2H), 1.76 (m, 2H), 2.13 (s, 6H), 2.30 (t, 2H), 3.54 (q, 2H), 6.43 (broad t, 1H), 7.38 (m, 4H), 7.65 (m, 3H), 7.74 (s, 1H), 7.91 (s, 1H); Anal. Calcd for: C$_{24}$H$_{24}$N$_4$SCl$_2$.2HCl.0.25H$_2$O: C, 52.51, H, 4.86, N, 10.20; Found: C, 52.45, H, 5.02; N, 10.06.

EXAMPLE 47

[6,7-Dichloro-3-methoxy-quinoxalin-2-yl]-(4-pyrrolidin-1-yl-butyl)-amine

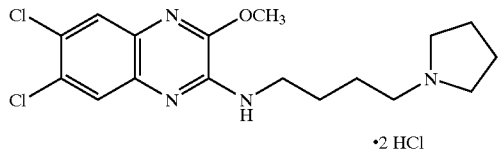

•2 HCl

A solution of aminoquinoxaline bromide (298 mg, 0.70 mmol) in anhydrous THF (10 mL) was treated with methanol (0.085 mL, 2.1 mmol), Et$_3$N (0.190 mL, 1.4 mmol), and Ni(CO)$_2$(PPh$_3$)$_2$ (575 mg, 0.9 mmol). The mixture was heated to reflux for 18 hours, followed by removal of the solvent in vacuo. The residue was chromatographed on silica gel eluting with 10% CH$_3$OH and 3% Et$_3$N in ethyl acetate to give the free base as a viscous oil (194 mg, 74%). The bis.HCl salt was prepared by treating the free base with methanolic HCl; $^1$H NMR (free-base, CDCl$_3$) δ 1.80 (m, 8H), 2.55 (m, 6H), 3.56 (m, 2H), 4.10 (s, 3H), 6.13 (broad s, 1H), 7.70 (m, 2H); Anal. Calcd for: C$_{17}$H$_{22}$N$_4$OCl$_2$.2HCl.2H$_2$O: C, 42.69; H, 5.90; N, 11.71; Found: C, 42.70; H, 5.63; N, 11.60.

EXAMPLE 48

N-(6,7-Dichloro-3-pyridin-3-yl-quinoxalin-2-yl)-N', N'-dimethyl-cyclohexane-1,4-diamine Step (a): Preparation of: Ethyl 3-Pyridylglyoxylate Oxime A solution of sodium ethoxide, which was prepared from metallic sodium (5.0 g) and absolute ethanol (70 mL), was added to anhydrous ethyl ether (300 mL). The resulting solution was placed under a nitrogen atmosphere and cooled in an ice-bath. Ethyl 3-pyridylacetate (35 g) was added to the solution and the resulting mixture stirred 15 minutes, then isoamyl nitrite (25 g) was added dropwise keeping the temperature of the reaction mixture between 5–10° C. After addition was complete, stirring was continued for 1 hour, water (100 mL) was added, and the mixture was acidified with glacial acetic acid. After stirring 1 hour, the precipitate was filtered, washed with ethanol, and dried. Recrystallization from ethanol gave the product as a white solid (5.62 g); mp 162–164° C.

Step (b): Preparation of: 6,7-Dichloro-3-(3-pyridyl)-2-quinoxalinol

A solution of ethyl 3-pyridylglyoxylate oxime (3.35 g) and 4,5-dichlorophenylenediamine (3.05 g) in 35% sulfuric acid (75 mL) was stirred at 75° C. for 17 hours. The solid, which formed on heating, was removed by filtration and triturated in water. Triturating in ethanol gave the product as a light brown solid (3.89 g).

Step (c): Preparation of: 2,6,7-Trichloro-3-pyridin-3-yl-quinoxaline

A slurry of 6,7-dichloro-3-(3-pyridyl)-2-quinoxalinol (3.5 g) in phosphorous oxychloride (35 mL) was refluxed for 6 hours. The resulting mixture was cooled, poured over ice, stirred 5 minutes, and made basic with concentrated NH$_4$OH. The precipitate was removed by filtration and recrystallization in ethanol gave the product as white crystals (2.3 g); mp 174–175° C.

Step (d): Preparation of: N-(6,7-Dichloro-3-pyridin-3-yl-quinoxalin-2-yl)-N',N'-dimethyl-cyclohexane-1,4-diamine A solution of 2,6,7-trichloro-3-pyridin-3-yl-quinoxaline (1.0 g) and N,N-dimethyl-cyclohexane-1,4-diamine in toluene (25 mL) was refluxed for 24 hours. After refluxing, the reaction mixture was cooled, filtered, and concentrated under vacuum. The residue was purified by flash chromatography (silica gel, 1:9 methanol/dichloromethane) to give the product as a yellow solid (0.43 g); mp 158–161° C.

EXAMPLE 49

N-(6,7-Dichloro-3-pyridin-4-yl-quinoxalin-2-yl)-N', N'-dimethyl-cyclohexane-1,4-diamine Step (a): Preparation of: Ethyl 4-Pyridylglyoxylate Oxime A solution of sodium ethoxide, which was prepared from metallic sodium (3.5 g) and absolute ethanol (50 mL), was added to anhydrous ethyl ether (200 mL). The resulting solution was placed under a nitrogen atmosphere and cooled in an ice-bath. Ethyl 4-pyridylacetate (25 g) was added to the solution and the resulting mixture stirred 15 minutes, then isoamyl nitrite (25 mL) was added dropwise keeping the temperature of the reaction mixture between 5–10° C. After addition was complete, stirring was continued for 1 hour, water (50 mL) was added, and the mixture was acidified with glacial acetic acid. After stirring 1 hour, the precipitate was filtered, washed with ethanol, and dried. Recrystallization from ethanol gave the product as a white solid (9.76 g).

Step (b): Preparation of: 6,7-Dichloro-3-(4-pyridyl)-2-quinoxalinol

A solution of ethyl 4-pyridylglyoxylate oxime (3.35 g) and 4,5-dichlorophenylenediamine (3.05 g) in 35% sulfuric acid (75 mL) was stirred at 75° C. for 16 hours. The solid, which formed on heating, was removed by filtration and triturated in water. The remaining solid was filtered, dissolved in hot ethanol, and made basic with concentrated NH$_4$OH. This mixture was cooled and diluted with water. The precipitate was collected by filtration and recrystallized from ethanol to give the product as a gray solid (6.20 g).

Step (c): Preparation of: 2,6,7-Trichloro-3-pyridin-4-yl-quinoxaline

A slurry of 6,7-dichloro-3-(3-pyridyl)-2-quinoxalinol (3.5 g) in phosphorous oxychloride (35 mL) was refluxed for 6 hours. The resulting mixture was cooled, poured over ice, stirred for 15 minutes, and made basic with concentrated $NH_4OH$. The precipitate was removed by filtration and recrystallization from ethanol gave the product as white crystals (0.62 g).

Step (d): Preparation of: N-(6,7-Dichloro-3-pyridin-4-yl-quinoxalin-2-yl)-N',N'-dimethyl-cyclohexane-1,4-diamine A solution of 2,6,7-trichloro-4-pyridin-3-yl-quinoxaline (0.31 g) and N,N-dimethyl-cyclohexane-1,4-diamine (0.28 g) in toluene (30 mL) was refluxed under nitrogen atmosphere for 24 hours. Potassium carbonate (0.14 g) was added to the reaction and the reaction mixture refluxed an additional 24 hours. The reaction mixture was cooled, filtered, and concentrated under vacuum. The residue was purified by flash chromatography (silica gel, 1:9 methanol/dichloromethane) to give a yellow solid. This solid was recrystallized from methanol to give the product as yellow crystals (0.078 g); mp 183–185° C.

EXAMPLE 50

N-(6,7-Dimethoxy-3-pyridin-2-yl-quinoxalin-2-yl)-N',N'-dimethyl-cyclohexane-1,4-diamine Step (a): Preparation of: 6,7-Dimethoxy-3-(2-pyridyl)-2-quinoxalinol A solution of ethyl 2-pyridylglyoxylate oxime (3.35 g) and 4,5-dimethoxyphenylenediamine (3.05 g) in 35% sulfuric acid (75 mL) was stirred at 75° C. for 17 hours. The solid, which formed on heating, was removed by filtration and dissolved in water. The solution was adjusted to pH 8 with concentrated $NH_4OH$. The precipitate removed by filtration and washed with water. This solid was recrystallized from ethanol to give the product as a light brown solid (3.64 g).

Step (b): Preparation of: 2-Chloro-6,7-dimethoxy-3-pyridin-2-yl-quinoxaline

A slurry of 6,7-dimethoxy-3-(2-pyridyl)-2-quinoxalinol (2.0 g) in phosphorous oxychloride (20 mL) was refluxed for 18 hours. The resulting mixture was cooled, poured over ice, stirred for 5 minutes, and made basic with concentrated $NH_4OH$. The precipitate was removed by filtration and purified by flash chromatography (silica gel, 1:9 methanol/dichloromethane) to give the product as white solid (1.6 g); mp 146–147° C.

Step (c): Preparation of: N-(6,7-Dimethoxy-3-pyridin-2-yl-quinoxalin-2-yl)-N',N'-dimethyl-cyclohexane-1,4-diamine A solution of 2-chloro-6,7-dimethoxy-3-pyridin-2-yl-quinoxaline (0.91 g) and N,N-dimethyl-cyclohexane-1,4-diamine (0.86 g) in toluene (30 mL) was refluxed under nitrogen atmosphere for 16 hours. The reaction mixture was cooled, filtered, and concentrated under vacuum. The residue was purified by flash chromatography (silica gel, 1:9 methanol/dichloromethane) to give a yellow solid. This solid was recrystallized in ethyl acetate/hexane to give the product as yellow crystals (0.92 g); mp 168–171° C.

EXAMPLE 51

N,N-Dimethyl-N'-(3-pyridin-2-yl-7,8-dihydro-6H-cyclopenta[g]quinoxalin-2yl)-cyclohexane-1,4-diamine Step (a): Preparation of: 5,6-Diaminoindane A solution of 5-amino-6-nitroindane (2.0 g) in THF (200 mL) was hydrogenated at room temperature over a Raney nickel catalyst (1.0 g) for 4 hours. The catalyst was removed by filtration and the filtrate evaporated. Recrystallization of the residue from methanol and water gave the product as pale purple crystals (1.53 g).

Step (b): Preparation of: 3-Pyridin-2-yl-7,8-dihydro-6H-cyclopenta[g]quinoxalinol A solution of ethyl 2-pyridylglyoxylate oxime (1.86 g) and 5,6-diaminoindane (1.42 g) in 35% sulfuric acid (33 mL) was stirred at 75° C. for 16 hours. The solid, which formed on heating, was removed by filtration and dissolved in water. The solution was adjusted to pH 8 with concentrated $NH_4OH$, the precipitate removed by filtration and washed with water. This solid was recrystallized from ethanol to give the product as a pale yellow solid (1.29 g).

Step (c): Preparation of: 2-Chloro-3-pyridin-2-yl-7,8-dihydro-6H-cyclopenta[g]quinoxaline A slurry of 3-pyridin-2-yl-7,8-dihydro-6H-cyclopenta[g]quinoxalinol (1.0 g) in phosphorous oxychloride (20 mL) was refluxed for 16 hours. The resulting mixture was cooled, poured over ice, stirred for 5 minutes, and made basic with concentrated $NH_4OH$. The precipitate was removed by filtration and purified by flash chromatography (silica gel, dichloromethane) to the product as light brown powder (1.6 g).

Step (d): Preparation of: N,N-Dimethyl-N'-(3-pyridin-2-yl-7,8-dihydro-6H-cyclopenta[g]quinoxalin-2yl)-cyclohexane-1,4-diamine A solution of 2-chloro-3-pyridin-2-yl-7,8-dihydro-6H-cyclopenta[g]quinoxaline (0.5 g) and N,N-dimethyl-cyclohexane-1,4-diamine (0.51 g) in toluene (30 mL) was refluxed under nitrogen atmosphere for 16 hours. The reaction was cooled, filtered, and concentrated under vacuum. The residue was purified by flash chromatography (silica gel, 1:19 methanol/dichloromethane) to give a yellow solid. Recrystallization from methanol and water gave the product as yellow crystals ( 0.3 g); mp 158–161° C.

EXAMPLE 52

N'-(6,7-Dichloro-3-pyridin-2-yl-quinoxalin-2-yl)-N,N-dimethyl-ethane-1,2-diamine A solution of 2,6,7-trichloro-3-pyridin-2-yl-quinoxaline (0.50 g) and N,N-dimethyl-ethane-1,2-diamine (0.28 g) in toluene (20 mL) was refluxed under nitrogen atmosphere for 16 hours. After refluxing, the reaction mixture was cooled, filtered, and concentrated under vacuum. The residue was purified by flash chromatography (silica gel, 1:9 methanol/dichloromethane) to give the product as a yellow solid (0.26 g); mp 95–97° C.

EXAMPLE 53

N'-(6,7-Dichloro-3-pyridin-2-yl-quinoxalin-2-yl)-N,N-dimethyl-propane-1,3-diamine A solution of 2,6,7-trichloro-3-pyridin-2-yl-quinoxaline (0.50 g) and 3-N,N-dimethylamino-propylamine (0.32 g) in toluene (20 mL) was refluxed under nitrogen for 16 hours. After refluxing, the reaction mixture was cooled, filtered, and concentrated under vacuum. The residue was purified by flash chromatography (silica gel, 1:9 methanol/dichloromethane) to give the product as a yellow solid (0.43 g); mp 59–61° C.

EXAMPLE 54

N'-(6,7-Dichloro-3-pyridin-2-yl-quinoxalin-2-yl)-N,N-dimethyl-butane-1,4-diamine A solution of 2,6,7-trichloro-3-pyridin-2-yl-quinoxaline (0.50 g) and 4-N,N-dimethlyamino-butylamine (0.36 g) in toluene (20 mL) was refluxed under nitrogen for 16 hours. After refluxing, the reaction mixture was cooled, filtered, and concentrated under vacuum. The residue was purified by flash chromatography (silica gel, 1:9 methanol/ dichloromethane) to give a yellow solid. Recrystallization from methanol and water gave the product as yellow crystals (0.34 g); mp 81–83° C.

EXAMPLE 55

N'-(6,7-Dichloro-3-pyridin-2-yl-quinoxalin-2-yl)-N, N-dimethyl-pentane-1,5-diamine Step (a): Preparation of: (5-Amino-pentyl)-carbamic Acid tert-Butyl Ester To a solution of putrescine (5.2 g) in dry THF (150 mL) at 0° C. under nitrogen atmosphere was added a chilled solution of di-tert-butyl dicarbonate (3.7 g) in THF (100 mL). When the addition was complete, the resulting mixture was warmed to room temperature and stirred 1 hour. The reaction mixture was quenched with water and extracted with ethyl acetate. The combined extracts were washed with water and brine. The organic phase was dried over $MgSO_4$ and concentrated under vacuum to give the product as a waxy white solid (2.8 g). (Blagbroug I. S., Moya E., Walford S. P., *Tetrahedron. Letters*, 1996;37:551.)

Step (b): Preparation of: [N-(6,7-Dichloro-3-pyridin-2-yl-quinoxalin-2-yl-5-amino-pentyl]-carbamic Acid tert-Butyl Ester A solution of 2,6,7-trichloro-3-pyridin-2-yl-quinoxaline (2.2 g) and (5-amino-pentyl)-carbamic acid tert-butyl ester (2.8 g) in toluene (50 mL) was refluxed under nitrogen atmosphere for 16 hours. After refluxing, the reaction mixture was cooled, filtered, and concentrated under vacuum. The residue was purified by flash chromatography (silica gel, 1:9 methanol/dichloromethane) to give a yellow solid. Recrystallization from ethanol and water gave the product as a yellow solid (2.1 g).

Step (c): Preparation of: N-(6,7-Dichloro-3-pyridin-2-yl-quinoxalin-2-yl)-pentane-1,5-diamine

[N-(6,7-Dichloro-3-pyridin-2-yl-quinoxalin-2-yl)-5-amino-pentyl]-carbamic acid tert-butyl ester (1.0 g) was placed in a solution of hydrochloride gas in methanol and stirred 2 hours. The reaction mixture was treated with 2N KOH solution, stirred, and diluted with water. This mixture was filtered to give the product as a yellow solid (0.98 g).

Step (d): Preparation of: N'-(6,7-Dichloro-3-pyridin-2-yl-quinoxalin-2-yl)-N,N-dimethyl-pentane-1,5-diamine A solution of N-(6,7-trichloro-3-pyridin-2-yl-quinoxalin-2-yl)-pentane-1,5-diamine (0.98 g) and formic acid (0.83 g) in formalin (7.5 mL) was heated on a steam bath for 16 hours. This mixture was diluted with methanol (30 mL) and treated with 2N HCl solution. After stirring 20 minutes, 2N KOH solution was added. The precipitate was collected by filtration and purified by flash chromatography (silica gel, 1:9 methanol/dichloromethane) to give a yellow solid. Recrystallization from methanol and water gave the product as a yellow powder (0.083 g); mp 100–102° C.

EXAMPLE 56

N'-(6,7-Dichloro-3-pyridin-2-yl-quinoxalin-2-yl)-N, N-dimethyl-hexane-1,6-diamine A solution of 2,6,7-trichloro-3-pyridin-2-yl-quinoxaline (0.50 g) and 6-dimethylamino-hexylamine (0.46 g) in toluene (25 mL) was refluxed under nitrogen atmosphere for 16 hours. After refluxing, the reaction mixture was cooled, filtered, and concentrated under vacuum. The residue was purified by flash chromatography (silica gel, 1:9 methanol/ dichloromethane) to give a yellow solid. Recrystallization from methanol and water gave the product as a fluffy yellow powder (0.41 g); mp 88–90° C.

EXAMPLE 57

[3-(6,7-Dichloro-3-pyridin-2-yl-quinoxalin-2-ylsulfanyl-propyl]-dimethylamine

To a solution 2,6,7-trichloro-3-pyridin-2-yl-quinoxaline (0.50 g) and dimethylaminopropanethiol hydrochloride (0.25 g) in toluene (20 mL) was added pyridine (0.25 mL). The resulting mixture was refluxed under nitrogen atmosphere for 16 hours. After refluxing, the reaction mixture was cooled, filtered, and concentrated under vacuum. The residue was purified by flash chromatography (silica gel, 1:9 methanol/dichloromethane) to give a yellow solid. Recrystallization from methanol and water gave the product as a fluffy yellow powder (0.25 g); mp 82–84° C.

EXAMPLE 58

(6,7-Dichloro-3-pyridin-2-yl-quinoxalin-2-yl)-(3-morpholin-4-yl-propyl)-amine

A solution of 2,6,7-trichloro-3-pyridin-2-yl-quinoxaline (0.50 g) and N-(3-aminopropyl)-morpholine (0.46 g) in toluene (25 mL) was refluxed under nitrogen for 16 hours. After refluxing, the reaction mixture was cooled, filtered, and concentrated under vacuum. The residue was purified by flash chromatography (silica gel, 1:9 methanol/ dichloromethane) to give a yellow solid. Recrystallization from methanol and water gave the product as yellow crystals (0.56 g); mp 119–121° C.

EXAMPLE 59

(6,7-Dichloro-3-pyridin-2-yl-quinoxalin-2-yl)-(3-methoxypropyl)-amine

A solution of 2,6,7-trichloro-3-pyridin-2-yl-quinoxaline (0.50 g) and 3-methoxy-propylamine (0.28 g) in toluene (20 mL) was refluxed under nitrogen for 16 hours. After refluxing, the reaction mixture was cooled, filtered, and concentrated under vacuum. The residue was recrystallized from methanol and water to give the product as a yellow solid (0.45 g); mp 99.5–100.5° C.

EXAMPLE 60

N'-1-[3-(6,7-Dichloro-3-pyridin-2-yl-quinoxalin-2-ylamino)-propyl]-N'-1-methyl-propane-1,3-diamine Step (a): Preparation of: {3-[(3-Amino-propyl)-methyl-amino]-propyl}-carbamic Acid tert-Butyl Ester To a solution of 3,3-diamino-N-methyldipropylamine (4.4 g) in dry THF (70 mL) at 0° C. under nitrogen was added a chilled solution of di-tert-butyl dicarbonate (2.2 g) in THF (75 mL). When the addition was complete, the resulting mixture was slowly warmed to room temperature and stirred 1 hour. The reaction mixture was quenched with water and extracted with ethyl acetate. The combined extracts were washed with water and brine. The organic phase was dried over sodium sulfate then concentrated under vacuum to give the product as waxy white solid (2.3 g).

Step (b): Preparation of: N'-1-[3-(6,7-Dichloro-3-pyridin-2-yl-quinoxalin-2-ylamino)-propyl]-N'-1-methyl-propane-1, 3-diamine A solution of 2,6,7-trichloro-3-pyridin-2-yl-quinoxaline (0.90 g) and {3-[(3-amino-propyl)-methyl-amino]-propyl}- carbamic acid tert-butyl ester (0.1.4 g) in toluene (30 mL) was refluxed under nitrogen atmosphere for 16 hours. After refluxing, the reaction mixture was cooled and filtered, then treated with HCl gas. The precipitate was collected by filtration, dissolved in chloroform, and washed with 10% aqueous potassium carbonate solution. The organic phase was concentrated under vacuum, and the residue was purified by flash chromatography (silica gel, 1:9 methanol/dichloromethane) to give the product as a brown oil (0.62 g).

EXAMPLE 61

2-{[3-(6,7-Dichloro-3-pyridin-2-yl-quinoxalin-2-ylamino)-propyl]-(2-hydroxy-ethyl)-amino}-ethanol A solution of 2,6,7-trichloro-3-pyridin-2-yl-quinoxaline (0.50 g) and 3-[bis(2-hydroxy-ethyl)amino]-propylamine (0.51 g) in toluene (25 mL) was refluxed under nitrogen atmosphere for 16 hours. After refluxing, the reaction mixture was cooled, filtered, and concentrated under vacuum. The residue was purified by flash chromatography (silica gel, 1:9 methanol/dichloromethane) to give a yellow solid. Recrystallization from methanol and water gave the product as a yellow plate like crystals (0.55 g); mp 88–90° C.

EXAMPLE 62

{4-[4-(2-Chloro-phenyl)-piperidin-1-yl]-butyl-(6,7-dichloro-3-pyridin-2-yl-quinoxalin-2-yl)}amine A solution of 2,6,7-trichloro-3-pyridin-2-yl-quinoxaline (0.31 g) and 4-[(2-chloro-phenyl)-1-piperazine]butylamine (0.53 g) in toluene (25 mL) was refluxed under nitrogen atmosphere for 16 hours. After refluxing, the reaction mixture was cooled, filtered, and concentrated under vacuum. The residue was purified by flash chromatography (silica gel, 1:9 methanol/dichloromethane) to give a brown solid. Recrystallization from methanol and water gave the product as a yellow crystals (0.29 g); mp 116–118° C.

EXAMPLE 63

(6,7-Dichloro-3-pyridin-2-yl-quinoxalin-2-yl)-(1-phenyl-4-piperdin-1-yl-butyl)-amine To a solution 2,6,7-trichloro-3-pyridin-2-yl-quinoxaline (0.31 g) and alpha-phenyl-1-piperdine-butylamine dihydrochloride (0.31 g) in toluene (25 mL) was added triethylamine (0.50 mL). The resulting mixture was refluxed under nitrogen atmosphere for 36 hours. After refluxing, the reaction mixture was cooled, filtered, and concentrated under vacuum. The residue was purified by flash chromatography (silica gel, 1:9 methanol/dichloromethane) to give a yellow solid. Recrystallization from methanol and water gave the product as a fluffy yellow powder (0.32 g); mp 125–127° C.

EXAMPLE 64

(6,7-Dichloro-3-(1-ethyl-5-phenyl-imidazol-2-yl)-quinoxalin-2-yl)]-(4-pyrrolidin-1-yl-butyl)-amine

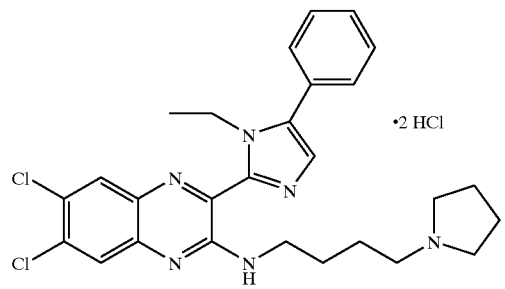

A solution of 1-ethyl-5-phenylimidazole (220 mg, 1.28 mmol) in anhydrous THF (10 mL) was cooled in an ice bath and treated with n-butyllithium (2.5 M, 0.56 mL, 1.41 mmol), and stirred for 30 minutes. The resulting brown solution was treated with anhydrous $ZnCl_2$ (354 mg, 2.6 mmol) in THF (10 mL) and allowed to warm to room temperature. After 30 minutes, the resulting organozinc reagent was treated with aminoquinoxaline bromide and catalyst $(PdCl_2(PPh_3)_2$ 42 mg, 0.06 mmol and n-butyllithium 0.048 mL, 0.12 mmol in anhydrous THF (3 mL). The mixture was heated to reflux for 18 hours, followed by removal of the solvent in vacuo. The residue was chromatographed on silica gel eluting with 10% $CH_3OH$ and 3% $Et_3N$ in ethyl acetate to give the free base as a viscous oil (67 mg, 20%). The bis.HCl salt was prepared by treating the free base with methanolic HCl; $^1H$ NMR (free-base, $CDCl_3$) δ 1.38 (t, 3H), 1.80 (m, 8H), 2.55 (m, 6H), 3.65 (m, 2H), 4.65 (m, 2H), 7.18 (m, 1H), 7.46 (m, 5H), 7.73 (s, 1H), 7.81 (s, 2H), 10.16 (broad s, 1H); Anal. Calcd for $C_{27}H_{30}N_6Cl_2.2HCl$: C, 55.7; H, 5.53; N, 14.43. Found: C, 56.15; H. 5.73; N, 14.08.

EXAMPLE 65

[6,7-Dichloro-3-(1-phenyl-imidazol-2-yl)-quinoxalin-2-yl]-(4-pyrrolidin-1-yl-butyl)-amine

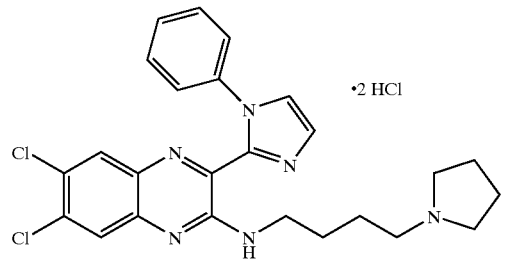

The title compound was prepared according to the experimental procedure for Example 64; $^1H$ NMR (free-base, $CDCl_3$) δ 1.80 (m, 8H), 2.60 (m, 6H), 3.64 (m, 2H), 7.02 (m, 1H), 7.30 (m, 4H), 7.45 (m, 3H), 7.68 (m, 1H), 9.66 (broad s, 1H); Anal. Calcd for $C_{25}H_{26}N_6Cl_2.2HCl.0.6H_2O.0.3CH_3OH$: C, 52.86; H, 5.33; N, 14.62. Found: C, 53.02; H, 5.27; N, 14.24.

EXAMPLE 66

[6,7-Dichloro-3-[1-ethyl-5-(5-methyl-thiophene-2-yl)-imidazol-5-yl]-quinoxalin-2-yl]-(4-pyrrolidin-1-yl-butyl)-amine

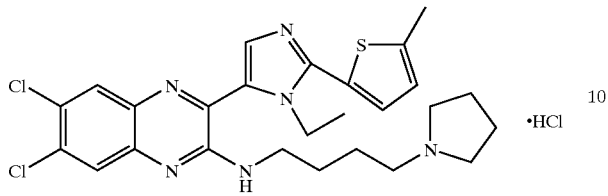

The title compound was prepared according to the experimental procedure for Example 64; $^1$H NMR (free-base, CDCl$_3$) δ 1.50 (t, 3H), 1.76 (m, 8H), 2.50 (s, 9H), 3.63 (q, 2H), 4.72 (q, 2H), 6.81 (d, 1H), 6.99 (d, 1H), 7.22 (s, 1H), 7.73 (s, 1H), 7.82 (s, 1H), 10.04 (broad t, 1H); Anal. Calcd for C$_{26}$H$_{30}$N$_6$SCl$_2$.HCl.H$_2$O.0.8CH$_3$OH: C, 52.80; H, 5.98; N, 13.78. Found: C, 52.47; H, 5.51; N, 13.51.

EXAMPLE 67

[6,7-Dichloro-3-(1-phenyl-pyrazol-5-yl)-quinoxalin-2-yl]-(4-pyrrolidin-1-yl-butyl)-amine

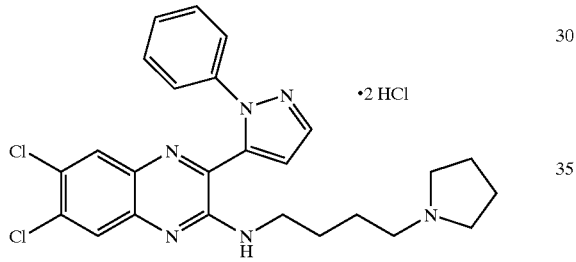

The title compound was prepared according to the experimental procedure for Example 16; $^1$H NMR (free-base, CDCl$_3$) δ 1.53 (m, 4H), 1.75 (m, 4H), 2.44 (m, 6H), 3.41 (m, 2H), 5.29 (m, 1H), 6.81 (d, j=1.8 Hz, 1H), 7.29 (m, 5H), 7.77 (s, 1H), 7.78 (s, 1H), 7.86 (d, j=1.8 Hz, 1H); Anal. Calcd for C$_{25}$H$_{26}$N$_6$Cl$_2$.2HCl.H$_2$O: C, 52.46; H, 5.28; N, 14.68. Found: C, 53.18; H, 5.23; N, 14.39.

What is claimed is:

1. A compound of Formula I:

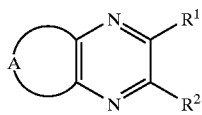

wherein A is

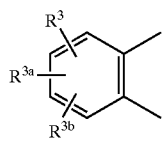

wherein R$^3$, R$^{3a}$, and R$^{3b}$ are each independently the same or different and are hydrogen, alkyl, aryl-SO$_2$—, aryl, heteroaryl, —OR$^4$ wherein R$^4$ is hydrogen, alkyl, aryl, aralkyl, acetyl, or

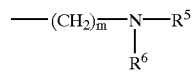

wherein

R$^5$ and R$^6$ are each the same or different and are hydrogen, alkyl, cycloalkyl, acetyl, —(CH$_2$)$_m$—OH, or R$^5$ and R$^6$ are taken together to form a 5- to 7-membered ring optionally containing an oxygen atom or N—R$^4$ wherein R$^4$ is as defined above and m is an integer of 2 to 5,

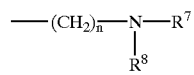

wherein n is zero or an integer of 1 and R$^7$ and R$^8$ are each independently the same or different and are hydrogen, alkyl, aryl, aralkyl, acetyl, or

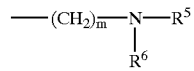

wherein R$^5$ and R$^6$ are as defined above or R$^7$ and R$^8$ taken together to form a 5- to 7-membered ring optionally containing an oxygen atom or N—R$^4$ wherein R$^4$ and m are as defined above,

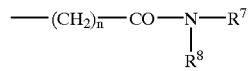

wherein R$^7$, R$^8$, and n are as defined above,

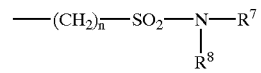

wherein R$^7$, R$^8$, and n are as defined above,

—(CH$_2$)$_n$—SO$_2$OR$^4$ wherein R$^4$ and n are as defined above,

—(CH$_2$)$_n$—CO$_2$R$^4$ wherein R$^4$ and n are as defined above,

—CH$_2$OR$^4$ wherein R$^4$ is as defined above,
halogen,
CF$_3$,
CBr$_3$,
CCl$_3$, or
NO$_2$;

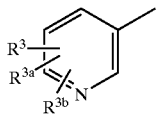

wherein R$^3$, R$^{3a}$, and R$^{3b}$ are as defined above,

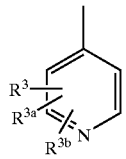

wherein R$^3$, R$^{3a}$, and R$^{3b}$ are as defined above,

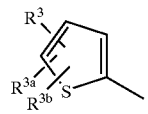

wherein R$^3$, R$^{3a}$, and R$^{3b}$ are as defined above,

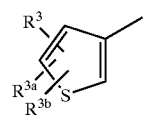

wherein R$^3$, R$^{3a}$, and R$^{3b}$ are as defined above,

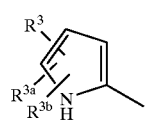

wherein R$^3$, R$^{3a}$, and R$^{3b}$ are as defined above,

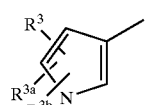

wherein R$^3$, R$^{3a}$, and R$^{3b}$ are as defined above,

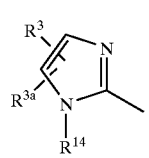

wherein R$^{14}$ is hydrogen, alkyl, aryl, or aralkyl, and R$^3$ and R$^{3a}$ are as defined above,

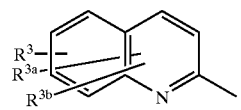

wherein R$^3$, R$^{3a}$, and R$^{3b}$ are as defined above,

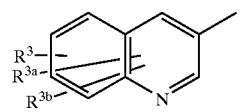

wherein R$^3$, R$^{3a}$, and R$^{3b}$ are as defined above,

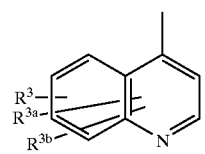

wherein R$^3$, R$^{3a}$, and R$^{3b}$ are as defined above,

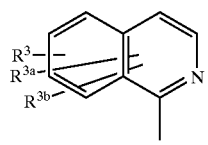

wherein R$^3$, R$^{3a}$, and R$^{3b}$ are as defined above,

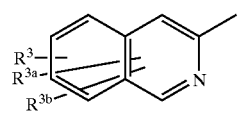

wherein R$^3$, R$^{3a}$, and R$^{3b}$ are as defined above,

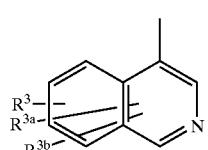

wherein R$^3$, R$^{3a}$, and R$^{3b}$ are as defined above,

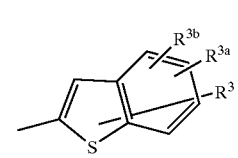

wherein R³, R³ᵃ, and R³ᵇ are as defined above,

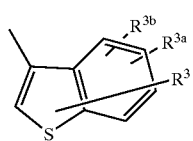

wherein R³, R³ᵃ, and R³ᵇ are as defined above,

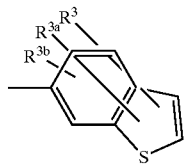

wherein R³, R³ᵃ, and R³ᵇ are as defined above,

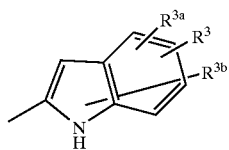

wherein R³, R³ᵃ, and R³ᵇ are as defined above,

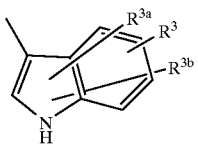

wherein R³, R³ᵃ, and R³ᵇ are as defined above,

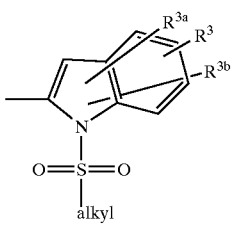

wherein R³, R³ᵃ, and R³ᵇ are as defined above,

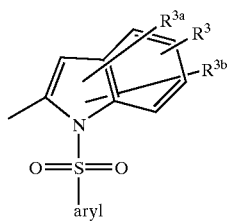

wherein R³, R³ᵃ, and R³ᵇ are as defined above,

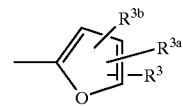

wherein R³, R³ᵃ, and R³ᵇ are as defined above,

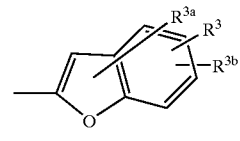

wherein R³, R³ᵃ, and R³ᵇ are as defined above,

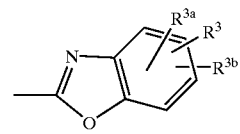

wherein R³, R³ᵃ, and R³ᵇ are as defined above,

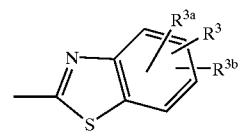

wherein R³, R³ᵃ, and R³ᵇ are as defined above,

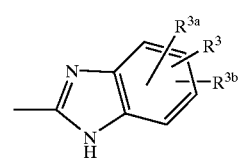

wherein R³, R³ᵃ, and R³ᵇ are as defined above,

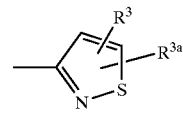

wherein R³ and R³ᵃ are as defined above,

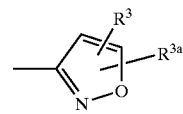

wherein R³ and R³ᵃ are as defined above,

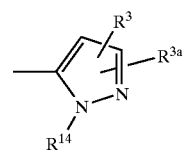

wherein $R^3$, $R^{3a}$, and $R^{14}$ are as defined above,

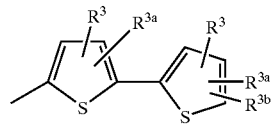

wherein $R^3$, $R^{3a}$, and $R^{3b}$ are as defined above,

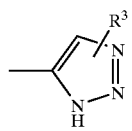

wherein $R^3$ is as defined above,

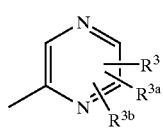

wherein $R^3$, $R^{3a}$, and $R^{3b}$ are as defined above,

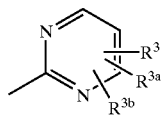

wherein $R^3$, $R^{3a}$, and $R^{3b}$ are as defined above,

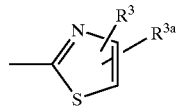

wherein $R^3$ and $R^{3a}$ are as defined above,

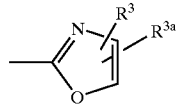

wherein $R^3$ and $R^{3a}$ are as defined above,

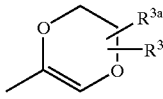

wherein $R^3$ and $R^{3a}$ are as defined above,

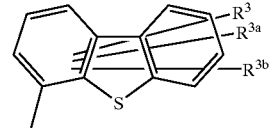

wherein $R^3$, $R^{3a}$, and $R^{3b}$ are as defined above,

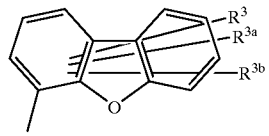

wherein $R^3$, $R^{3a}$, and $R^{3b}$ are as defined above,

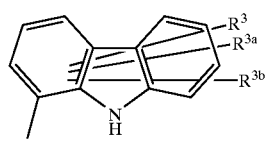

wherein $R^3$, $R^{3a}$, and $R^{3b}$ are as defined above, $R^2$ is $CF_3$,
$CCl_3$,
$CBr_3$, or

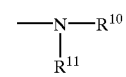

wherein $R^{10}$ is hydrogen,
alkyl, or
aralkyl, and $R^{11}$ is 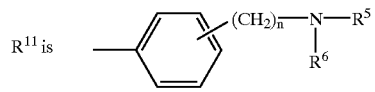

wherein n, $R^5$, and $R^6$ are as defined above,

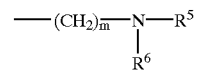

wherein $R^5$, $R^6$, and m are as defined above,

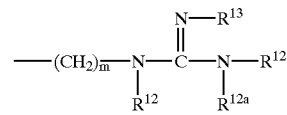

wherein $R^{12}$ and $R^{12a}$ are each independently the same or different and are hydrogen, alkyl, or aryl, or taken together can form a 5- to 7-membered ring, and $R^{13}$ is hydrogen or alkyl, and m is as defined above,

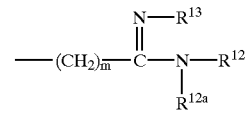

wherein m, $R^{12}$, $R^{12a}$, and $R^{13}$ are as defined above,

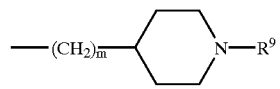

wherein $R^9$ and m are as defined above,

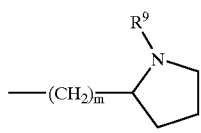

wherein $R^9$ and m are as defined above,

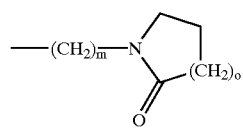

wherein m and o are as defined above,

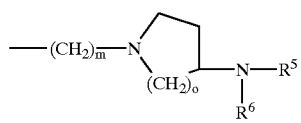

wherein n, o, $R^5$, and $R^6$ are as defined above,

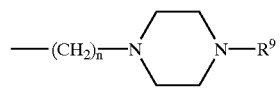

wherein n and $R^9$ are as defined above,

wherein n is as defined above,

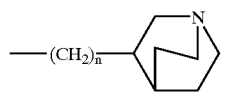

wherein n is as defined above,

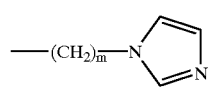

wherein m is as defined above, or $R^{10}$ and $R^{11}$ when taken together can form a 5- to 7-membered ring optionally containing an oxygen atom or N—$R^4$ wherein $R^4$ is as defined above;

or a pharmaceutically acceptable salt thereof.

2. The compound of claim 1 wherein A is:

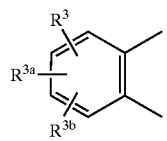

wherein $R^3$, $R^{3a}$, and $R^{3b}$ are each independently the same or different and are hydrogen,
alkyl,
aryl,
heteroaryl,
—$OR^4$ wherein $R^4$ is hydrogen,
  alkyl,
  aryl,
  aralkyl,
  acetyl, or

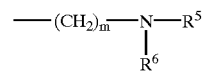

wherein $R^5$ and $R^6$ are each the same or different and are hydrogen, alkyl, cycloalkyl, acetyl, or
$R^5$ and $R^6$ are taken together to form a 5- to 7-membered ring optionally containing an oxygen atom or N—$R^4$ wherein $R^4$ is as defined above and m is an integer of 2 to 5,

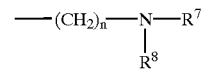

wherein n is zero or an integer of 1 and $R^7$ and $R^8$ are each independently the same or different and are hydrogen, alkyl,
aryl,
aralkyl,
acetyl or

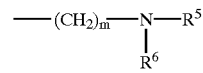

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

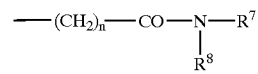

wherein $R^7$, $R^8$, and n are as defined above,

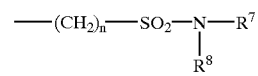

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above, halogen,
CF₃,
CBr₃,
CCl₃, or
NO₂,

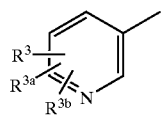

wherein R³, R³ᵃ, and R³ᵇ are as defined above,

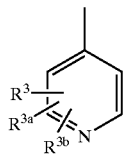

wherein R³, R³ᵃ, and R³ᵇ are as defined above,

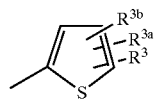

wherein R³, R³ᵃ, and R³ᵇ are as defined above,

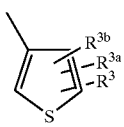

wherein R³, R³ᵃ, and R³ᵇ are as defined above,

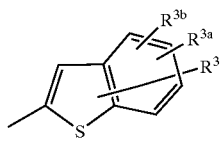

wherein R³, R³ᵃ, and R³ᵇ are as defined above,

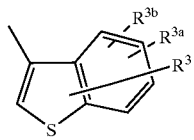

wherein R³, R³ᵃ, and R³ᵇ are as defined above,

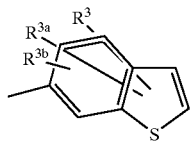

wherein R³, R³ᵃ, and R³ᵇ are as defined above,

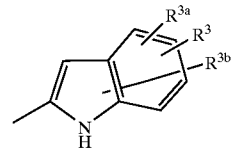

wherein R³, R³ᵃ, and R³ᵇ are as defined above,

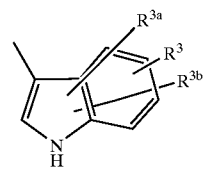

wherein R³, R³ᵃ, and R³ᵇ are as defined above,

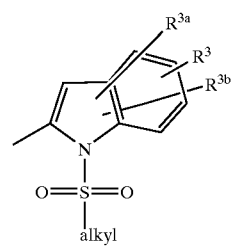

wherein R³, R³ᵃ, and R³ᵇ are as defined above,

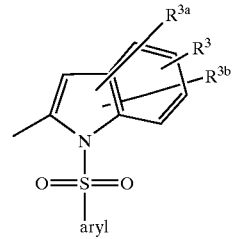

wherein R³, R³ᵃ, and R³ᵇ are as defined above,

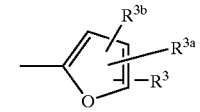

wherein R³, R³ᵃ, and R³ᵇ are as defined above,

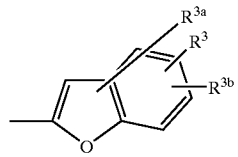

wherein $R^3$, $R^{3a}$, and $R^{3b}$ are as defined above,

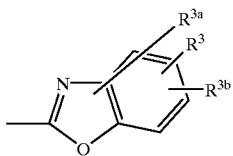

wherein $R^3$, $R^{3a}$, and $R^{3b}$ are as defined above,

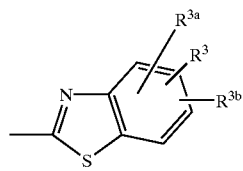

wherein $R^3$, $R^{3a}$, and $R^{3b}$ are as defined above,

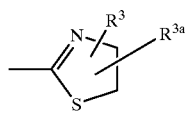

wherein $R^3$ and $R^{3a}$ are as defined above,

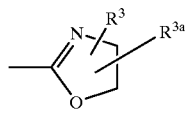

wherein $R^3$ and $R^{3a}$ are as defined above,
$R^2$ is $CF_3$,
  $CCl_3$,
  $CBr_3$, or

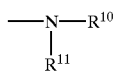

wherein $R^{10}$ is hydrogen and $R^{11}$ is 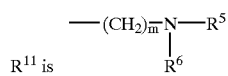

wherein $R^5$, $R^6$, and m are as defined above, or

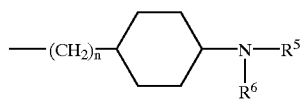

wherein n, $R^5$, and $R^6$ are as defined above.

3. The compound of claim 2 wherein A is:

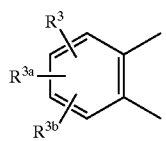

wherein $R^3$, $R^{3a}$, and $R^{3b}$ are each independently the same or different and are hydrogen, alkyl, aryl, heteroaryl, —$OR^4$ wherein $R^4$ is hydrogen, alkyl, aryl, aralkyl, acetyl, or

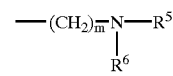

wherein $R^5$ and $R^6$ are each the same or different and are hydrogen, alkyl, cycloalkyl, acetyl, or $R^5$ and $R^6$ are taken together to form a 5- to 7-membered ring optionally containing an oxygen atom or N—$R^4$ wherein $R^4$ is as defined above and m is an integer of 2 to 5,

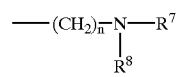

wherein n is zero or an integer of 1 and $R^7$ and $R^8$ are each independently the same or different and are hydrogen, alkyl, aryl, aralkyl, acetyl, or

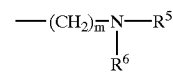

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

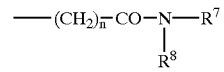

wherein $R^7$, $R^8$, and n are as defined above,

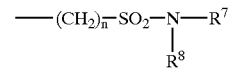

wherein $R^7$, $R^8$, and n are as defined above,

—$(CH_2)_n$—$SO_2OR^4$ wherein $R^4$ and n are as defined above,

—$(CH_2)_n$—$CO_2R^4$ wherein $R^4$ and n are as defined above,

—CH$_2$OR$^4$ wherein R$^4$ is as defined above,
halogen,
CF$_3$,
CBr$_3$,
CCl$_3$, or
NO$_2$;

R$^1$ is 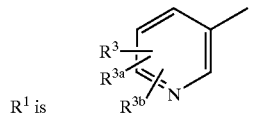

wherein R$^3$, R$^{3a}$, and R$^{3b}$ are as defined above,

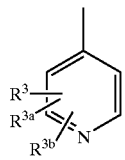

wherein R$^3$, R$^{3a}$, and R$^{3b}$ are as defined above,

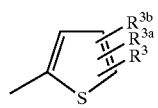

wherein R$^3$, R$^{3a}$, and R$^{3b}$ are as defined above,

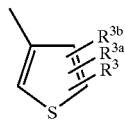

wherein R$^3$, R$^{3a}$, and R$^{3b}$ are as defined above,

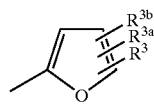

wherein R$^3$, R$^{3a}$, and R$^{3b}$ are as defined above,

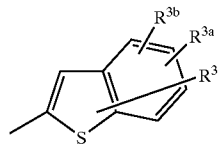

wherein R$^3$, R$^{3a}$, and R$^{3b}$ are as defined above,

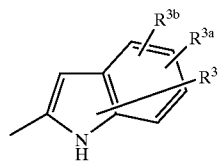

wherein R$^3$, R$^{3a}$, and R$^{3b}$ are as defined above, or

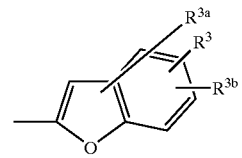

wherein R$^3$ and R$^{3a}$ are as defined above; and

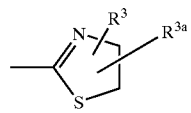

R$^2$ is CF$_3$,
CCl$_3$,
CBr$_3$, or

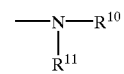

wherein R$^{10}$ is hydrogen and R$^{11}$ is

R$^{11}$ is 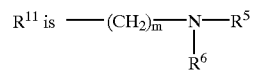

wherein R$^5$, R$^6$, and m are as defined above, or

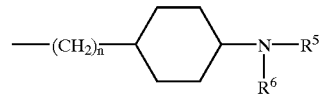

wherein n, R$^5$, and R$^6$ are as defined above.

4. The compound of claim 3 wherein

A is 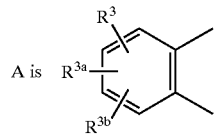

wherein R$^3$, R$^{3a}$, and R$^{3b}$ are each independently the same or different and are hydrogen,
alkyl,
aryl,
heteroaryl,
—OR$^4$ wherein R$^4$ is hydrogen,
alkyl,
aryl,
heteroaryl,
aralkyl,
acetyl, or

wherein
R⁵ and R⁶ are each the same or different and are hydrogen, alkyl, cycloalkyl, acetyl, or R⁵ and R⁶ are taken together to form a 5- to 7-membered ring optionally containing an oxygen atom or N—R⁴ wherein R⁴ is as defined above and m is an integer of 2 to 5,

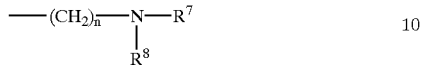

wherein n is zero or an integer of 1 and R⁷ and R⁸ are each independently the same or different and are
hydrogen,
alkyl,
aryl,
aralkyl,
acetyl, or

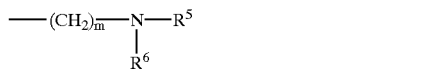

wherein R⁵ and R⁶ are as defined above or R⁷ and R⁸ taken together to form a 5- to 7-membered ring optionally containing an oxygen atom or N—R⁴ wherein R⁴ and m are as defined above,

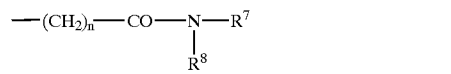

wherein R⁷, R⁸, and n are as defined above,

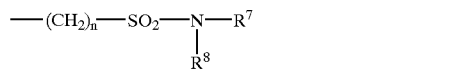

wherein R⁷, R⁸, and n are as defined above,
—(CH₂)ₙ—SO₂OR⁴ wherein R⁴ and n are as defined above,
—(CH₂)ₙ—CO₂R⁴ wherein R⁴ and n are as defined above,
—CH₂OR⁴ wherein R⁴ is as defined above,
halogen,
CF₃,
CBr₃,
CCl₃, or
NO₂;

R¹ is 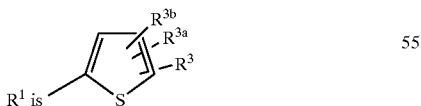

wherein R³, R³ᵃ, and R³ᵇ are as defined above,

wherein R³, R³ᵃ, and R³ᵇ are as defined above,

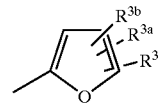

wherein R³, R³ᵃ, and R³ᵇ are as defined above,

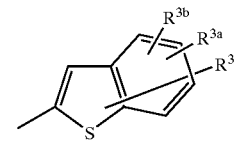

wherein R³, R³ᵃ, and R³ᵇ are as defined above,

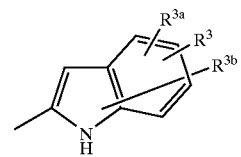

wherein R³, R³ᵃ, and R³ᵇ are as defined above,

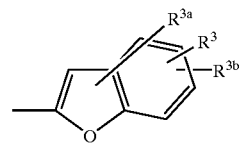

wherein R³, R³ᵃ, and R³ᵇ are as defined above, or

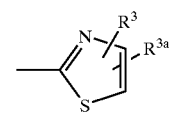

wherein R³ and R³ᵃ are as defined above; and
R² is CF₃,
CCl₃,
CBr₃, or

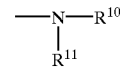

wherein R¹⁰ is hydrogen and

R¹¹ is 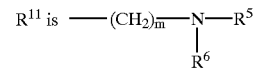

wherein R⁵, R⁶, and m are as defined above, or

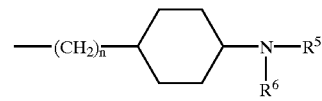

wherein n, R⁵, and R⁶ are as defined above.

5. The compound of claim 4 wherein

A is 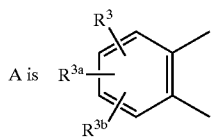

wherein $R^3$, $R^{3a}$, and $R^{3b}$ are each independently the same or different and are hydrogen,
alkyl,
aryl,
heteroaryl,
—$OR^4$ wherein $R^4$ is hydrogen,
alkyl,
aryl,
aralkyl,
acetyl, or

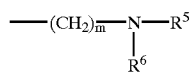

wherein $R^5$ and $R^6$ are each the same or different and are hydrogen, alkyl, cycloalkyl, acetyl, or $R^5$ and $R^6$ are taken together to form a 5- to 7-membered ring optionally containing an oxygen atom or N—$R^4$ wherein R is as defined above and m is an integer of 2 to 5,

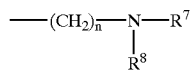

wherein n is zero or an integer of 1 and $R^7$ and $R^8$ are each independently the same or different and are hydrogen,
alkyl,
aryl,
aralkyl,
acetyl, or

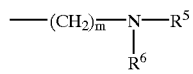

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

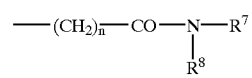

wherein $R^7$, $R^8$, and n are as defined above,

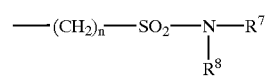

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$;

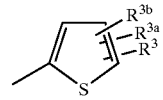

wherein $R^3$, $R^{3a}$, and $R^{3b}$ are as defined above,

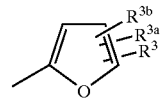

wherein $R^3$, $R^{3a}$, and $R^{3b}$ are as defined above,

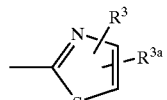

wherein $R^3$, and $R^{3a}$ are as defined above,

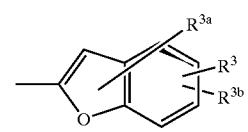

wherein $R^3$, $R^{3a}$, and $R^{3b}$ are as defined above, or

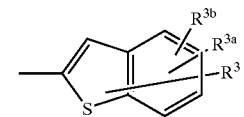

wherein $R^3$, $R^{3a}$, and $R^{3b}$ are as defined above, and

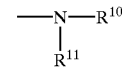

$R^2$ wherein $R^{10}$ is hydrogen and

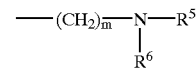

wherein $R^5$, $R^6$, and m are as defined above, or

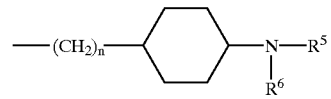

wherein n, $R^5$, and $R^6$ are as defined above.

6. A compound which is selected from the group consisting of:
N-(1-Azabicyclo[2.2.2]octanyl-3-pyridinyl)-3-(2-pyridinyl)-2-quinoxalinamine;

N-[3-(1H-Imidazol-1-yl)propyl]-3-(2-pyridinyl)-2-quinoxalinamine;
N-[2-(1-Methyl pyrrolidinyl)ethyl]-3-(2-pyridinyl)-2-quinoxalinamine;
1-[3-[[3-Pyridinyl-2-quinoxalinamine]amino]propyl]-2-pyrrolidinone;
N-[4-(4-Morpholinyl)phenyl]-3-(2-pyridinyl)quinoxalinamine;
N-(4-Piperidinylmethyl)-3-(2-pyridinyl)-2-quinoxalinamine;
N-[4-(Dimethylamino)phenyl]-3-(2-pyridinyl)-2-quinoxalinamine;
N-Methyl-N-[4-[[3-(2-pyridinyl)-2-quinoxalinyl]amino]phenyl]-acetamide;
N-(6,7-Dichloro-3-pyridin-2-yl-quinoxalin-2-yl)-cyclohexane-1,4-diamine;
2-[1,4']Bipiperidinyl-1'-yl-6,7-dichloro-3-pyridin-2-yl-quinoxaline;
(6,7-Dichloro-3-pyridin-2-yl-quinoxalin-2-yl)-(4-diethylaminomethyl-phenyl)amine;
N'-(6,7-Dichloro-3-furan-2-yl-quinoxalin-2-yl)-N,N-dimethyl-propane-1,3-diamine;
N'-(6,7-Dichloro-3-thiophen-2-yl-quinoxalin-2-yl)-N,N-dimethyl-propane-1,3-diamine;

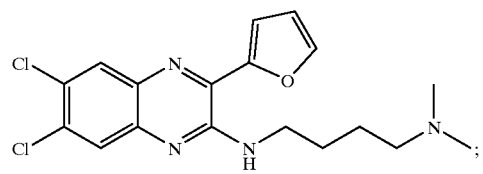

N'-(6,7-Difluoro-3-thiophen-2-yl-quinoxalin-2-yl)-N,N-dimethyl-butane-1,4-diamine;

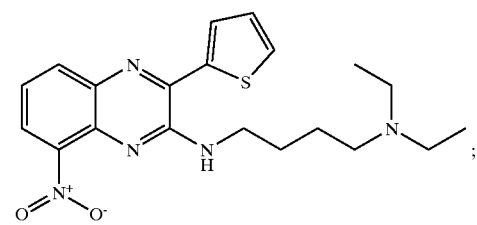

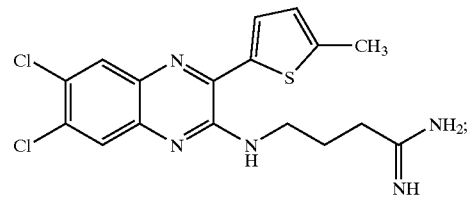

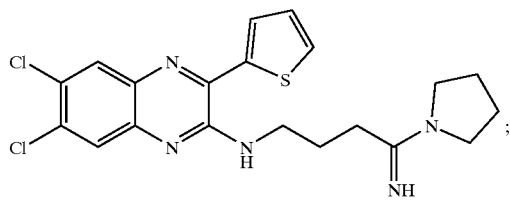

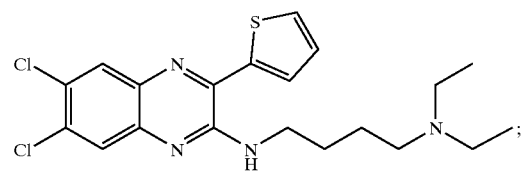

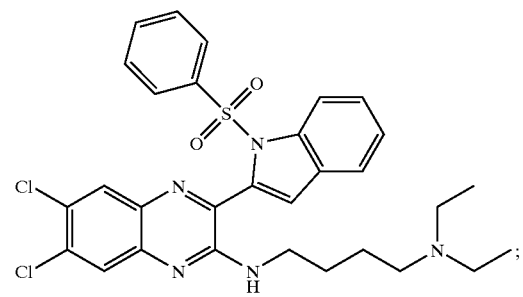

N'-[6,7-Dichloro-3-(1H-indol-2-yl)-quinoxalin-2-yl]-N,N-diethyl-butane-1,4-diamine;

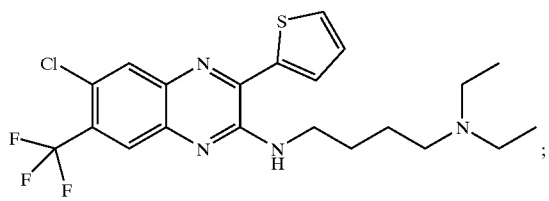

N'-(3-Benzo[b]thiophen-2-yl-6,7-dichloro-quinoxalin-2-yl)-N,N-diethyl-butane-1,4-diamine;

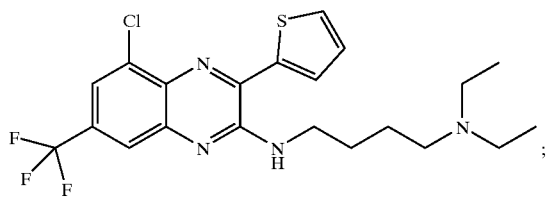

N,N-Diethyl-N'-(3-thiophen-2-yl-7-trifluoromethyl-quinoxalin-2-yl)-butane-1,4-diamine;
N'-[6,7-Dichloro-3-(5-methyl-thiophen-2-yl)-quinoxalin-2-yl]-N,N-diethyl-butane-1,4-diamine;

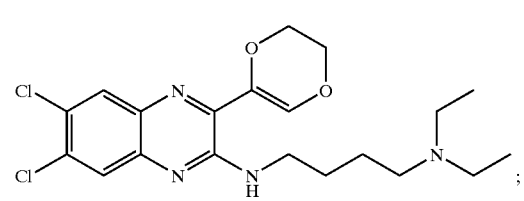

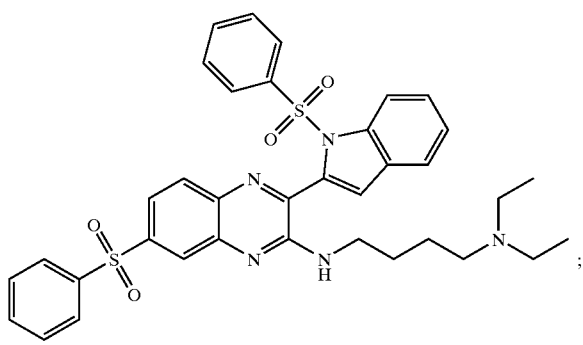

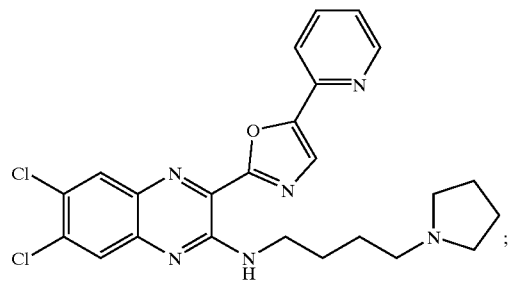

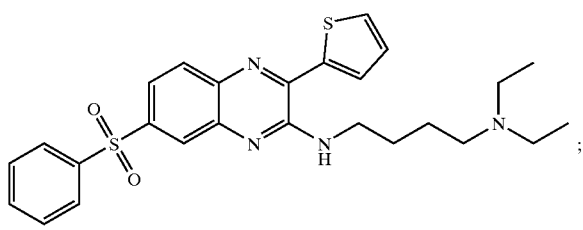

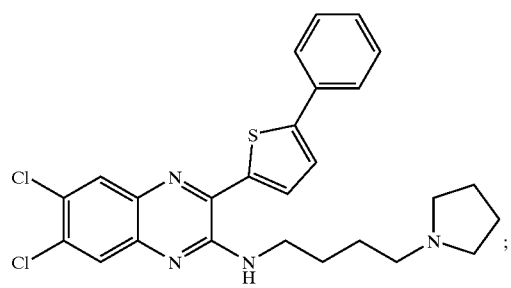

N'-(6,7-Dichloro-3-thiazol-2-yl-quinoxalin-2-yl)-N,N-dimethyl-propane-1,3-diamine;

N'-(3-[2.2']Bithiophenyl-5-yl-6,7-dichloro-quinoxalin-2-yl)-N,N-diethyl-butane-1,4-diamine;

N'-[6,7-Dichloro-3-(5-chloro-thiophen-2-yl)-quinoxalin-2-yl]-N,N-diethyl-butane-1,4-diamine;

N'-[6,7-Dichloro-3-(5-methoxy-thiophen-2-yl)-quinoxalin-2-yl]-N,N-diethyl-butane-1,4-diamine;

N'-[6,7-Dichloro-3-(5-propyl-thiophen-2-yl)-quinoxalin-2-yl]-N,N-diethyl-butane-1,4-diamine;

N'-(3-Benzofuran-2-yl-6,7-dichloro-quinoxalin-2-yl)-N,N-diethyl-butane-1,4-diamine;

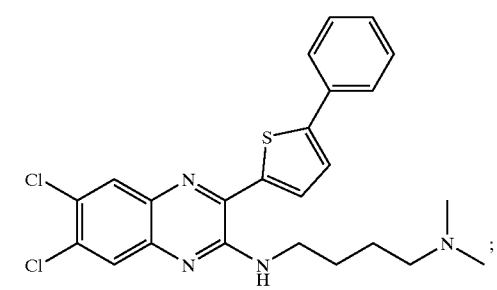

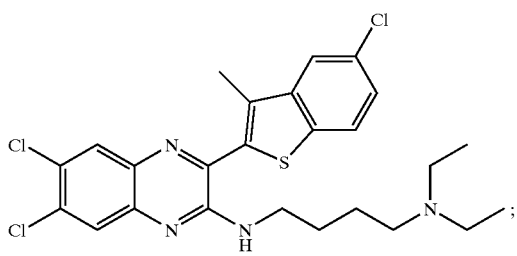

N'-[6,7-Dichloro-3-dibenzothiophen-4-yl-quinoxalin-2-yl)-N,N-diethyl-butane-1,4-diamine;

[6,7-Dichloro-3-(5-phenyl-oxazol-2-yl)-quinoxalin-2-yl-(4-pyrrolidin-1-yl-butyl)-amine;

[6,7-Dichloro-3-(5-thiophen-2-yl-oxazol)-quinoxalin-2-yl]-(4-pyrrolidin-1-yl-butyl)-amine;

N-(6,7-Dichloro-3-pyridinyl-3-quinoxalin-2-yl)-N',N'-dimethyl-cyclohexane-1,4-diamine;

N-(6,7-Dichloro-3-pyridin-4-yl-quinoxalin-2-yl)-N',N'-dimethyl-cyclohexane-1,4-diamine;

N-(6,7-Dimethoxy-3-pyridin-2yl-quinoxalin-2-yl)-N',N'-dimethyl-cyclohexane-1,4-diamine;

N,N-Dimethyl-N'-(3-pyridin-2-yl-7,8-dihydro-6H-cyclopenta[g]quinoxalin-2-yl)-cyclohexane-1,4-diamine;

N'-(6,7-Dichloro-3-pyridin-2-yl-quinoxalin-2-yl)-N,N-dimethyl-butane-1,4-diamine;

N'-(6,7-Dichloro-3-pyridin-2-yl-quinoxalin-2-yl)-N,N-dimethyl-pentane-1,5-diamine;

N-(6,7-Dichloro-3-pyridin-2-yl-quinoxalin-2-yl)-pentane-1,5-diamine;

N'-(6,7-Dichloro-3-pyridin-2-yl-quinoxalin-2-yl)-N,N-dimethyl-hexane-1,6-diamine;

[3-(6,7-Dichloro-3-pyridin-2-yl-quinoxalin-2-ylsulfanyl)-propyl]-dimethylamine;

(6,7-Dichloro-2-pyridin-2-yl-quinoxalin-2-yl)-(3-morpholin-4-yl-propyl)-amine;

(6,7-Dichloro-3-pyridin-2-yl-quinoxalin-2-yl)-(3-methoxypropyl)-amine;

N'-1-[3-(6,7-Dichloro-3-pyridin-2-yl-quinoxalin-2-ylamino)-propyl]-N'-1-methylpropane-1,3-diamine;

2-{[3-(6,7-Dichloro-3-pyridin-2-yl-quinoxalin-2-ylamino)-propyl]-(2-hydroxy-ethyl)-amino}-ethanol;
{4-[4-(2-Chloro-phenyl)-piperidin-1-yl]-butyl-(6,7-dichloro-3-pyridin-2-yl-quinoxalin-2-yl)}amine;
(6,7-Dichloro-3-pyridin-2-yl-quinoxalin-2-yl)-(1-phenyl-4-piperidin-1-yl-butyl)-amine;
[6,7-Dichloro-3-(1-ethyl-5-phenyl-imidazol-2-yl)-quinoxalin-2-yl]-(4-pyrrolidin-1-yl-butyl)-amine;
[6,7-Dichloro-3-(1-phenyl-imidazol-2-yl)-quinoxalin-2-yl]-(4-pyrrolidin-1-yl-butyl)-amine;
[6,7-Dichloro-3-[1-ethyl-5-(5-methyl-thiophene-2-yl)-imidazol-5-yl]-quinoxalin-2-yl]-(4-pyrrolidin-1-yl-butyl)-amine; and
[6,7-Dichloro-3-(1-phenyl-pyrazolo-5-yl)-quinoxalin-2-yl]-(4-pyrrolidin-1-yl-butyl)-amine;
or a pharmaceutically acceptable salt thereof.

7. A compound of Formula I:

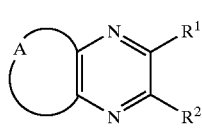

I wherein A is

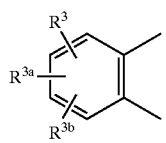

wherein $R^3$, $R^{3a}$, and $R^{3b}$ are each independently the same or different and are hydrogen,
aryl-SO$_2$—,
aryl,
heteroaryl,
—OR$^4$ wherein R$^4$ is hydrogen,
  alkyl,
  aryl,
  aralkyl,
  acetyl, or

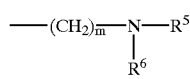

wherein
R$^5$ and R$^6$ are each the same or different and are hydrogen, alkyl, cycloalkyl, acetyl, —(CH$_2$)$_m$—OH, or R$^5$ and R$^6$ are taken together to form a 5- to 7-membered ring optionally containing an oxygen atom or N—R$^4$ wherein R$^4$ is as defined above and m is an integer of 2 to 5,

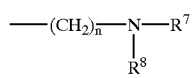

wherein n is zero or an integer of 1 and R$^7$ and R$^8$ are each independently the same or different and are hydrogen,
alkyl,
aryl,
aralkyl,
acetyl, or

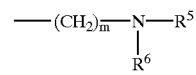

wherein R$^5$ and R$^6$ are as defined above or R$^7$ and R$^8$ taken together to form a 5- to 7-membered ring optionally containing an oxygen atom or N—R$^4$ wherein R$^4$ and m are as defined above,

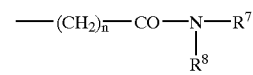

wherein R$^7$, R$^8$, and n are as defined above,

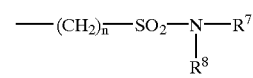

wherein R$^7$, R$^8$, and n are as defined above,
—(CH$_2$)$_n$—SO$_2$OR$^4$ wherein R$^4$ and n are as defined above,
—(CH$_2$)$_n$—CO$_2$R$^4$ wherein R$^4$ and n are as defined above,
—CH$_2$OR$^4$ wherein R$^4$ is as defined above,
CF$_3$,
CBr$_3$,
CCl$_3$, or
NO$_2$;

R is 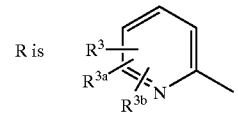

wherein R$^3$, R$^{3a}$, and R$^{3b}$ are each independently the same or different and are hydrogen,
alkyl,
aryl-SO$_2$—,
aryl,
heteroaryl,
—OR$^4$ wherein R$^4$ is hydrogen,
  alkyl,
  aryl,
  aralkyl,
  acetyl, or

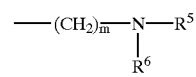

wherein
R$^5$ and R$^6$ are each the same or different and are hydrogen, alkyl, cycloalkyl, acetyl, —(CH$_2$)$_m$—OH, or R$^5$ and R$^6$ are taken together to form a 5- to 7-membered ring optionally containing an oxygen atom or N—R$^4$ wherein R$^4$ is as defined above and m is an integer of 2 to 5,

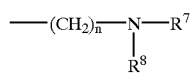

wherein n is zero or an integer of 1 and $R^7$ and $R^8$ are each independently the same or different and are hydrogen,
alkyl,
aryl,
aralkyl,
acetyl, or

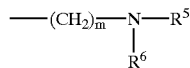

wherein $R^5$ and $R^6$ are as defined above or $R^7$ and $R^8$ taken together to form a 5- to 7-membered ring optionally containing an oxygen atom or $N-R^4$ wherein $R^4$ and m are as defined above,

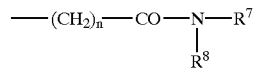

wherein $R^7$, $R^8$, and n are as defined above,

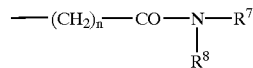

wherein $R^7$, $R^8$, and n are as defined above,
$-(CH_2)_n-SO_2OR^4$ wherein $R^4$ and n are as defined above,
$-(CH_2)_n-CO_2R^4$ wherein $R^4$ and n are as defined above,
$-CH_2OR^4$ wherein $R^4$ is as defined above,
halogen,
$CF_3$,
$CBr_3$,
$CCl_3$, or
$NO_2$;
$R^2$ is $CF_3$,
$CCl_3$,
$CBr_3$, or

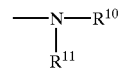

wherein $R^{10}$ is hydrogen,
alkyl, or
aralkyl, and $R^{11}$ is 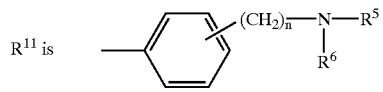

wherein n, $R^5$, and $R^6$ are as defined above,

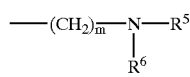

wherein $R^5$, $R^6$, and m are as defined above,

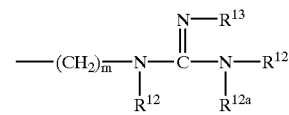

wherein $R^{12}$ and $R^{12a}$ are each independently the same or different and are hydrogen, alkyl, or aryl, or taken together can form a 5- to 7-membered ring, and
$R^{13}$ is hydrogen or alkyl, and
m is as defined above,

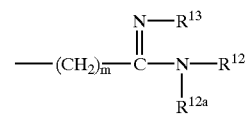

wherein m, $R^{12}$, $R^{12a}$, and $R^{13}$ are as defined above,

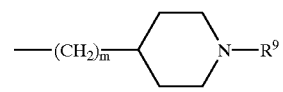

wherein $R^9$ and m are as defined above,

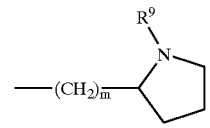

wherein $R^9$ and m are as defined above,

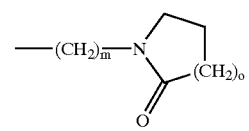

wherein m and o are as defined above,

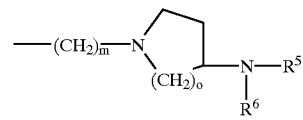

wherein n, o, $R^5$, and $R^6$ are as defined above,

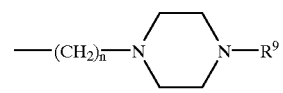

wherein n and $R^9$ are as defined above,

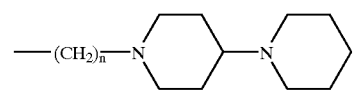

wherein n is as defined above,

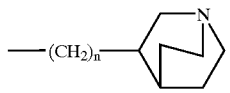

wherein n is as defined above,

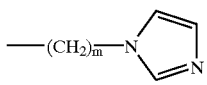

wherein m is as defined above, or
$R^{10}$ and $R^{11}$ when taken together can form a 5- to 7-membered ring optionally containing an oxygen atom or N—$R^4$ wherein $R^4$ is as defined above;
or a pharmaceutically acceptable salt thereof.

8. The compound of claim 6, wherein said compound is N'-(6,7-Dichloro-3-thiophen-2-yl-quinoxalin-2-yl)-N,N-dimethyl-propane-1,3-diamine.

9. A method for preparing a compound having the Formula Ia:

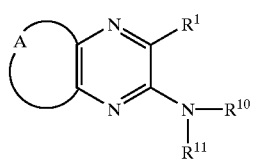

Ia wherein A is

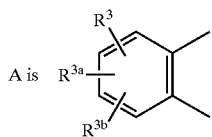

wherein $R^3$, $R^{3a}$ and $R^{3b}$ are each independently the same or different and are hydrogen,
  alkyl,
  aryl-$SO_2$—,
  aryl,
  heteroaryl,
  —$OR^4$ wherein $R^4$ is hydrogen,
    alkyl,
    aryl,
    aralkyl,
    acetyl, or

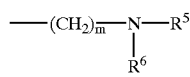

wherein
  $R^5$ and $R^6$ are each the same or different and are hydrogen, alkyl, cycloalkyl, acetyl, —$(CH_2)_m$—OH, or $R^5$ and $R^6$ are taken together to form a 5- to 7-membered ring optionally containing an oxygen atom or N—$R^4$ wherein $R^4$ is as defined above and m is an integer of 2 to 5,

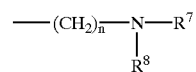

wherein n is zero or an integer of 1 and $R^7$ and $R^8$ are each independently the same or different and are hydrogen,
  alkyl,
  aryl,
  aralkyl,
  acetyl, or

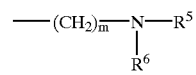

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

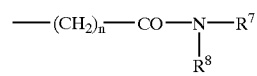

wherein $R^7$, $R^8$, and n are as defined above,

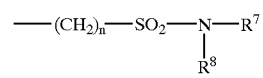

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$,

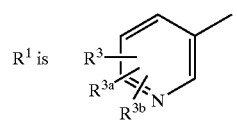

wherein $R^3$, $R^{3a}$, and $R^{3b}$ are as defined above,

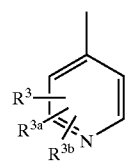

wherein $R^3$, $R^{3a}$, and $R^{3b}$ are as defined above,

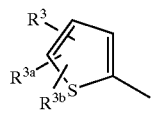

wherein $R^3$, $R^{3a}$, and $R^{3b}$ are as defined above,

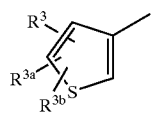

wherein $R^3$, $R^{3a}$, and $R^{3b}$ are as defined above,

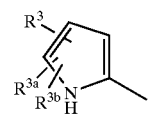

wherein $R^3$, $R^{3a}$, and $R^{3b}$ are as defined above,

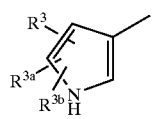

wherein $R^3$, $R^{3a}$, and $R^{3b}$ are as defined above,

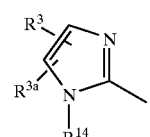

wherein $R^{14}$ is hydrogen, alkyl, aryl, or aralkyl, and $R^3$ and $R^{3a}$ are as defined above,

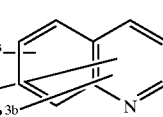

wherein $R^3$, $R^{3a}$, and $R^{3b}$ are as defined above,

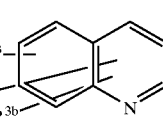

wherein $R^3$, $R^{3a}$, and $R^{3b}$ are as defined above,

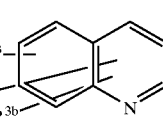

wherein $R^3$, $R^{3a}$, and $R^{3b}$ are as defined above,

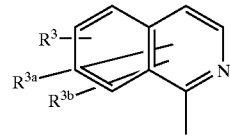

wherein $R^3$, $R^{3a}$, and $R^{3b}$ are as defined above,

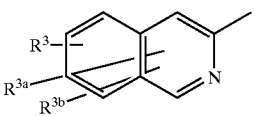

wherein $R^3$, $R^{3a}$, and $R^{3b}$ are as defined above,

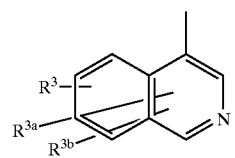

wherein $R^3$, $R^{3a}$, and $R^{3b}$ are as defined above,

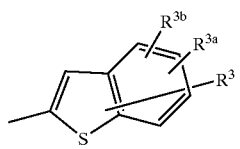

wherein $R^3$, $R^{3a}$, and $R^{3b}$ are as defined above,

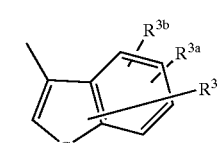

wherein $R^3$, $R^{3a}$, and $R^{3b}$ are as defined above,

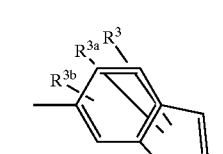

wherein $R^3$, $R^{3a}$, and $R^{3b}$ are as defined above,

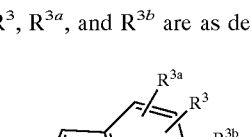

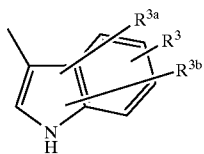

wherein $R^3$, $R^{3a}$, and $R^{3b}$ are as defined above,

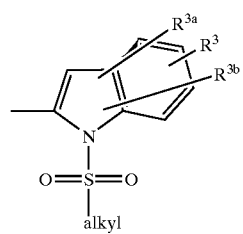

wherein $R^3$, $R^{3a}$, and $R^{3b}$ are as defined above,

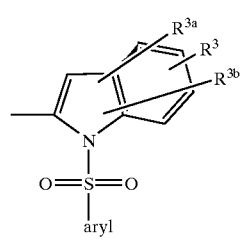

wherein $R^3$, $R^{3a}$, and $R^{3b}$ are as defined above,

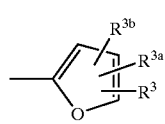

wherein $R^3$, $R^{3a}$, and $R^{3b}$ are as defined above,

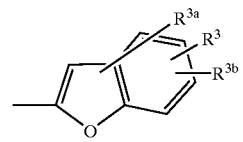

wherein $R^3$, $R^{3a}$, and $R^{3b}$ are as defined above,

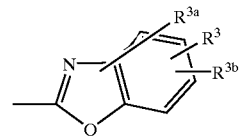

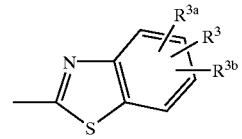

wherein $R^3$, $R^{3a}$, and $R^{3b}$ are as defined above,

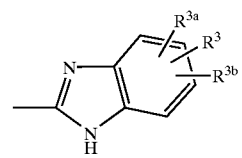

wherein $R^3$, $R^{3a}$, and $R^{3b}$ are as defined above,

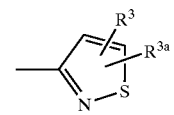

wherein $R^3$, $R^{3a}$, and $R^{3b}$ are as defined above,

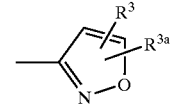

wherein $R^3$ and $R^{3a}$ are as defined above,

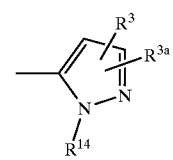

wherein $R^3$, $R^{3a}$, and $R^{14}$ are as defined above,

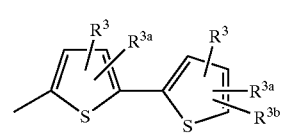

wherein $R^3$, $R^{3a}$, and $R^{3b}$ are as defined above,

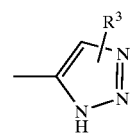

wherein R³ is as defined above,

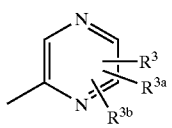

wherein R³, R³ᵃ, and R³ᵇ are as defined above,

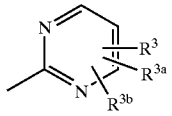

wherein R³, R³ᵃ and R³ᵇ are as defined above,

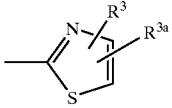

wherein R³ and R³ᵃ are as defined above,

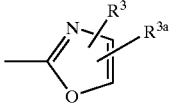

wherein R³ and R³ᵃ are as defined above,

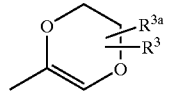

wherein R³ and R³ᵃ are as defined above,

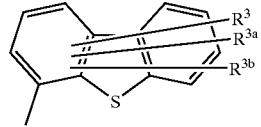

wherein R³, R³ᵃ and R³ᵇ are as defined above,

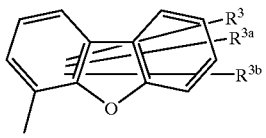

wherein R³, R³ᵃ, and R³ᵇ are as defined above, or

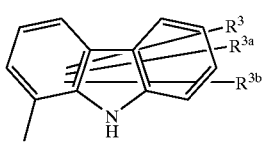

wherein R³, R³ᵃ, and R³ᵇ are as defined above; and
R¹⁰ is hydrogen,
alkyl, or
aralkyl, and R¹¹ is 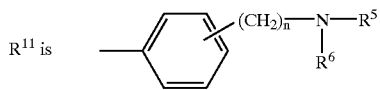

wherein n, R⁵, and R⁶ are as defined above,

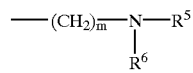

wherein R⁵, R⁶, and m are as defined above,

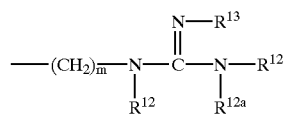

wherein R¹² and R¹²ᵃ are each independently the same or different and are hydrogen, alkyl, or aryl, or taken together can form a 5- to 7-membered ring, and R¹³ is hydrogen or alkyl, and
m is as defined above,

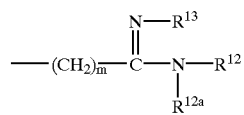

wherein m, R¹², R¹²ᵃ, and R¹³ are as defined above,

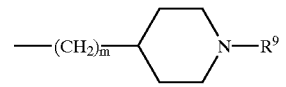

wherein R⁹ and m are as defined above,

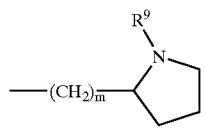

wherein R⁹ and m are as defined above,

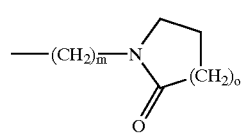

wherein m and o are as defined above,

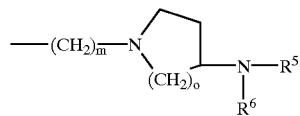

wherein n, o, $R^5$, and $R^6$ are as defined above,

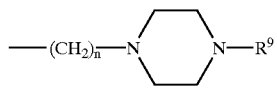

wherein n and $R^9$ are as defined above,

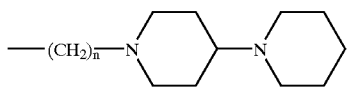

wherein n is as defined above,

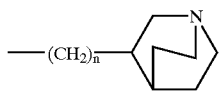

wherein n is as defined above,

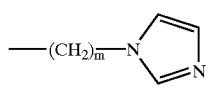

wherein m is as defined above, or
$R^{10}$ and $R^{11}$ when taken together can form a 5- to 7-membered ring optionally containing an oxygen atom or N—$R^4$ wherein $R^4$ is as defined above;
or a pharmaceutically acceptable salt thereof, comprises reacting a compound of Formula III

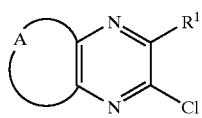     III wherein A and $R^1$ are as defined above with a compound of Formula IV

     IV wherein $R^{10}$ and $R^{11}$ are as defined above in a solvent to afford a compound of Formula Ia.

10. A pharmaceutical composition comprising a compound according to claim 1 in admixture with a pharmaceutically acceptable excipient, diluent, or carrier.

11. A pharmaceutical composition adapted for administration as an agent for treating psoriasis, atopic dermatitis, disease associated with pathologicalangiogenesis, cancer, asthma, chronic obstructive pulmonary disease, adult respiratory distress syndrome, arthritis, inflammatory bowel disease, Crohn's disease, ulcerative colitis, gastric ulcer, septic shock, endotoxicshock, gram-negative sepsis, toxic shock syndrome, stroke, cardiac and renal reperfusion injury, glomerulo-nephritis, or thrombosis, Alzheimer's disease, graft versus host reaction, allograft rejections, or allergic diseases comprising a therapeutically effective amount of a compound of Formula I in admixture with a pharmaceutically acceptable excipient, diluent, or carrier, wherein said compound of Formula I is:

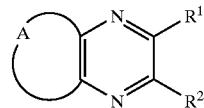     I wherein A is

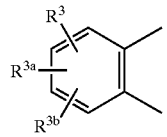

wherein $R^3$, $R^{3a}$, and $R^{3b}$ are each independently the same or different and are hydrogen,
  alkyl,
  aryl-SO$_2$—,
  aryl,
  heteroaryl,
  —OR$^4$ wherein $R^4$ is hydrogen,
    alkyl,
    aryl,
    aralkyl,
    acetyl, or

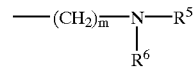

wherein
$R^5$ and $R^6$ are each the same or different and are hydrogen, alkyl, cycloalkyl, acetyl, —(CH$_2$)$_m$—OH, or $R^5$ and $R^6$ are taken together to form a 5- to 7-membered ring optionally containing an oxygen atom or N—$R^4$ wherein $R^4$ is as defined above and m is an integer of 2 to 5,

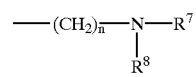

wherein n is zero or an integer of 1 and $R^7$ and $R^8$ are each independently the same or different and are hydrogen,
alkyl,
aryl,
aralkyl,
acetyl, or

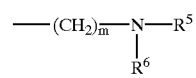

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

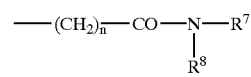

wherein $R^7$, $R^8$, and n are as defined above,

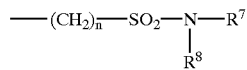

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$, R is 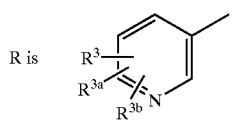

wherein $R^3$, $R^{3a}$, and $R^{3b}$ are as defined above,

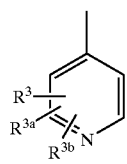

wherein $R^3$, $R^{3a}$, and $R^{3b}$ are as defined above,

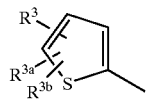

wherein $R^3$, $R^{3a}$, and $R^{3b}$ are as defined above,

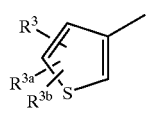

wherein $R^3$, $R^{3a}$, and $R^{3b}$ are as defined above,

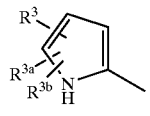

wherein $R^3$, $R^{3a}$, and $R^{3b}$ are as defined above,

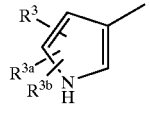

wherein $R^3$, $R^{3a}$, and $R^{3b}$ are as defined above,

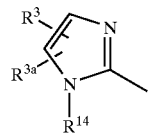

wherein $R^{14}$ is hydrogen, alkyl, aryl, or aralkyl, and $R^3$ and $R^{3a}$ are as defined above,

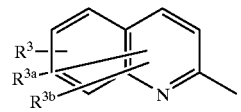

wherein $R^3$, $R^{3a}$, and $R^{3b}$ are as defined above,

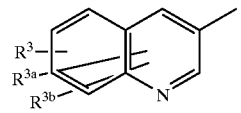

wherein $R^3$, $R^{3a}$, and $R^{3b}$ are as defined above,

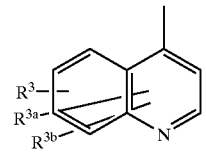

wherein $R^3$, $R^{3a}$, and $R^{3b}$ are as defined above,

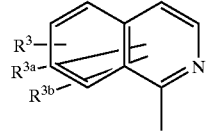

wherein $R^3$, $R^{3a}$, and $R^{3b}$ are as defined above,

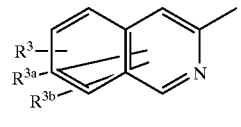

wherein $R^3$, $R^{3a}$, and $R^{3b}$ are as defined above,

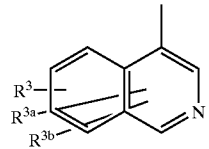

wherein R³, R³ᵃ, and R³ᵇ are as defined above,

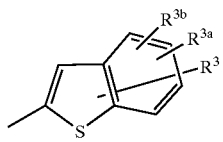

wherein R³, R³ᵃ, and R³ᵇ are as defined above,

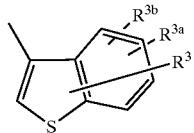

wherein R³, R³ᵃ, and R³ᵇ are as defined above,

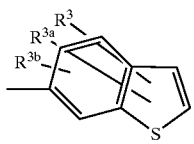

wherein R³, R³ᵃ, and R³ᵇ are as defined above,

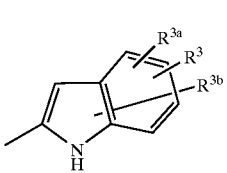

wherein R³, R³ᵃ, and R³ᵇ are as defined above,

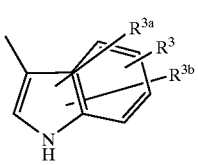

wherein R³, R³ᵃ, and R³ᵇ are as defined above,

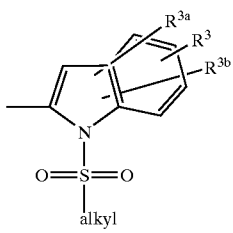

wherein R³, R³ᵃ, and R³ᵇ are as defined above,

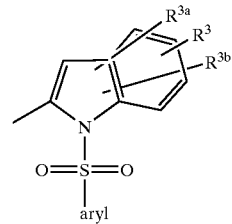

wherein R³, R³ᵃ, and R³ᵇ are as defined above,

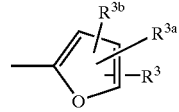

wherein R³, R³ᵃ, and R³ᵇ are as defined above,

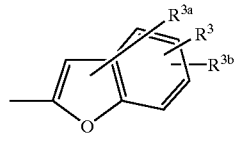

wherein R³, R³ᵃ, and R³ᵇ are as defined above,

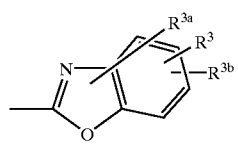

wherein R³, R³ᵃ, and R³ᵇ are as defined above,

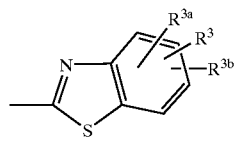

wherein R³, R³ᵃ, and R³ᵇ are as defined above,

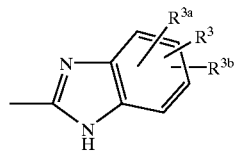

wherein R³, R³ᵃ, and R³ᵇ are as defined above,

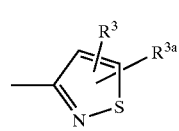

wherein $R^3$ and $R^{3a}$ are as defined above,

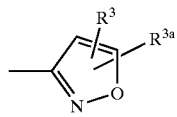

wherein $R^3$ and $R^{3a}$ are as defined above,

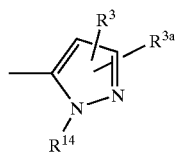

wherein $R^3$, $R^{3a}$, and $R^{14}$ are as defined above,

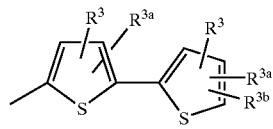

wherein $R^3$, $R^{3a}$, and $R^{3b}$ are as defined above,

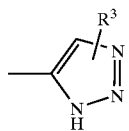

wherein $R^3$ is as defined above,

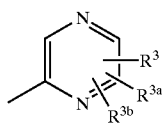

wherein $R^3$, $R^{3a}$, and $R^{3b}$ are as defined above,

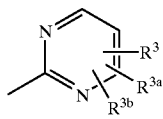

wherein $R^3$, $R^{3a}$, and $R^{3b}$ are as defined above,

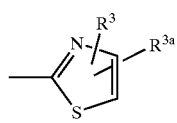

wherein $R^3$ and $R^{3a}$ are as defined above,

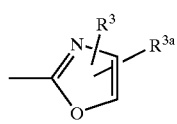

wherein $R^3$ and $R^{3a}$ are as defined above,

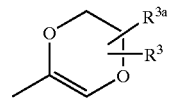

wherein $R^3$ and $R^{3a}$ are as defined above,

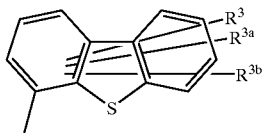

wherein $R^3$, $R^{3a}$, and $R^{3b}$ are as defined above,

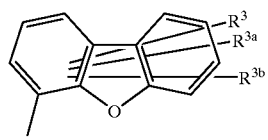

wherein $R^3$, $R^{3a}$, and $R^{3b}$ are as defined above, or

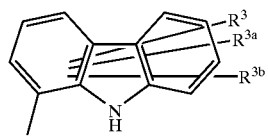

wherein $R^3$, $R^{3a}$, and $R^{3b}$ are as defined above; and
$R^2$ is $CF_3$,
$CCl_3$,
$CBr_3$, or

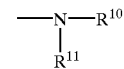

wherein $R^{10}$ is hydrogen,
alkyl, or
aralkyl, and $R^{11}$ is 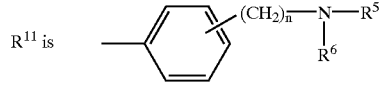

wherein n, $R^5$, and $R^6$ are as defined above,

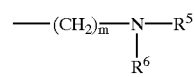

wherein $R^5$, $R^6$, and m are as defined above,

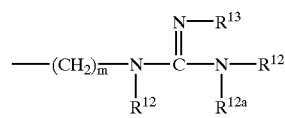

wherein $R^{12}$ and $R^{12a}$ are each independently the same or different and are hydrogen, alkyl, or aryl, or taken together can form a 5- to 7-membered ring, and
$R^{13}$ is hydrogen or alkyl, and
m is as defined above,

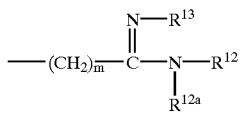

wherein m, $R^{12}$, $R^{12a}$, and $R^{13}$ are as defined above,

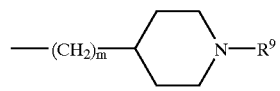

wherein $R^9$ and m are as defined above,

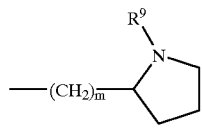

wherein $R^9$ and m are as defined above,

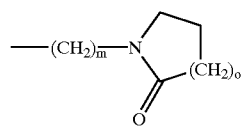

wherein m and o are as defined above,

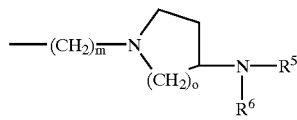

wherein n, o, $R^5$, and $R^6$ are as defined above,

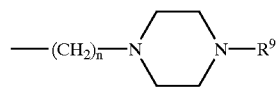

wherein n and $R^9$ are as defined above,

wherein n is as defined above,

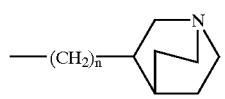

wherein n is as defined above,

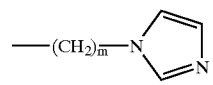

wherein m is as defined above, or
$R^{10}$ and $R^{11}$ when taken together can form a 5- to 7-membered ring optionally containing an oxygen atom or N—$R^4$ wherein $R^4$ is as defined above;
or a pharmaceutically acceptable salt thereof.

12. A pharmaceutical composition suitable for oral administration comprising a compound of Formula I in admixture with a pharmaceutically acceptable excipient, diluent, or carrier for oral dosage, wherein said compound of Formula I is:

I

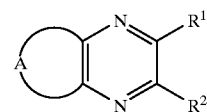

wherein A is

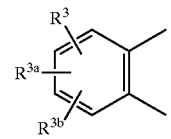

wherein $R^3$, $R^{3a}$, and $R^{3b}$ are each independently the same or different and are hydrogen,
alkyl,
aryl-$SO_2$—,
aryl,
heteroaryl,
—$OR^4$ wherein $R^4$ is hydrogen,
    alkyl,
    aryl,
    aralkyl,
    acetyl, or

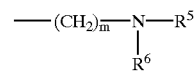

wherein
$R^5$ and $R^6$ are each the same or different and are hydrogen, alkyl, cycloalkyl, acetyl, —$(CH_2)_m$—OH, or $R^5$ and $R^6$ are taken together to form a 5- to 7-membered ring optionally containing an oxygen atom or N—$R^4$ wherein $R^4$ is as defined above and m is an integer of 2 to 5,

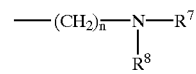

wherein n is zero or an integer of 1 and $R^7$ and $R^8$ are each independently the same or different and are hydrogen,
alkyl,
aryl, aralkyl,
acetyl, or

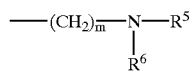

wherein $R^5$ and $R^6$ are as defined above or $R^7$ and $R^8$ taken together to form a 5- to 7-membered ring optionally containing an oxygen atom or N—$R^4$ wherein $R^4$ and m are as defined above,

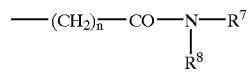

wherein $R^7$, $R^8$, and n are as defined above,

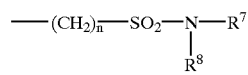

wherein $R^7$, $R^8$, and n are as defined above,
—$(CH_2)_n$—$SO_2OR^4$ wherein $R^4$ and n are as defined above,
—$(CH_2)_n$—$CO_2R^4$ wherein $R^4$ and n are as defined above,
—$CH_2OR^4$ wherein $R^4$ is as defined above,
halogen,
$CF_3$,
$CBr_3$,
$CCl_3$, or
$NO_2$,

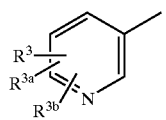

wherein $R^3$, $R^{3a}$, and $R^{3b}$ are as defined above,

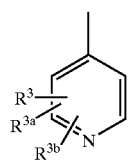

wherein $R^3$, $R^{3a}$, and $R^{3b}$ are as defined above,

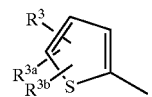

wherein $R^3$, $R^{3a}$, and $R^{3b}$ are as defined above,

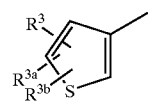

wherein $R^3$, $R^{3a}$, and $R^{3b}$ are as defined above,

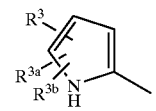

wherein $R^3$, $R^{3a}$, and $R^{3b}$ are as defined above,

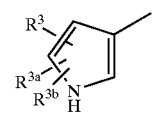

wherein $R^3$, $R^{3a}$, and $R^{3b}$ are as defined above,

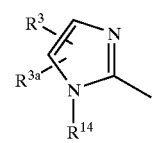

wherein $R^{14}$ is hydrogen, alkyl, aryl, or aralkyl, and $R^3$ and $R^{3a}$ are as defined above,

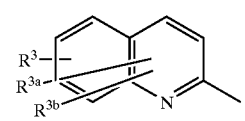

wherein $R^3$, $R^{3a}$, and $R^{3b}$ are as defined above,

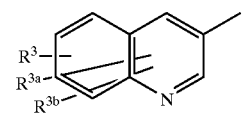

wherein $R^3$, $R^{3a}$, and $R^{3b}$ are as defined above,

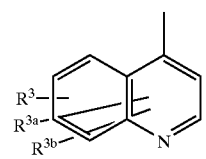

wherein $R^3$, $R^{3a}$, and $R^{3b}$ are as defined above,

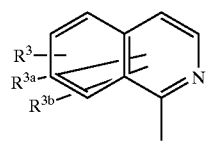

wherein $R^3$, $R^{3a}$, and $R^{3b}$ are as defined above,

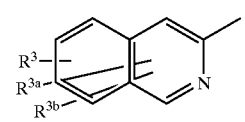

wherein $R^3$, $R^{3a}$, and $R^{3b}$ are as defined above, wherein R³, R³ᵃ, and R³ᵇ are as defined above,

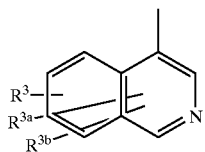

wherein R³, R³ᵃ, and R³ᵇ are as defined above,

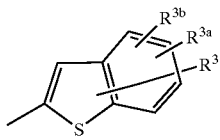

wherein R³, R³ᵃ, and R³ᵇ are as defined above,

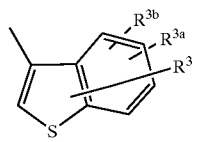

wherein R³, R³ᵃ, and R³ᵇ are as defined above,

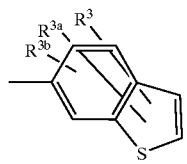

wherein R³, R³ᵃ, and R³ᵇ are as defined above,

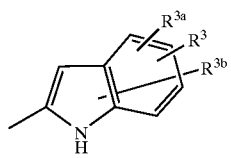

wherein R³, R³ᵃ, and R³ᵇ are as defined above,

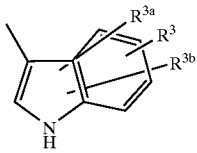

wherein R³, R³ᵃ, and R³ᵇ are as defined above,

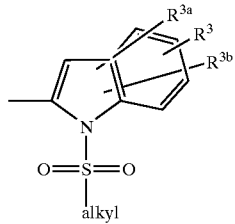

wherein R³, R³ᵃ, and R³ᵇ are as defined above,

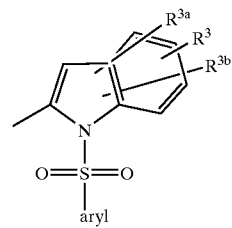

wherein R³, R³ᵃ, and R³ᵇ are as defined above,

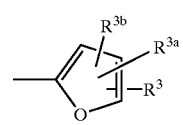

wherein R³, R³ᵃ, and R³ᵇ are as defined above,

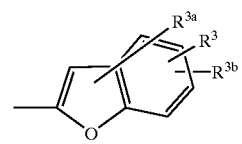

wherein R³, R³ᵃ, and R³ᵇ are as defined above,

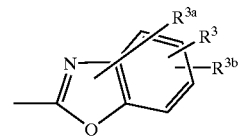

wherein R³, R³ᵃ, and R³ᵇ are as defined above,

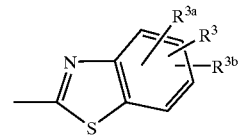

wherein R³, R³ᵃ, and R³ᵇ are as defined above,

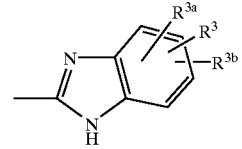

wherein R³, R³ᵃ, and R³ᵇ are as defined above,

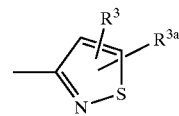

wherein $R^3$ and $R^{3a}$ are as defined above,

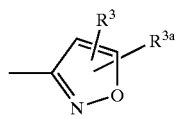

wherein $R^3$ and $R^{3a}$ are as defined above,

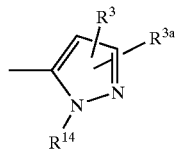

wherein $R^3$, $R^{3a}$, and $R^{14}$ are as defined above,

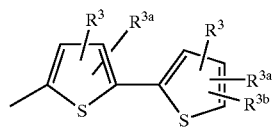

wherein $R^3$, $R^{3a}$, and $R^{3b}$ are as defined above,

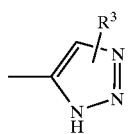

wherein $R^3$ is as defined above,

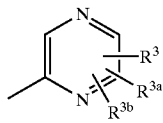

wherein $R^3$, $R^{3a}$, and $R^{3b}$ are as defined above,

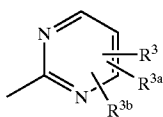

wherein $R^3$, $R^{3a}$, and $R^{3b}$ are as defined above,

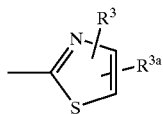

wherein $R^3$ and $R^{3a}$ are as defined above,

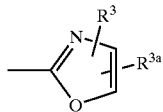

wherein $R^3$ and $R^{3a}$ are as defined above,

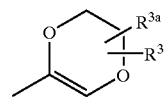

wherein $R^3$ $R^{3a}$ are as defined above,

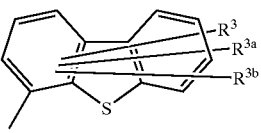

wherein $R^3$, $R^{3a}$, and $R^{3b}$ are as defined above,

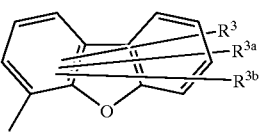

wherein $R^3$, $R^{3a}$, and $R^{3b}$ are as defined above, or

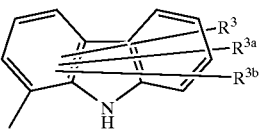

wherein $R^3$, $R^{3a}$, and $R^{3b}$ are as defined above; and
$R^2$ is $CF_3$,
$CCl_3$,
$CBr_3$, or

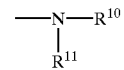

wherein $R^{10}$ is hydrogen,
alkyl, or
aralkyl, and $R^{11}$ is 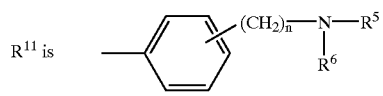

wherein n, $R^5$, and $R^6$ are as defined above,

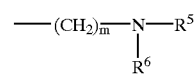

wherein $R^5$, $R^6$, and m are as defined above,

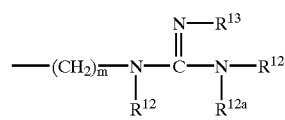

wherein $R^{12}$ and $R^{12a}$ are each independently the same or different and are hydrogen, alkyl, or aryl, or taken together can form a 5- to 7-membered ring, and $R^{13}$ is hydrogen or alkyl, and
m is as defined above,

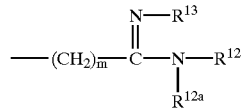

wherein m, $R^{12}$, $R^{12a}$, and $R^{13}$ are as defined above,

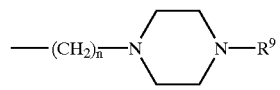

wherein $R^9$ and m are as defined above,

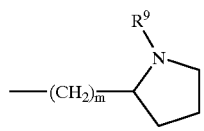

wherein $R^9$ and m are as defined above,

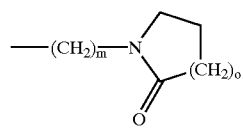

wherein m and o are as defined above,

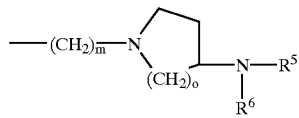

wherein n, o, $R^5$, and $R^6$ are as defined above,

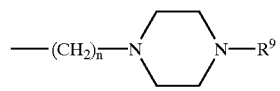

wherein n and $R^9$ are as defined above,

wherein n is as defined above,

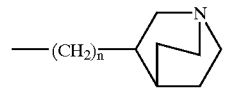

wherein n is as defined above,

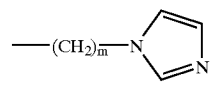

wherein m is as defined above, or
$R^{10}$ and $R^{11}$ when taken together can form a 5- to 7-membered ring optionally containing an oxygen atom or N—$R^4$ wherein $R^4$ is as defined above;
or a pharmaceutically acceptable salt thereof.

13. A pharmaceutical composition comprising a compound according to claim 7 in admixture with a pharmaceutically acceptable excipient, diluent, or carrier.

14. A pharmaceutical composition comprising a compound according to claim 6 in admixture with a pharmaceutically acceptable excipient, diluent, or carrier.

15. A method of treating a chemokine-mediated disease state, wherein the chemokine binds to an IL-8a (CXCR1) or b (CXCR2) receptor in a mammal, which comprises administering to said mammal an effective amount of a compound of claim 1.

16. A method of treating a chemokine-mediated disease state, wherein the chemokine binds to an IL-8a (CXCR1) or b (CXCR2) receptor in a mammal, which comprises administering to said mammal an effective amount of a compound of claim 6.

17. A method of treating a chemokine-mediated disease state, wherein the chemokine binds to an IL-8a (CXCR1) or b (CXCR2) receptor in a mammal, which comprises administering to said mammal an effective amount of a compound of claim 7.

18. The method of claim 15, wherein the mammal is affected with a chemokine-mediated disease selected from the group consisting of psoriasis, atopic dermatitis, disease associated with pathological angiogenesis, cancer, asthma, chronic obstructive pulmonary disease, adult respiratory distress syndrome, arthritis, inflammatory bowel disease, Crohn's disease, ulcerative colitis, gastric ulcer, septic shock, endotoxic shock, gram-negative sepsis, toxic shock syndrome, stroke, cardiac and renal reperfusion injury, glomerulo-nephritis, thrombosis, Alzheimer's disease, graft versus host reaction, allograft rejections, or allergic disease.

19. The method of claim 16, wherein the mammal is affected with a chemokine-mediated disease selected from the group consisting of psoriasis, atopic dermatitis, disease associated with pathological angiogenesis, cancer, asthma, chronic obstructive pulmonary disease, adult respiratory distress syndrome, arthritis, inflammatory bowel disease, Crohn's disease, ulcerative colitis, gastric ulcer, septic shock, endotoxic shock, gram-negative sepsis, toxic shock syndrome, stroke, cardiac and renal reperfusion injury, glomerulo-nephritis, thrombosis, Alzheimer's disease, graft versus host reaction, allograft rejections, or allergic disease.

20. The method of claim 17, wherein the mammal is affected with a chemokine-mediated disease selected from the group consisting of psoriasis, atopic dermatitis, disease associated with pathological angiogenesis, cancer, asthma, chronic obstructive pulmonary disease, adult respiratory distress syndrome, arthritis, inflammatory bowel disease, Crohn's disease, ulcerative colitis, gastric ulcer, septic shock, endotoxic shock, gram-negative sepsis, toxic shock syndrome, stroke, cardiac and renal reperfusion injury, glomerulo-nephritis, thrombosis, Alzheimer's disease, graft versus host reaction, allograft rejections, or allergic disease.

* * * * *